(12) United States Patent
Armstrong

(10) Patent No.: US 10,501,554 B2
(45) Date of Patent: Dec. 10, 2019

(54) INTERNALIZING MOIETIES FOR TREATMENT OF CANCER

(71) Applicant: Valerion Therapeutics, LLC, Concord, MA (US)

(72) Inventor: Dustin D. Armstrong, Quincy, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 33 days.

(21) Appl. No.: 15/507,012

(22) PCT Filed: Aug. 27, 2015

(86) PCT No.: PCT/US2015/047180
§ 371 (c)(1),
(2) Date: Feb. 27, 2017

(87) PCT Pub. No.: WO2016/033324
PCT Pub. Date: Mar. 3, 2016

(65) Prior Publication Data
US 2018/0127509 A1   May 10, 2018

Related U.S. Application Data

(60) Provisional application No. 62/192,920, filed on Jul. 15, 2015, provisional application No. 62/102,988, filed on Jan. 13, 2015, provisional application No. 62/042,755, filed on Aug. 27, 2014, provisional application No. 62/042,771, filed on Aug. 27, 2014.

(51) Int. Cl.
*A61K 39/395* (2006.01)
*C07K 16/30* (2006.01)
*A61P 35/00* (2006.01)
*A61K 39/00* (2006.01)

(52) U.S. Cl.
CPC .............. *C07K 16/30* (2013.01); *A61P 35/00* (2018.01); *A61K 2039/505* (2013.01); *C07K 2317/24* (2013.01); *C07K 2317/526* (2013.01); *C07K 2317/565* (2013.01); *C07K 2317/71* (2013.01); *C07K 2317/73* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 7,189,396 | B1 | 3/2007 | Weisbart |
| 8,609,615 | B2 | 12/2013 | Armstrong |
| 8,834,866 | B2 | 9/2014 | Armstrong |
| 9,114,178 | B2 | 8/2015 | Armstrong |
| 9,447,394 | B2 | 9/2016 | Armstrong |
| 2008/0292618 | A1 | 11/2008 | Weisbart |
| 2010/0143358 | A1 | 6/2010 | Weisbart |
| 2013/0259862 | A1 | 10/2013 | Nishimura |
| 2013/0266570 | A1 | 10/2013 | Weisbart et al. |
| 2015/0064181 | A1 | 3/2015 | Armstrong |
| 2015/0152170 | A1 | 6/2015 | Armstrong et al. |
| 2016/0089451 | A1 | 3/2016 | Armstrong |
| 2016/0108133 | A1 | 4/2016 | Armstrong et al. |

FOREIGN PATENT DOCUMENTS

| | | |
|---|---|---|
| WO | WO-97/32602 A1 | 9/1997 |
| WO | WO-2008/091911 A2 | 7/2008 |
| WO | WO-2008/148063 A1 | 12/2008 |
| WO | WO-2010/044894 | 4/2010 |
| WO | WO-2010/148010 A1 | 12/2010 |
| WO | WO 2012/135831 A1 | 10/2012 |
| WO | WO-2012/145125 A1 | 10/2012 |
| WO | WO-2013/138662 A1 | 9/2013 |
| WO | WO-2013/177428 | 11/2013 |
| WO | WO-2014/130722 A1 | 8/2014 |
| WO | WO-2014/130723 A1 | 8/2014 |
| WO | WO-2015/106290 A1 | 7/2015 |
| WO | WO-2015/192092 A1 | 12/2015 |
| WO | WO-2016/033324 A1 | 3/2016 |

OTHER PUBLICATIONS

MacCallum et al, J. Mol. Biol., 262, 732-745, 1996.*
Pascalis et al, Journal of Immunology, 2002, vol. 169, pp. 3076-3084.*
Vajdos et al Journal of Molecular Biology, 2002, vol. 320, pp. 415-428.*
Chen, et al., "Enhancement and Destruction of Antibody Function by Somatic Mutation: Unequal Occurrence is Controlled by V Gene Combinatorial Associations," *The EMBO Journal*, 14(12):2784-2794 (1995).
Kussie, et al., "A Single Engineered Amino Acid Substitution Changes Antibody Fine Specificity," *The Journal of Immunology*, 152:146-152 (1994).
Rudikoff, et al., "Single Amino Acid Substitution Altering Antigen-Binding Specificity," *Proc. Natl. Acad. Sci. USA*, 79:1979-1983 (1982).
Wu, et al., "Humanization of a Murine Monoclonal Antibody by Simultaneous Optimization of Framework and CDR Residues," *J. Mol. Biol.*, 294:151-162 (1999).
Non-Final Office Action in U.S. Appl. No. 15/111,160, dated Apr. 18, 2018.
Charpin, et al., "Anatomic Pathology Original Article Correlation with Patient Followup," (1997) https://acadmic.oup/com/ajcp/article-pdf/107/5/534/4981866/ajcpath107-0534.pdf [retrieved on Feb. 22, 2018].
Horak, et al., "Angiogenesis, Assessed by Platelet/Endothelial Cell Adhesion Molecule Antibodies, as Indicator of Node Metastases and Survival in Breast Cancer," *The Lancet*, 340 (8828): 1120-1124 (1992).
Kurzawski, "Importance of Microsatellite Instability (MSI) in Colorectal Cancer: MSI as a Diagnostic Tool," *Annals of Oncology*, 15(Suppl_4): iv283-iv 284 (2004).

(Continued)

*Primary Examiner* — Mark Halvorson
(74) *Attorney, Agent, or Firm* — Lisa M. Warren, Esq.; Morse, Barnes-Brown & Pendleton, P.C.

(57) ABSTRACT

In certain embodiments, the present disclosure provides compositions and methods for treating tumors and cancer.

22 Claims, 19 Drawing Sheets

Specification includes a Sequence Listing.

(56) References Cited

OTHER PUBLICATIONS

Ramsoekh, et al., "Cancer Risk in MLH1, MSH2 and MSH6 Mutation Carriers; Different Risk Profiles may Influence Clinical Management," *Hereditary Cancer in Clinical Practice*, 7(1):17 (2009).
Schozen, et al., "The Ki-67 Protein: from the Known and the Unknown," *Journal of Cellular Physiology*, 182(3), :311-322 (2000).
Supplementary European Search Report from EP15837057, dated Feb. 22, 2018.
Abhinandan, et al., "Analyzing the "Degree of Humanness" of Antibody Sequences," *Journal Molecular Biology*, vol. 369:852-862 (2007).
Ducancel, "Molecular Engineering of Antibodies for Therapeutic and Diagnostic Purposes," *Landes Bioscience*, 4(4): 445-457 (2012).
Hansen, et al., "Antibody-Mediated Hsp70 Protein Therapy," *Brain Research*, 1088(1):187-196 (2006).
Hansen, et al., "Intranuclear Protein Transduction Through a Nucleoside Salvage Pathway," *The Journal of Biological Chemistry*, vol. 282(29):20790-20793 (2007).
Hansen et al., "Targeting Cancer with a Lupus Autoantibody," *Science Translation Medicine*, vol. (157):157ra142 (2012).
Kunik, et al., "Structural Consensus Among Antibodies Defines the Antigen Binding Site," *PLoS Computational Biology*, vol. 8(2): (12 pages) (2012).
Pennycooke, et al., "Differential Expression of Human Nucleoside Transporters in Normal and Tumor Tissue," *Biochemical and Biophysical Research Communications*, vol. 280(3):951-959 (2001).
Weidle, et al., "The Translational Potential for Target Validation and Therapy Using Intracellular Antibodies in Oncology," *Cancer Genomics and Proteomics*, vol. 10, pp. 239-250 (2013).

Weisbart, et al., "An Autoantibody is Modified for Use as a Delivery System to Target the Cell Nucleus: Therapeutic Implications," *Journal of Autoimmunity*, vol. 11(5):539-546 (1998).
Weisbart, et al., "An intracellular Delivery Vehicle for Protein Transduction of Micro-Dystrophin," *Journal of Drug Targeting*, vol. 13(2):81-87 (2005).
Weisbart, et al., "Novel Protein Transfection of Primary Rat Cortical Neurons Using an Antibody that Penetrates Living Cells," *The Journal of Immunology*, vol. 164:6020-6026 (2000).
Weisbart, et al., "Nuclear Delivery of p53 C-Terminal Peptides into Cancer Calls Using scFv Fragments of a Monoclonal Antibody that Penetrates Living Cells," *Cancer Letters*, vol. 195(2):211-219 (2003).
Weisbart, et al., "Cell Type Specific Targeted Intracellular Delivery into Muscle of a Monoclonal Antibody that Binds Myosin IIb," *Molecular Immunology*, vol. 39(13):783-789 (2003).
Yamane-Ohnuki, "Production of Therapeutic Antibodies with Controlled Fucosylation," *Landes Bioscience*, 1(3): 230-236 (2009).
Zack, et al., "DNA Mimics a Self-Protein That May Be a Target for Some Anti-DNA Antibodies in Systemic Lupus Erythematosus," *The Journal of Immunology*, 154:1987-1994, (Feb. 15, 1995).
Zack, et al., "Mechanisms of Cellular Penetration and Nuclear Localization of an Anti-Double Strand DNA Autoantibody," *Journal of Immunology*, vol. 157(5):2082-2088 (1996).
International Search Report from PCT/US2015/011269, dated Apr. 14, 2015.
International Search Report from PCT/US2015/047180, dated Nov. 10, 2015.
Supplementary European Search Report from EP 15735467.1, dated Jun. 1, 2017.
Boland, C. Richard, and Ajay Goel. "Microsatellite instability in colorectal cancer." *Gastroenterology* 138.6 (2010): 2073-2087.
Notice of Allowance and Fee(s) Due in U.S. Appl. No. 15/111,160, dated Oct. 12, 2018.

* cited by examiner

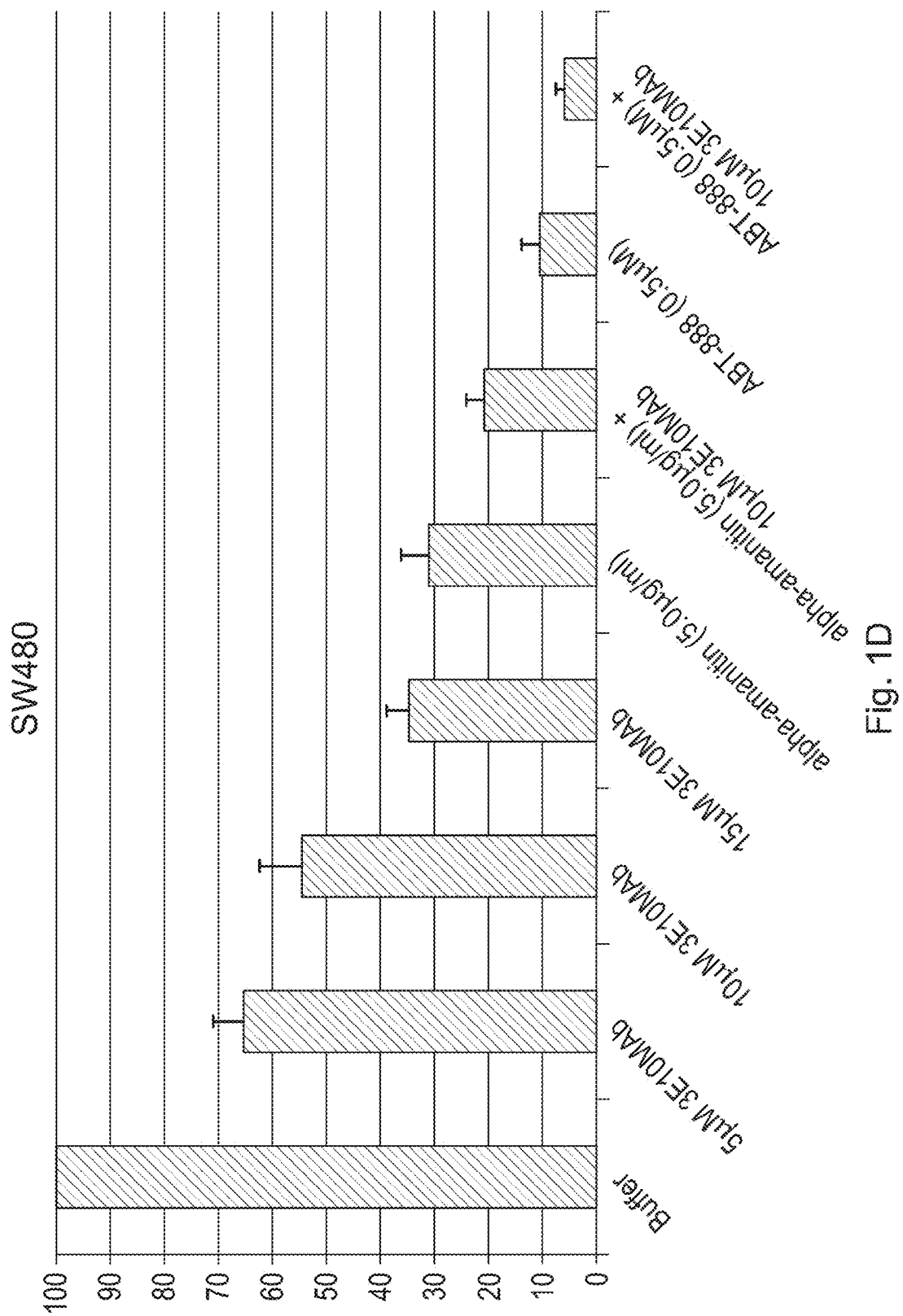

SEQUENCE LISTING

<160> NUMBER OF SEQ ID NOS: 52

<210> SEQ ID NO 1
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Ser Gly Ser Ser Thr Ile
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Arg Gly Leu Leu Leu Asp Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ser Val Ser Thr Ser Ser Tyr Ser Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Ser Arg Glu Phe Pro Trp Thr
```

<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Ser Cys Arg Ala Ser Lys Ser Val Ser Thr Ser
            20                  25                  30

Ser Tyr Ser Tyr Met His Trp Tyr Gln Gln Lys Pro Glu Lys Ala Pro
        35                  40                  45

Lys Leu Leu Ile Lys Tyr Ala Ser Tyr Leu Gln Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln His Ser Arg
                85                  90                  95

Glu Phe Pro Trp Thr Phe Gly Ala Gly Thr Lys Leu Glu Leu Lys
            100                 105                 110

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Lys Pro Gly Gly
1               5                   10                  15

-continued

```
Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
            115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Ile Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Arg Gly Leu Leu Leu Asp Tyr Trp Gly Gln Gly Thr Leu Val
            100                 105                 110

Thr Val Ser Ser
            115

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgctgctac atccacgcag ctgcgcggag cgcagctgcg tggatgtagc agcgc          55

<210> SEQ ID NO 12
<211> LENGTH: 333
<212> TYPE: DNA
<213> ORGANISM: Mus musculus

<400> SEQUENCE: 12
gacattgtgc tgacacagtc tcctgcttcc ttagctgtat ctctggggca gagggccacc     60
```

```
atctcctgca gggccagcaa aagtgtcagt acatctagct atagttacat gcactggtac      120
caacagaaac caggacagcc acccaaactc ctcatcaagt atgcatccta cctagaatct      180
ggggttcctg ccaggttcag tggcagtggg tctgggacag actttcacct caacatccat      240
cctgtggagg aggaggatgc tgcaacatat tactgtcagc acagtaggga gtttccgtgg      300
acgttcggtg gaggcaccaa gctggagttg aaa                                  333
```

<210> SEQ ID NO 13
<211> LENGTH: 348
<212> TYPE: DNA
<213> ORGANISM: Mus musculus

<400> SEQUENCE: 13

```
gaggtgcagc tggtggagtc tgggggaggc ttagtgaagc ctggagggtc ccggaaactc      60
tcctgtgcag cctctggatt cactttcagt aactatggaa tgcactgggt ccgtcaggct     120
ccagagaagg ggctggagtg ggttgcatac attagtagtg gcagtagtac catctactat     180
gcagacacag tgaagggccg attcaccatc tccagagaca atgccaagaa caccctgttc     240
ctgcaaatga ccagtctaag gtctgaggac acagccatgt attactgtgc aaggcggggg     300
ttactacttg actactgggg ccaaggcacc actctcacag tctcctca                  348
```

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 gtaaacaa                                                                8

<210> SEQ ID NO 15
<211> LENGTH: 107
<212> TYPE: PRT
<213> ORGANISM: Homo sapiens

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 22
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 16

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Glu Phe Gly Leu Ser Trp Leu Phe Leu Val Ala Ile Leu Lys Gly
1               5                   10                  15

Val Gln Cys

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gggtgaacct gcaggtgggc aaagatgtcc                                    30

<210> SEQ ID NO 19
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcgctgcaat gaattataag ctgcgcggag cgcagcttat aattcattgc agcgc         55

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcgctgcaat atagtctaag ctgcgcggag cgcagcttag actatattgc agcgc         55

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcgctgctat ataagtctag ctgcgcggag cgcagctaga cttatatagc agcgc         55
```

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gcgctgcaca taaatttacg ctgcgcggag cgcagcgtaa atttatgtgc agcgc    55

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
gcgctgctag aaatatatag ctgcgcggag cgcagctata tatttctagc agcgc    55

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Synthetic probe

<400> SEQUENCE: 24
actttaggta aacaactaaa gtggaactttt agttgtttac ctaaagt    47

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic probe

<400> SEQUENCE: 25
atcttaagta aacaattaag atggaatctt aattgtttac ttaagat    47

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic probe

<400> SEQUENCE: 26
tcatatagta aacaatatat gaggatcata tattgtttac tatatga    47

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ctgtctcgta gcactcgcga tacggagtat cgttttttttt tttagacag    49

-continued

```
<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Gly Ile His
1

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Gly Ile His
1               5

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Thr Ser Gly Ser Gly Lys Ser Ser Glu Gly Lys Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Tyr Gly Met His
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

-continued

```
Tyr Ile Ser Ser Gly Ser Ser Thr Ile Tyr Tyr Ala Asp Thr Val Lys
1               5                   10                  15

Gly

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gly Leu Leu Leu Asp Tyr
1               5

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Ser Lys Ser Val Ser Thr Ser Ser Tyr Ser Tyr Met His
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ala Ser Tyr Leu Glu Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln His Ser Arg Glu Phe Pro Trp Thr
1               5

<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Thr Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
             20                  25                  30

Ser Tyr Ser Tyr Leu Ala Trp Tyr Gln Gln Lys Pro Glu Lys Ala Pro
        35                  40                  45

Lys Leu Leu Ile Lys Tyr Ala Ser Tyr Leu Gln Ser Gly Val Pro Ser
 50                  55                  60

Arg Phe Ser Gly Ser Gly Ser Gly Thr Asp Phe Thr Leu Thr Ile Ser
 65                  70                  75                  80
```

Ser Leu Gln Pro Glu Asp Phe Ala Thr Tyr Tyr Cys Gln His Ser Arg
                85                  90                  95

Glu Phe Pro Trp Thr Phe Gly Ala Gly Thr Lys Leu Glu Leu Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Tyr Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 42
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Gly Met His Trp Val Arg Gln Ala Pro Gly Lys Gly Leu Glu Tyr Val
        35                  40                  45

Ser Tyr Ile Ser Ser Gly Ser Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Arg Gly Leu Leu Leu Asp Tyr Trp Gly Gln Gly Thr Leu Val
            100                 105                 110

Thr Val Ser Ser
        115

<210> SEQ ID NO 43
<211> LENGTH: 242
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 43

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Tyr Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Trp Thr Phe Gly Gln Gly Thr Lys Val Glu Ile Lys Gly
            100                 105                 110

Gly Gly Gly Ser Gly Gly Gly Gly Ser Gly Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ser Ala Ser Gly Phe Thr Phe Ser Asn Tyr Gly Met
145                 150                 155                 160

His Trp Val Arg Gln Ala Pro Gly Lys Gly Leu Glu Tyr Val Ser Tyr
                165                 170                 175

Ile Ser Ser Gly Ser Ser Thr Ile Tyr Tyr Ala Asp Thr Val Lys Gly
            180                 185                 190

Arg Phe Thr Ile Ser Arg Asp Asn Ser Lys Asn Thr Leu Tyr Leu Gln
        195                 200                 205

Met Ser Ser Leu Arg Ala Glu Asp Thr Ala Val Tyr Tyr Cys Val Lys
    210                 215                 220

Arg Gly Leu Leu Leu Asp Tyr Trp Gly Gln Gly Thr Leu Val Thr Val
225                 230                 235                 240

Ser Ser
```

<210> SEQ ID NO 44
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcgctgccga gagcggcctg ctgcgcggag cgcagcaggc cgctctcggc agcgc      55

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gly Gly Ser Gly Gly Gly Ser Gly Gly Gly Ser Gly Gly
1               5                   10
```

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ttcctgcgta aacaagcagg aaggattcct gcttgtttac gcaggaa                47

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Gln Lys Leu Ile Ser Glu Glu Asp Leu
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Ile Ser Ser Gly Ser Ser Thr Ile Tyr Tyr Ala Asp Ser Val Lys
1               5                   10                  15

Gly

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Lys Ser Val Ser Thr Ser Ser Tyr Ser Tyr Leu Ala
1               5                   10                  15

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 51

Tyr Ala Ser Tyr Leu Gln Ser
1               5

<210> SEQ ID NO 52
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 trttkry                                                              7
```

INTERNALIZING MOIETIES FOR TREATMENT OF CANCER

RELATED APPLICATIONS

This application is a national stage filing under 35 U.S.C. § 371 of International Application No. PCT/US2015/047180, filed on Aug. 27, 2015, claims the benefit of priority to U.S. provisional application Ser. No. 62/042,755, filed Aug. 27, 2014; U.S. provisional application Ser. No. 62/042,771, filed Aug. 27, 2014; U.S. provisional application 62/102,988, filed Jan. 13, 2015; and U.S. provisional application Ser. No. 62/192,920, filed Jul. 15, 2015. The entire contents of each of the foregoing applications are hereby incorporated by reference in their entirety. International Application No. PCT/US2015/047180 was published under PCT Article 21(2) in English.

SEQUENCE LISTING

The instant application contains a Sequence Listing which has been submitted via EFS-Web and is hereby incorporated by reference in its entirety. Said ASCII copy, created on Feb. 27, 2017, is named 1061990033301 seq.txt, and is 24,036 bytes in size.

BACKGROUND OF THE DISCLOSURE

Malignant tumors (cancers) are the second leading cause of death in the United States, after heart disease (Boring et al., CA Cancer J. Clin. 43:7 (1993)). Cancer is an example of unwanted cell proliferation and is characterized by the increase in the number of abnormal, or neoplastic, cells derived from a normal tissue which proliferate to form a tumor mass or otherwise proliferate unchecked by proper control. Cancer may be further characterized by the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Treatments for cancer include resection, radiation therapy and chemotherapeutics. While there are numerous cancer treatments that have been approved for use in humans or that are in various stages of development, many of these treatments are associated with undesired side effects. For example, many cancer treatments do not target tumor or cancer cells specifically, and are often cytotoxic or genotoxic to healthy cells.

One class of chemotherapeutic drug frequently used for treating cancer, alone or in combination with other chemotherapeutics, is the platinum-containing anti-cancer drug class known as "platins." These drugs include cisplatin, carboplatin and oxaliplatin, which all work by binding to and causing crosslinking of DNA in a cancer cell, ultimately triggering apoptosis. However, drugs like cisplatin are associated with numerous side effects, including nephrotoxicity, neurotoxicity, nausea and vomiting, ototoxicity, electrolyte disturbance, myelotoxicity and hemolytic anemia. In addition, the majority of cancer patients administered platins will eventually relapse with cisplatin-resistant disease. While the exact mechanism for platin-resistance in cancer cells is unclear, some proposed mechanisms include changes in cellular uptake and efflux of the drug, increased detoxification of the drug, inhibition of apoptosis and increased DNA repair. Stordal et al., 2007, IUBMB Life, 59(11):696-99.

There remains a need in the art for improved methods and compositions for treating tumors and cancers.

SUMMARY OF THE DISCLOSURE

The disclosure provides various methods related to the treatment of cancers and the influence of tumor structure. The disclosure provides numerous examples of internalizing moieties that penetrate cells, such as cancer cells. These internalizing moieties include antibodies and antibody fragments, such as the antibodies and antibody fragment described herein based on numerous structureal and functional features. These include humanized antibodies having improved properties. Any such internalizing moieties, such as antibodies and antibody fragments of the disclosures, such as humanized antibodies and antibody fragments of the disclosure, can be used in any of the methods provided herein. In certain embodiments, the internalizing moiety for use in the methods described herein has one or more unique CDRs and/or has one or more improved activities relative to a murine 3E10 antibody or antibody fragment.

In some embodiments, the disclosure provides a method of treating a tumor in a subject in need thereof, comprising administering an antibody or antigen-binding fragment to the subject, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of treating a tumor in a subject in need thereof, comprising administering an antibody or antigen-binding fragment to the subject, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system. In some embodiments, the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of reducing tumor growth, proliferation or survival, comprising administering an antibody or antigen-binding fragment to the subject, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of reducing tumor growth, proliferation or survival, comprising administering an antibody or antigen-binding fragment to the subject, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system. In some embodiments, the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35; a VL CDR2 having the amino acid sequence of SEQ ID NO: 51; and a VL CDR3 having the amino acid sequence of SEQ ID NO: 37, which CDRs are according to the Kabat system. In some embodiments, the reduction in tumor growth, proliferation or survival is determined by assessing mitotic markers in a tumor sample. In some embodiments, the reduction in tumor growth, proliferation or survival is determined by assessing Ki-67 staining in a tumor sample. In some embodiments, the reduction in tumor growth, proliferation or survival is determined by CT scan or magnetic resonance imaging.

In some embodiments, the disclosure provides for a method of promoting collapse of capillary blood vessels in a tumor, comprising administering to the subject an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of promoting collapse of capillary blood vessels in a tumor, comprising administering to the subject an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system. In some embodiments, the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35; a VL CDR2 having the amino acid sequence of SEQ ID NO: 51; and a VL CDR3 having the amino acid sequence of SEQ ID NO: 37, which CDRs are according to the Kabat system. In some embodiments, the collapse of capillary blood vessels in a tumor is determined by observing CD-31 staining patterns in a tumor sample.

In some embodiments, the disclosure provides a method of triggering, promoting, inducing and/or increasing apoptosis in a subject in need thereof, such as of cancer cells in such a subject, comprising administering an internalizing moiety (e.g., an antibody or antigen binding fragment thereof of the disclosure) of the disclosure. In certain aspects, the disclosure provides a method of triggering, promoting, inducing and/or increasing apoptosis of cells of a tumor in a subject in need thereof, comprising administering an internalizing moiety (e.g., an antibody or antigen binding fragment thereof of the disclosure) of the disclosure. The disclosure provides, in certain embodiments, that such cancer or tumor is any of the cancers or tumors disclosed herein—characterized based on tissue type or mutational status. In some embodiments, the method comprises administering to the subject an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system. In some embodiments, the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35; a VL CDR2 having the amino acid sequence of SEQ ID NO: 51; and a VL CDR3 having the amino acid sequence of SEQ ID NO: 37, which CDRs are according to the Kabat system.

In some embodiments of any of the methods disclosed herein, the tumor is in a subject, and the subject is a human. In some embodiments, the tumor is in culture or in an animal. In some embodiments, the tumor is a uveal melanoma. In some embodiments, the tumor is a colorectal cancer. In some embodiments, the tumor is an ovarian cancer. In some embodiments, the tumor is pancreatic cancer. In some embodiments, the tumor is a hereditary non-polyposis colon cancer (HNPCC). In some embodiments, the tumor is an adenocarcinoma. In some embodiments, the tumor is platin-resistant. In some embodiments, the tumor is resistant to treatment with DNA repair inhibitors. In some embodiments, the tumor is associated with microsatellite instability. In some embodiments, the tumor has deficient DNA mismatch repair. In some embodiments, the tumor has a mutation in any of the hMSH2, hMSH6 or hMLH1 genes. In some embodiments, the tumor is BRCA2 proficient. In some embodiments, the tumor is BRCA2 deficient.

In some embodiments of any of the methods disclosed herein, the method comprises administering the antibody or antigen-binding fragment more than once according to a dose and dosing schedule. In some embodiments, the antibody or antigen-binding fragment thereof is administered to the subject as a monotherapy. In some embodiments, the antibody or antigen-binding fragment thereof is administered to the subject in combination with an additional therapeutic treatment. In some embodiments, the additional therapeutic treatment is a standard of care treatment appropriate for treating the subject. In some embodiments, the additional therapeutic treatment is administered concurrently with the antibody or antigen-binding fragment thereof. In some embodiments, the additional therapeutic treatment and the antibody or antigen-binding fragment thereof are administered consecutively. In some embodiments, the additional therapeutic treatment is administered prior to the administration of the antibody or antigen-binding fragment thereof.

In some embodiments of any of the methods disclosed herein, the therapeutically effective amount of each of: a) the antibody or antigen binding fragment, and/or b) the additional therapeutic treatment is less than that required to achieve a therapeutic effect when one or both agents is administered as a monotherapy. In some embodiments, the additional therapeutic treatment causes DNA damage in a cancer or tumor cell. In some embodiments, the additional therapeutic treatment is radiotherapy. In some embodiments, the additional therapeutic treatment is chemotherapy. In some embodiments, the chemotherapy comprises administering to the subject a DNA-damaging compound, wherein the compound is a DNA cross-linker. In some embodiments, the DNA cross-linker is a platin. In some embodiments, the platin is cisplatin, carboplatin or oxaliplatin, or an active analog thereof. In some embodiments, the chemotherapy comprises administering to the subject a DNA-damaging compound, wherein the compound is an inhibitor of DNA synthesis. In some embodiments, the inhibitor of DNA synthesis is methotrexate, or an active analog thereof. In some embodiments, the chemotherapy comprises administering to the subject a DNA-damaging compound, wherein the compound is a topoisomerase poison. In some embodiments, the topoisomerase poison is doxorubicin or daunorubicin, or an active analog thereof. In some embodiments, the chemotherapy comprises administering to the subject a DNA-damaging compound, wherein the compound is a DNA-alkylating agent. In some embodiments, the DNA-alkylating agent is a nitrosourea or triazene compound. In some embodiments, the chemotherapy comprises administering to the subject a DNA-damaging compound, wherein the compound is an antimetabolite. In some embodiments, the antimetabolite is a pyrimidine analog.

In some embodiments of any of the methods disclosed herein, the antibody or antigen-binding fragment is administered to the subject intravenously. In some embodiments, the antibody or antigen-binding fragment is administered to the subject intramuscularly. In some embodiments, the antibody or antigen-binding fragment is administered to the subject subcutaneously.

In some embodiments, the disclosure provides for a method of inhibiting proliferation of a cancerous cell or tumor cell, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of inhibiting proliferation of a cancerous cell or tumor cell, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of decreasing Ki-67 expression in a tumor, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of decreasing Ki-67 expression in a tumor, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of decreasing CD-31 expression in a tumor, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 1; a VH CDR2 having the amino acid sequence of SEQ ID NO: 2; and a VH CDR3 having the amino acid sequence of SEQ ID NO: 3, which CDRs are according to the IMGT system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the disclosure provides for a method of decreasing CD-31 expression in a tumor, comprising contacting the tumor cell with an antibody or antigen-binding fragment, wherein the antibody or antigen-binding fragment comprises a light chain variable (VL) domain and a heavy chain variable (VH) domain; wherein the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37, which CDRs are according to the Kabat system.

In some embodiments, the VH domain comprises: a VH CDR1 having the amino acid sequence of SEQ ID NO: 32; a VH CDR2 having the amino acid sequence of SEQ ID NO: 49; and a VH CDR3 having the amino acid sequence of SEQ ID NO: 34, which CDRs are according to the Kabat system; and the VL comprises: a VL CDR1 having the amino acid sequence of SEQ ID NO: 35; a VL CDR2 having the amino acid sequence of SEQ ID NO: 51; and a VL CDR3 having the amino acid sequence of SEQ ID NO: 37, which CDRs are according to the Kabat system.

In some embodiments of any of the methods disclosed herein, the tumor is in a subject. In some embodiments, the subject is a human.

In some embodiments of any of the methods disclosed herein, the antibody or antigen-binding fragment is a full length antibody or comprises a portion of an Fc domain, and which antibody or antigen-binding fragment is effective at a lower dose than a murine 3E10 full length antibody. In some embodiments, the antibody or antigen-binding fragment is a Fab or Fab', and which antibody or antigen-binding fragment is effective at a lower dose than a murine 3E10 Fv or scFv. In some embodiments, the antibody or antigen-binding fragment is an scFv. In some embodiments, the antibody or antigen-binding fragment is a Fab'. In some embodiments, the antibody or antigen-binding fragment is a a F(ab')2 fragment, and which antibody or antigen-binding fragment is effective at a lower dose than a murine a F(ab')2 fragment. In some embodiments, the internalizing moiety is a full length antibody comprising a heavy chain constant domain and a light chain constant domain. In some embodiments, the heavy chain comprises a constant domain comprising a CH1, hinge, CH2 and, optionally a CH3 domain. In some embodiments, the heavy chain is chimeric and comprises an IgG1 portion and IgG2a portion. In some embodiments, the antibody has been modified such that it does not induce antibody-dependent cell-mediated cytotoxicity (ADCC). In some embodiments, the CH2 domain comprises an N to Q substitution at a position corresponding to Kabat position 297. In some embodiments, the antibody or antigen-binding fragment is not conjugated or otherwise interconnected to another therapeutic agent. In some embodiments, the antibody or antigen-binding fragment is conjugated or interconnected to another therapeutic agent. In some embodiments, the chimeric polypeptide further comprises one or more polypeptide portions that enhance one or more of in vivo stability, in vivo half life, uptake/administration, production, or purification. In some embodiments, the internalizing moiety comprises an antibody or antigen binding fragment that can transit a cellular membrane via an equilibrative nucleoside transporter 2 (ENT2) transporter and/or binds DNA with a $K_D$ of less than 100 nM. In some embodiments, the VH domain is humanized. In some embodiments, the VL domain is humanized. In some embodiments, the $V_H$ domain comprises one or more of the following amino acid alterations: V5Q, L11V, K13Q, R18L, K19R, V37I, E42G, A49S, T63S, A75S, F80Y, T84N, M93V, T111L or L112V, as compared with and numbered with respect to the amino acid sequence of SEQ ID NO: 9. In some embodiments, the $V_L$ domain comprises one or more of the following amino acid alterations: V3Q, L4M, A9S, A12S, V13A, L15V, Q17D, A19V, G45E, Q46K, P47A, E59Q, A64S, H76T, N78T, H80S, P81S, V82L, E83Q, E84P, A87V, or G104A, as compared with and numbered with respect to the amino acid sequence of SEQ ID NO: 7. In some embodiments, the $V_L$ domain comprises at least 5, at least 6, at least 7, at least 8, at least 9, at least 10, at least 11, at least 12, at least 13, at least 14, at least 15, at least 16, at least 17, or at least 18 of said amino acid alterations, as compared with and numbered with respect to the amino acid sequence of SEQ ID NO: 7. In some embodiments, the $V_H$ domain comprises at least 5, at least 6, at least 7, at least 8, at least 9, or at least 10 of said amino acid alterations, as compared with and numbered with respect to the amino acid sequence of SEQ ID NO: 9. In some embodiments, the VL comprises the amino acid sequence set forth in SEQ ID NO: 8. In some embodiments, the VH comprises the amino acid sequence set forth in SEQ ID NO: 10. In some embodiments, the VL comprises the amino acid sequence set forth in SEQ ID NO: 8, and the VH comprises the amino acid sequence set forth in SEQ ID NO: 10. In some embodiments, the antibody or antigen-binding fragment is an anti-DNA antibody. In some embodiments, the antibody or antigen-binding fragment is capable of transiting cell membranes via an ENT receptor. In some embodiments, the antibody or antigen-binding fragment thereof is capable of binding DNA bubbles. In some embodiments, the antibody or antigen-binding fragment thereof is capable of binding T-rich bubbles. In some embodiments, the antibody or antigen-binding fragment binds DNA bubbles or T-rich bubbles with higher affinity than to single stranded DNA tails. In some embodiments, the antibody or antigen-binding fragment binds DNA response elements. In some embodiments, the antibody or antigen-binding fragment binds DNA response elements to prevent transcription proteins from binding to the elements. In some embodiments, the antibody or antigen-binding fragment is cytotoxic to tumor cells. In some embodiments, the antibody or antigen-binding fragment is not cytotoxic to non-tumor cells. In some embodiments, the antibody or antigen-binding fragment induces apoptosis in tumor cells.

The disclosure contemplates all combinations of any of the foregoing aspects and embodiments, as well as combinations with any of the embodiments set forth in the detailed description and examples.

BRIEF DESCRIPTION OF THE DRAWINGS

FIGS. 1A-1H are bar graphs illustrating the effects of a humanized antibody (3E10 Mab) of the disclosure, alone or in combination with alpha-amanitin or ABT-888, on cell viability of CAPAN-1 (FIG. 1A), SW837 (FIG. 1B), HT29 (FIG. 1C) SW480 (FIG. 1D), BRCA2 deficient DLD-1 (FIGS. 1E & 1F—duplicate experiments) and BRCA2 proficient DLD-1 (FIGS. 1G & 1H—duplicate experiments) cancer cells. Viability was measured by counting the number of live cells per well. FIGS. 1A-1H show percent live cells as compared to the buffer treated cells.

FIG. 9A illustrates the results from this multi-study analysis in terms of tumor growth percent inhibition as compared to untreated controls. The bars labeled HT29-1 and HT29-2 reflect results from two different xenograft mouse studies using the same HT29 cell line. FIG. 9B displays results of an ANOVA statistical analysis of the multi-study tumor growth data. FIG. 9B illustrates the results in terms of average percent growth of tumors in all 3E10 Mab antibody treated and vehicle control treated xenograft mice. Treatment with the antibody resulted in a greater than 43% reduction in tumor growth ($p<0.0039$). In addition, the omega squared value for the combined effect of the antibody or vehicle on tumor growth in all xenograft mice tested was 0.16 (i.e., only 16% of variability in tumor growth can be due to treatment effect differences across the various cancer cell lines).

FIG. 10 provides a sequence alignment of representative humanized heavy chain variable domains (HH1, HH2, and HH3) as compared to each other and the murine, parent 3E10 heavy chain variable domain (MH1) (See top half of FIG. 10), and also provides a sequence alignment of representative humanized light chain variable domains (HL1 and HL2) as compared to each other and the murine, parent 3E10 light chain variable domain (ML1). The CDRs, as determined in accordance with the Kabat Sequences of Proteins of Immunological Interest (1987 and 1991, National Institutes of Health, Bethesda, Md.) or in accordance with the IMGT system (LeFranc et al., 2003, Development and Comparative Immunology, 27: 55-77 and IMGT/V-QUEST database), are underlined by a black bar (Kabat) or higlighted in dark gray (IMGT), while changes in the humanized heavy or light chain variable domain sequences, as compared to the respective murine 3E10 parent chain are highlighted in light gray. Amino acid changes introduced to improve folding of a humanized heavy chain are in bold and in lowercase. The sequence identifiers for the amino acid sequence of each of the different antibody chains indicated are as follows: ML1=SEQ ID NO: 7; MH1=SEQ ID NO: 9; HH1=SEQ ID NO: 38; HH2=SEQ ID NO: 39; HH3=SEQ ID NO: 10; HL1=SEQ ID NO: 40; HL2=SEQ ID NO: 8.

DETAILED DESCRIPTION OF THE DISCLOSURE

Figure 1A:
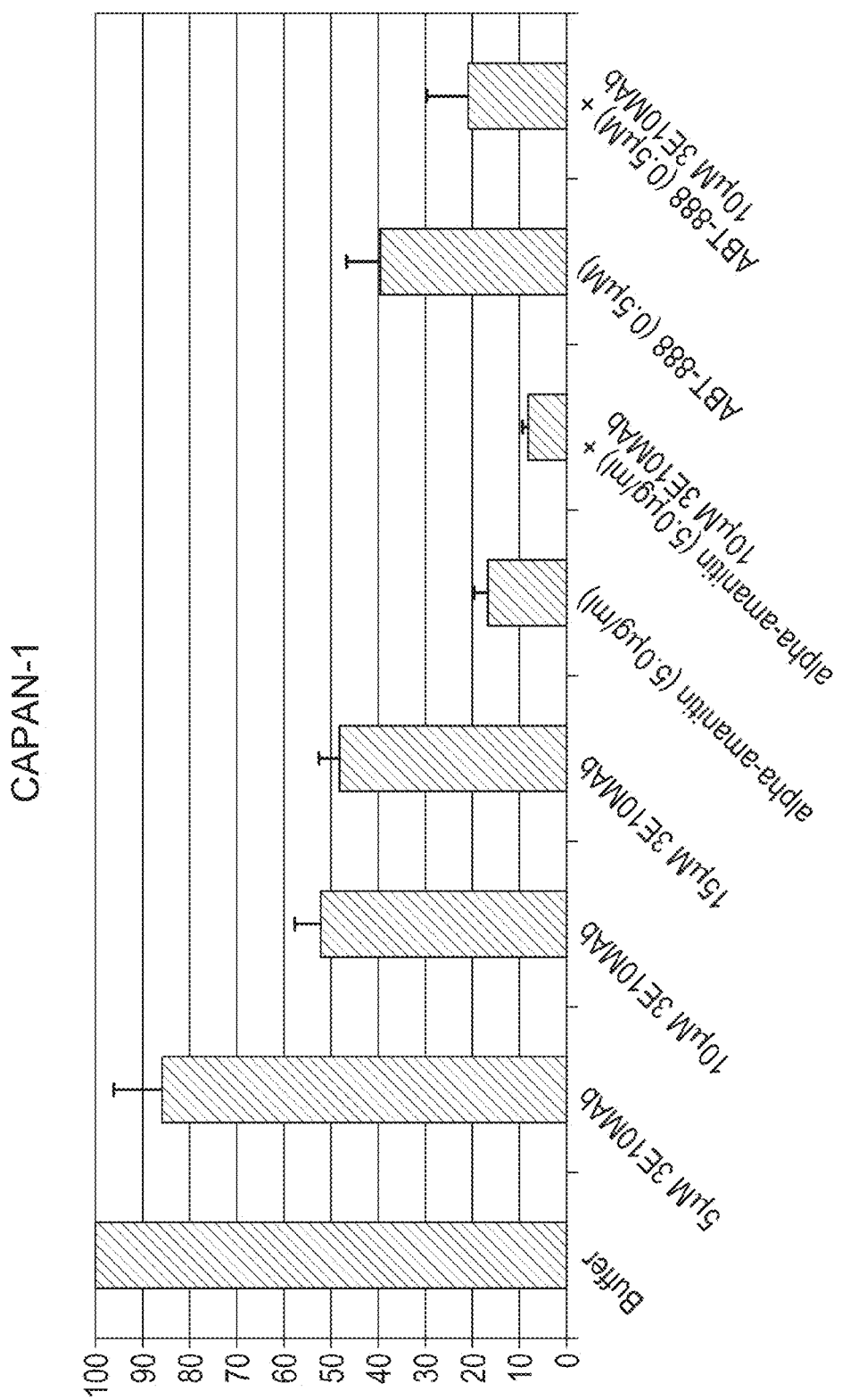
Figure 1B:
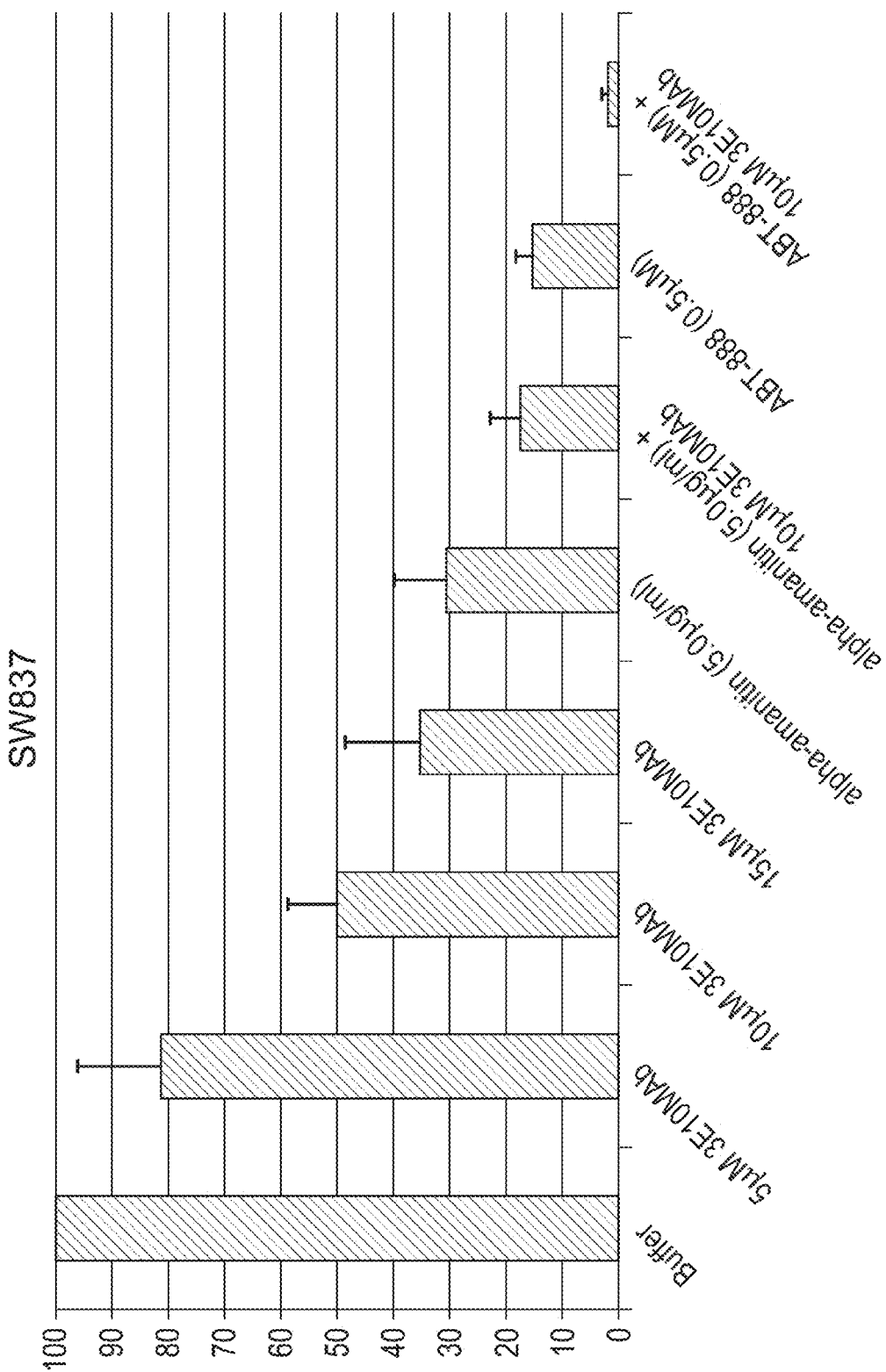
Figure 1C:
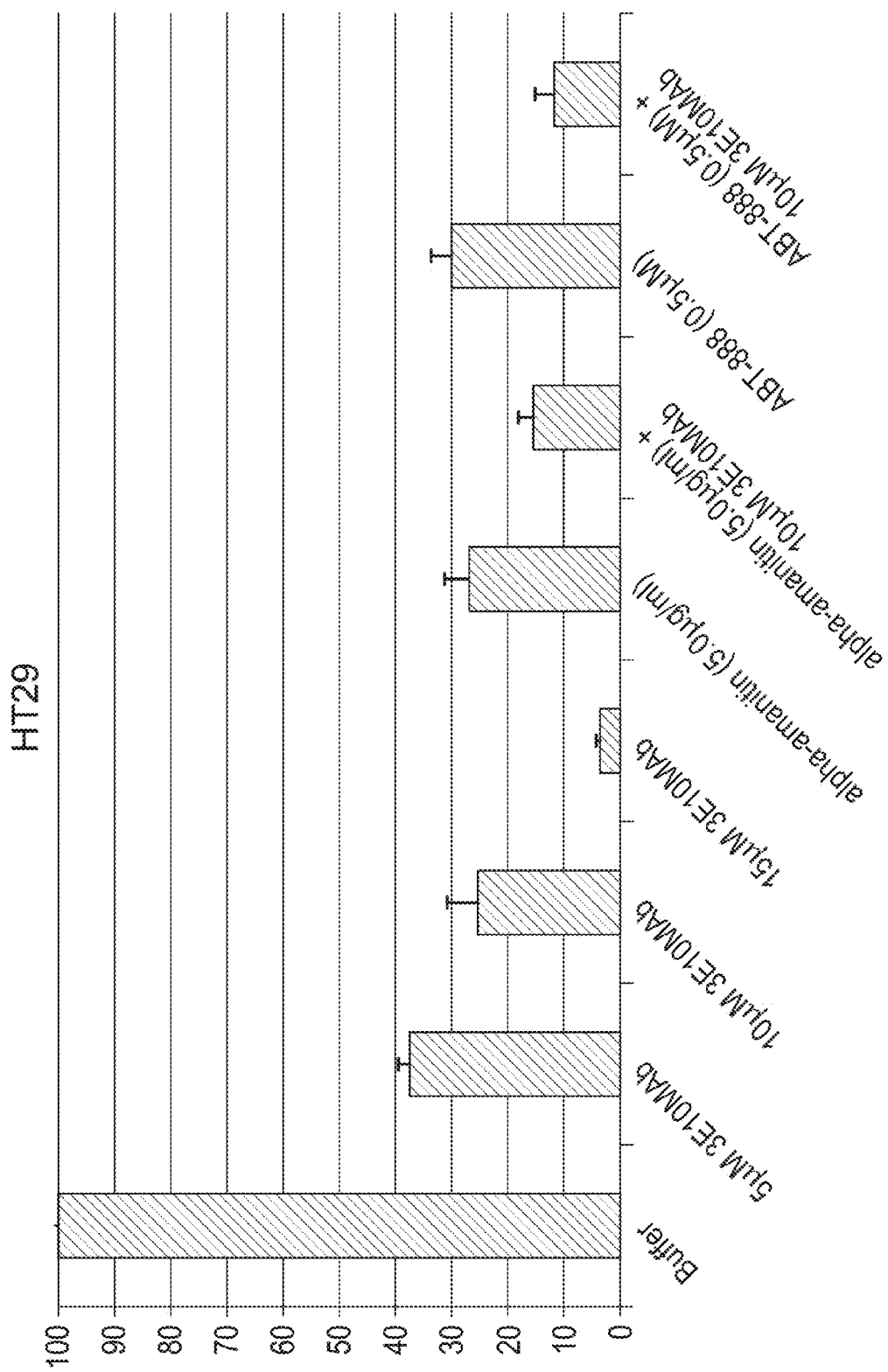
Figure 1E:
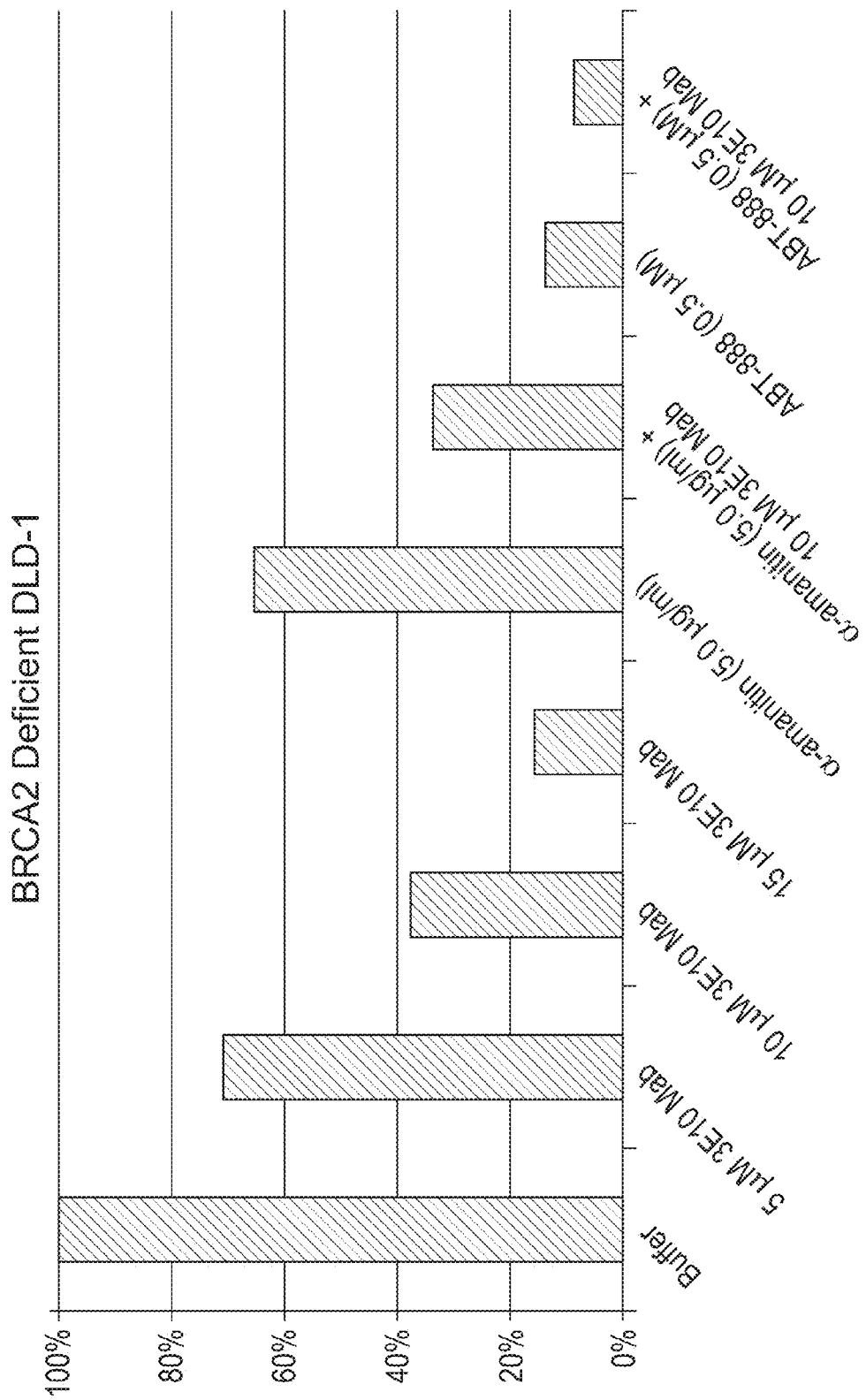
Figure 1F:
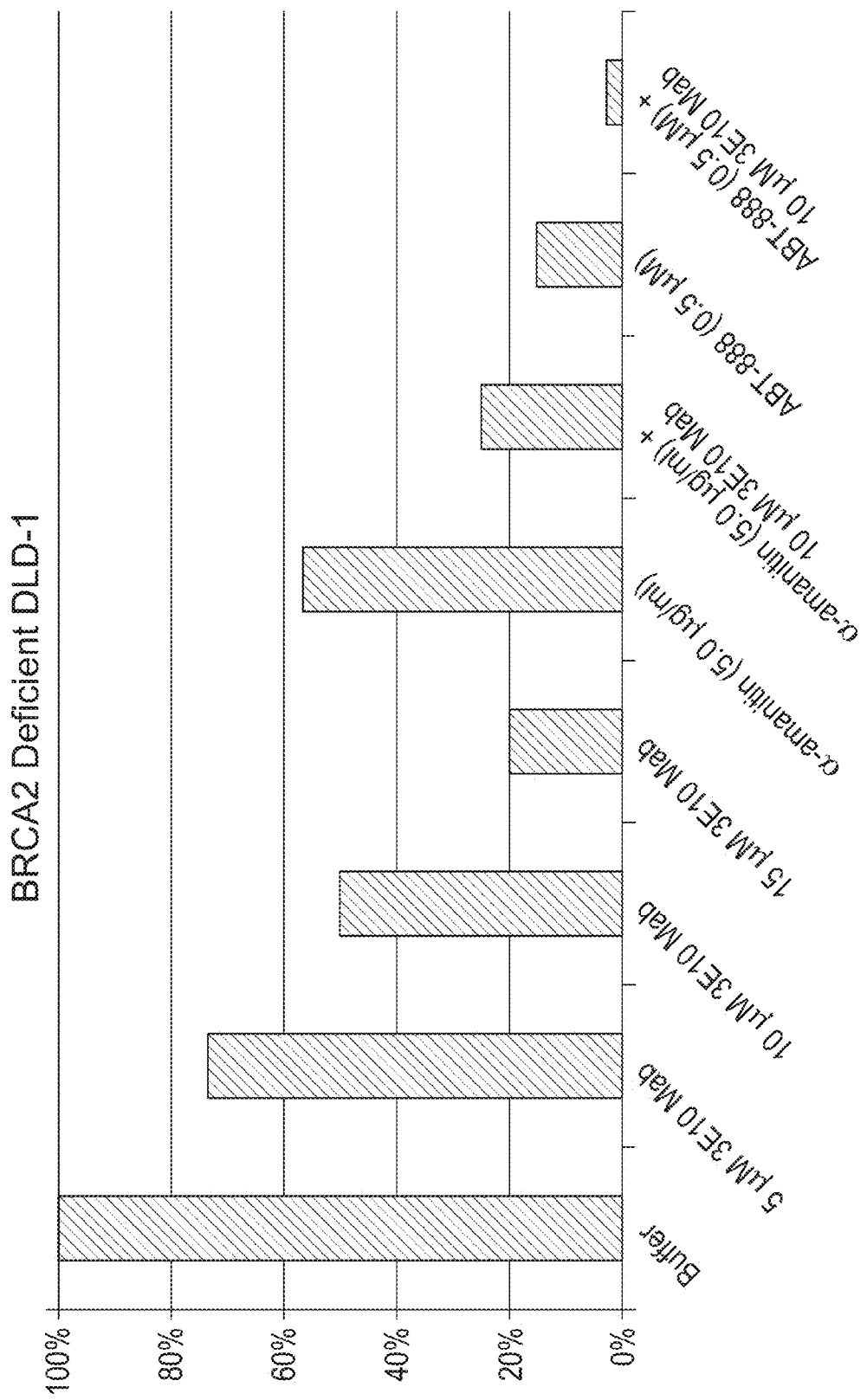
Figure 1G:
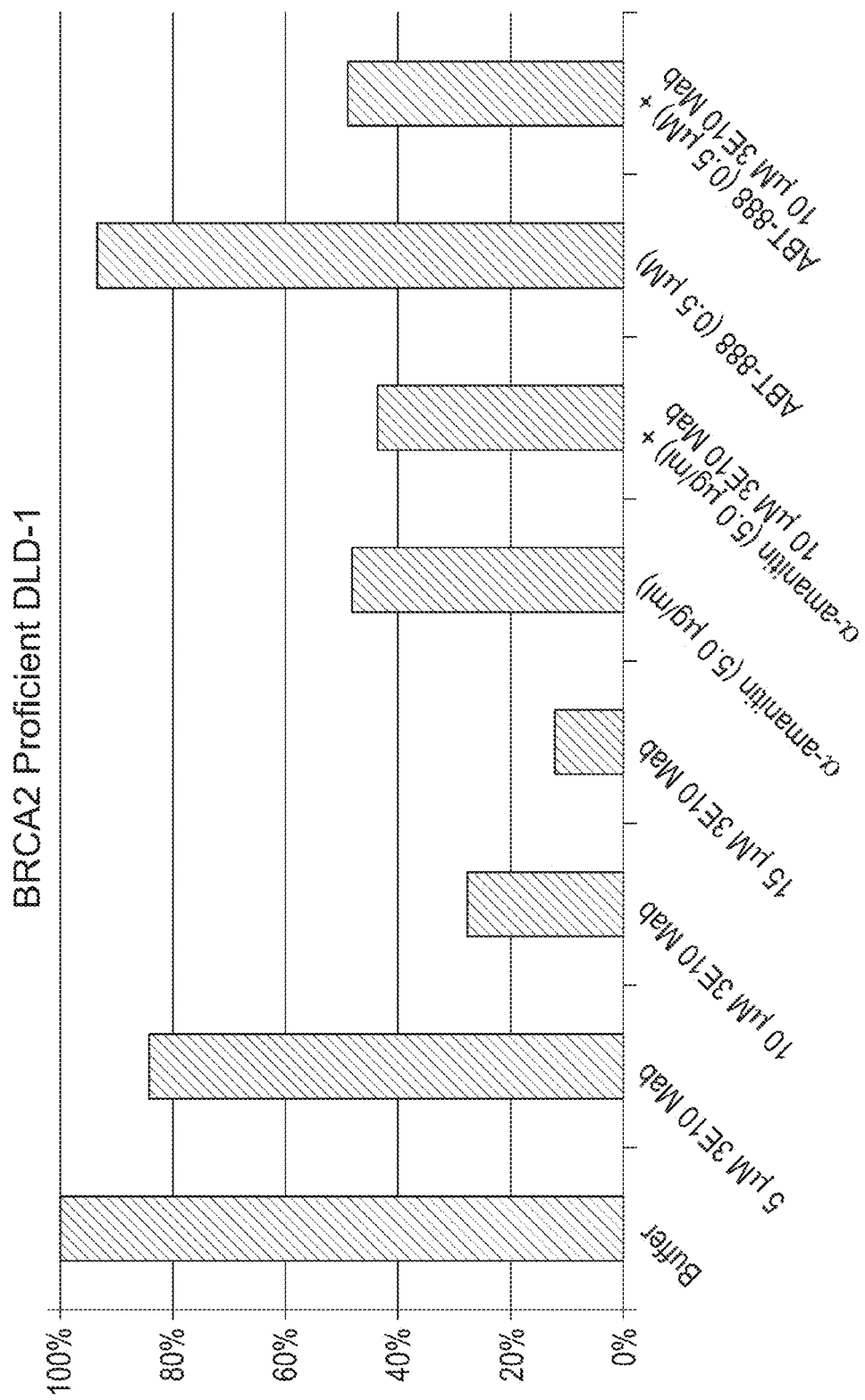
Figure 1H:
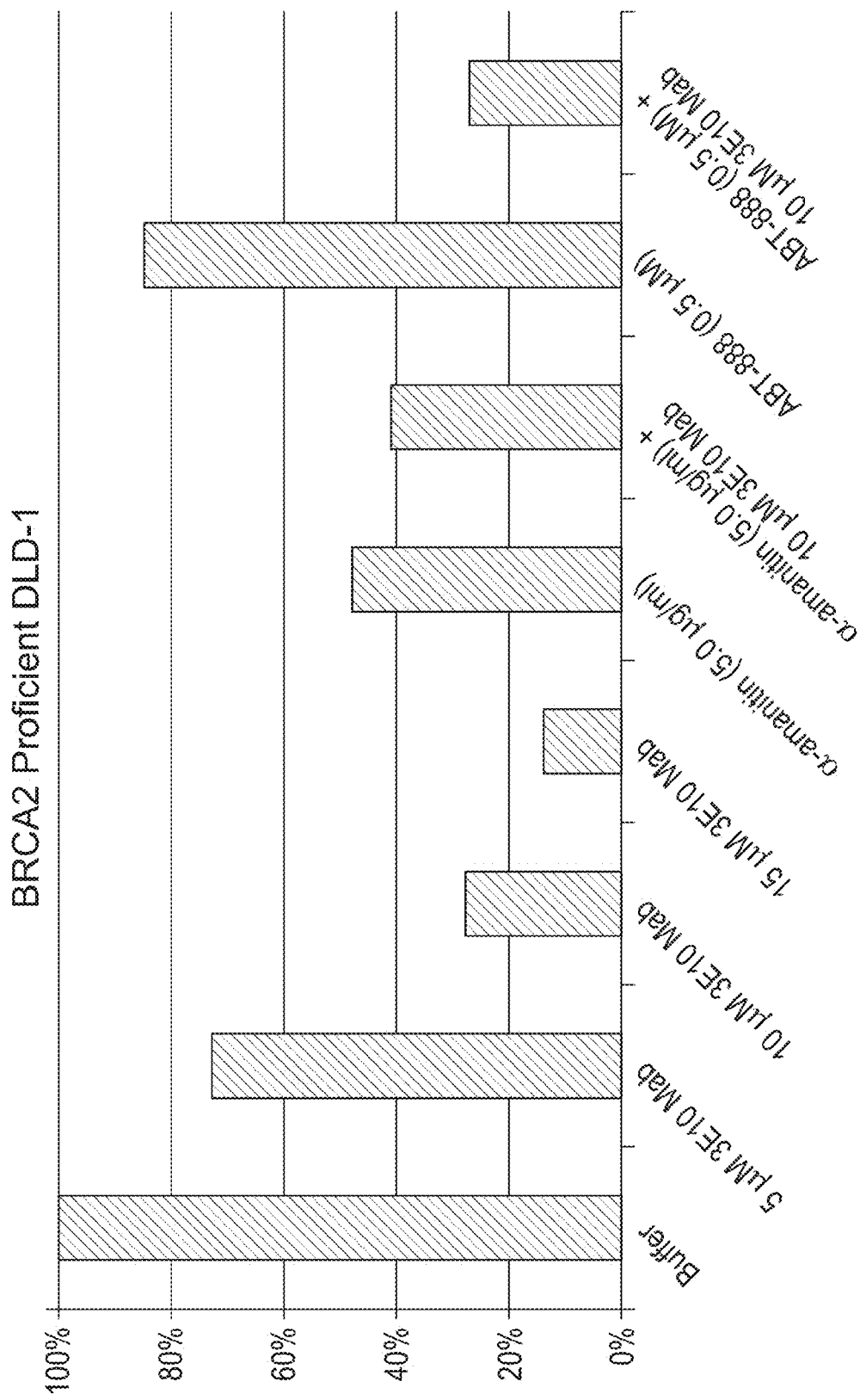

The disclosure provides antibodies and antigen-binding fragments for use in any of the methods described herein. In certain embodiments, the antibodies or antigen-binding fragments are for use in treating a subject having a tumor and/or cancer. In some embodiments, the antibodies or antigen-binding fragments are for use in reducing tumor growth, proliferation or survival in a subject. In some embodiments, the antibodies or antigen-binding fragments are for use in inhibiting proliferation of a tumor cell or of cancerous cells. In some embodiments, the antibodies or antigen-binding fragments are for use in promoting collapse of tumor capillary blood vessels in a tumor in a subject. In some embodiments, the antibodies or antigen-binding fragments are for use in altering tumor or stromal architecture, such as by changing endothelial expression and/or blood vessel architecture.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Each embodiment of the disclosure described herein may be taken alone or in combination with one or more other embodiments of the disclosure.

Throughout this specification, the word "comprise" or variations such as "comprises" or "comprising" will be understood to imply the inclusion of a stated integer or groups of integers but not the exclusion of any other integer or group of integers.

Throughout this specification, the word "a" will be understood to imply the inclusion of one or more of the integers modified by the article "a."

By the terms "has the ability" or "is capable of" is meant that the recited proteins or polypeptides will carry out the stated bioactivity under suitable conditions (e.g., physiological conditions or standard laboratory conditions). In certain embodiments, the term "can" may be used to describe this ability (e.g., "can bind" or "binds" to a given sequence).

I. Internalizing Moiety

As used herein, the term "internalizing moiety" refers to a polypeptide/protein capable of interacting with a target tissue or a cell type such that the moiety is internalized into the target tissue or the cell type.

As used herein, "antibodies or antigen binding fragments of the disclosure" refer to any one or more of the antibodies and antigen binding fragments provided herein.

Antibodies and antigen binding fragments of the disclosure comprise a heavy chain comprising a heavy chain variable domain and a light chain comprising a light chain variable domain. A $V_H$ domain comprises three CDRs, such as any of the CDRs provided herein and as defined or identified by the Kabat and/or IMGT systems. These CDRs are typically interspersed with framework regions (FR), and together comprise the $V_H$ domain. Similarly, a VL comprises three CDRs, such as any of the CDRs provided herein and as defined by the Kabat and/or IMGT systems. These CDRs are typically interspersed with framework regions (FR), and together comprise the $V_L$ domain. The FR regions, such as FR1, FR2, FR3, and/or FR4 can similarly be defined or identified by the Kabat or IMGT systems. Throughout the application, when CDRs are indicated as being, as identified or defined by the Kabat or IMGT systems, what is meant is that the CDRs are in accordance with that system (e.g., the Kabat CDRs or the IMGT CDRs). Any of these terms can be used to indicate whether the Kabat or IMGT CDRs are being referred to.

The disclosure contemplates that an antibody or antigen binding fragment may comprise any combination of a $V_H$ domain, as provided herein, and a $V_L$ domain, as provided herein. In certain embodiments, at least one of the $V_H$ and/or $V_L$ domains are humanized (collectively, antibodies or antigen binding fragments of the disclosure). Chimeric antibodies are also included. Any antibody or antigen binding fragment of the disclosure may be provided alone. In other embodiments, any antibody or antigen binding fragment of the disclosure may be provided as a conjugate associated with a heterologous agent. Non-limiting examples of heterologous agents, which may include polypeptides, peptides, small molecules (e.g., a chemotherapeutic agent small molecule), or polynucleotides, are provided herein. Conjugates may refer to an antibody or antigen binding fragment associated with a heterologous agent.

In some embodiments, the antibody or antigen-binding fragment is isolated and/or purified. Any of the antibodies or antigen-binding fragments described herein, including those provided in an isolated or purified form, may be provided as a composition, such as a composition comprising an antibody or antigen-binding fragment formulated with one or more pharmaceutical and/or physiological acceptable carriers and/or excipients. Any of the antibodies or antigen-binding fragments described herein, including compositions (e.g., pharmaceutical compositions) may be used in any of the methods described herein and may be optionally provided conjugated (e.g., interconnected; associated) with a heterologous agent. In some embodiments, the internalizing moiety is capable of interacting with a target tissue or a cell type to effect delivery of the heterologous agent into a cell (i.e., penetrate desired cell; transport across a cellular membrane; deliver across cellular membranes to, at least, the cytoplasm). Such conjugates may similarly be provided as a composition and may be used in any of the methods described herein.

Internalizing moieties having limited cross-reactivity are generally preferred. In certain embodiments, this disclosure relates to an internalizing moiety which selectively, although not necessarily exclusively, targets and penetrates cancer cells. In certain embodiments, the internalizing moiety has limited cross-reactivity, and thus preferentially targets a particular cell or tissue type. However, it should be understood that internalizing moieties of the subject disclosure do not exclusively target specific cell types and do not exclusively target cancer cells. Rather, the internalizing moieties promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof. In certain embodiments, the internalizing moiety mediates transit across cellular membranes via an ENT2 transporter. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits cellular membranes via an equilibrative nucleoside transporter 2 (ENT2) and/or ENT3 transporter. In some embodiments, the internalizing moiety promotes delivery into cancer cells (e.g., platin-resistant cancer cells). For any of the foregoing, in certain embodiments, the internalizing moiety is internalized into the cytoplasm. In certain embodiments, the internalizing moiety is internalized into the nucleus.

In certain embodiments, the internalizing moiety is an antibody or antibody fragment that binds DNA. In certain embodiments, the internalizing moiety is any of the antibody or antibody fragments described herein. In other words, in certain embodiments, the antibody or antibody fragment (e.g., antibody fragment comprising an antigen binding fragment) binds DNA. In certain embodiments, DNA binding ability is measured versus a double stranded DNA substrate. In certain embodiments, the internalizing moiety is an antibody or antibody fragment that binds DNA and can transit cellular membranes via ENT2. In certain embodiments, the internalizing moiety binds a DNA bubble.

In certain embodiments, the internalizing moiety is capable of binding polynucleotides. In certain embodiments, the internalizing moiety is capable of binding DNA. In certain embodiments, the internalizing moiety is an antibody capable of binding DNA. In certain embodiments, the internalizing moiety is capable of binding DNA with a $K_D$ of less than 1 µM. In certain embodiments, the internalizing moiety is capable of binding DNA with a $K_D$ of less than 100 nM, less than 75 nM, less than 50 nM, or even less than 30 nM. $K_D$ can be measured using Surface Plasmon Resonance (SPR) or Quartz Crystal Microbalance (QCM), in accordance with currently standard methods. By way of example, a 3E10 antibody or antibody fragment, including an antibody or antibody fragment comprising a VH having the amino acid sequence set forth in SEQ ID NO: 8 and a VL having an amino acid sequence set forth in SEQ ID NO: 10 is known to bind DNA with a $K_D$ of less than 100 nM. Thus, in certain embodiments, an internalizing moiety for use in the chimeric polypeptides of the disclosure is an antibody or antibody fragment (e.g., an antigen binding fragment) that can transit cellular membranes into the cytoplasm and binds to DNA. This is also exemplary of an anti-DNA antibody. In certain embodiments, an internalizing moiety for use herein is an anti-DNA antibody or antigen binding fragment thereof. In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In fact, a full length antibody comprising the foregoing VH and VL binds a double-stranded blunt DNA substrate with an even lower $K_D$, as evaluated by ELISA. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed. 3004385), such as by ELISA, QCM, or Biacore. In certain embodiments, the foregoing $K_D$ of the antibody or antibody fragment (such as an antibody fragment comprising an antigen-binding fragment) is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3' (SEQ ID NO: 18)). In certain embodiments, the internalizing moiety is an anti-DNA antibody. It is recognized that 3E10 and other anti-DNA antibodies may be capable of binding a variety of DNA substrates with high affinity, as has been demonstrated.

In some embodiments, any of the internalizing moieties described herein, such as any of the antibodies or antigen-binding fragments of the disclosure, is capable of binding specific nucleotide motifs present in a polynucleotide sequence. In some embodiments, the internalizing moiety is capable of binding AT-rich sequences. In some embodiments, the internalizing moiety binds to AT-rich sequences with a stronger affinity than to a GC-rich sequence. In some embodiments, the internalizing moiety is capable of binding a TATA sequence. In some embodiments, the internalizing moiety binds to 4-mer TATA motifs within a 6 base pair sequence. In some embodiments, the internalizing moiety is capable of binding a DNA bubble. In some embodiments, the internalizing moiety is capable of binding a DNA sequence adjacent to a DNA bubble. In some embodiments, the internalizing moiety is capable of binding a DNA sequence adjacent to a DNA bubble that is at least 3, 4, 5, 6, 7, 8, 9, 10, 11, 12, 13, 14, 15, 16, 17, 18, 19, 20, 21, 22, 23, 24, or at least 25 base pairs in length. In some embodiments, the internalizing moiety is capable of binding a 5-mer variable region adjacent to a 7-base or 11-base bubble. In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In some embodiments, the internalizing moiety is capable of binding T-rich DNA bubbles. In some embodiments, the internalizing moiety is capable of binding T-rich bubbles that are at least 3, 4, 5, 6, 7, 8, 9, 10, 11, 12, 13, 14, 15, 16, 17, 18, 19, 20, 21, 22, 23, 24, or at least 25 base pairs in length. In some embodiments, the internalizing moiety is capable of binding T-rich bubbles that are at least 15, at least 20 or at least 25 base pairs in length. In some embodiments, the internalizing moiety binds to a T-rich bubble having at least 15, at least 20 or at least 25 base pairs in length with a stronger affinity than to a T-rich bubble having less than 15, less than 12, or less than 10 base pairs in length. In some embodiments, the internalizing moiety binds to a T-rich bubble having 5, 6, or 7 or more with a stronger affinity than to a T-rich bubble having four or less thymines. In some embodiments, the internalizing moiety binds to a T-rich bubble in double-stranded DNA. In other embodiments, the internalizing moiety binds to a T-rich bubble in single-stranded DNA. In some embodiments, the internalizing moiety is capable of binding DNA at a stalled transcription site. In some embodiments, the internalizing moiety is capable of binding to a T-rich bubble at a stalled transcription site. In some embodiments, the internalizing moiety is capable of binding DNA at a DNA repair site. In some embodiments, the internalizing moiety is capable of binding to a T-rich bubble at a DNA repair site. In some embodiments, the internalizing moiety is capable of binding a Fox-motif. In certain embodiments, the Fox-motif comprises the consensus of TRTTKRY (SEQ ID NO: 52), wherein R=A/G, Y=C/T, and K=T/G. In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In certain embodiments, the Fox motif comprises the sequence of 5'-GTAAACAA-3' (SEQ ID NO: 14). In some embodiments, the internalizing moiety is capable of binding nucleotide sequences comprising the nucleotide sequences of SEQ ID NOs: 19-23 (12-mers), SEQ ID NOs: 24-26 (FoxA1 probes) and SEQ ID NO: 27 (T-rich bubble). In some embodiments, the internalizing moiety binds a nucleotide sequence comprising any one of the nucleotides sequences of SEQ ID NOs: 11 and 44 (12-mers) and SEQ ID NOs: 24, 25 and 46 (FoxA1 probes) with a weaker binding affinity than the binding affinity of the same internalizing moiety for a polynucleotide sequence comprising any of the following nucleotides sequences: SEQ ID NOs: 19-23 (12-mers), SEQ ID NOs: 24-26 (FoxA1 probes). In some embodiments, the internalizing moiety binds a nucleotide sequence comprising any one of the nucleotides sequences of SEQ ID NOs: 11 and 44 (12-mers) and SEQ ID NOs: 24, 25 and 46 (FoxA1 probes) with a binding affinity that is at least an order of magnitude weaker than the binding affinity of the same internalizing moiety for a polynucleotide sequence comprising any of the following nucleotides sequences: SEQ ID NOs: 19-23 (12-mers), SEQ ID NOs: 24-26 (FoxA1 probes). In some embodiments, the internalizing moiety binds with stronger affinity to a flexible polynucleotide sequence as opposed to a rigid polynucleotide sequence.

In some embodiments, any of the internalizing moieties described herein bind DNA at DNA response elements. In some embodiments, the internalizing moieties bind DNA response elements to prevent transcription factors or proteins from binding to the elements. In some embodiments, the internalizing moieties block or inhibit transcription.

In certain aspects, any of the internalizing moieties described herein bind DNA at DNA repair sites. In some embodiments, the internalizing moiety binds a DNA bubble formed at a DNA repair site. In some embodiments, the internalizing moiety binds DNA at a DNA repair site, wherein the DNA repair site is present as the result of DNA damage due to chemotherapeutic or radiotherapeutic treatment. In some embodiments, the internalizing moiety binds DNA at a DNA repair site wherein the DNA repair site is present as the result of DNA damage due to chemotherapeutic treatment. In some embodiments, the chemotherapeutic treatment is treatment with a DNA cross-linker (e.g., a platin such as cisplatin, carboplatin, oxaliplatin or an active analog thereof), an inhibitor of DNA synthesis (e.g., methotrexate or an active analog thereof), a topoisomerase poison (e.g., doxorubicin, daunorubicin, or an active analog thereof), a DNA alkylating agent (e.g., a nitrosurea, triazene compound or an active analog thereof), and/or an antimetabolite (e.g., a pyrimidine analog such as 5-fluorouracil or an active analog thereof).

In some embodiments, any of the internalizing moieties of the disclosure are capable of binding DNA at DNA sites independent of DNA repair sites. In some embodiments, the internalizing moieties are capable of binding DNA in a tumor or cancer cell in which DNA repair cannot be inhibited (e.g., such as a cell defective in one or more components of the DNA repair machinery). In some embodiments, the internalizing moieties are capable of binding DNA in a tumor or cancer cell in which mismatch repair cannot be inhibited.

In certain aspects, an internalizing moiety may comprise an antibody, including a monoclonal antibody, a polyclonal antibody, and a humanized antibody. Without being bound by theory, such antibody may bind preferentially to a cancer cell. In some embodiments, the internalizing moiety is a full-length antibody. In some embodiments, internalizing moieties may comprise antibody fragments, derivatives or analogs thereof, including without limitation: antibody fragments comprising antigen binding fragments (e.g., Fv fragments, single chain Fv (scFv) fragments, Fab' fragments, F(ab')2 fragments), single domain antibodies, camelized antibodies and antibody fragments, humanized antibodies and antibody fragments, human antibodies and antibody fragments, and multivalent versions of the foregoing; multivalent internalizing moieties including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In some embodiments, the antibodies or variants thereof may be chimeric, e.g., they may include variable heavy or light regions from the murine 3E10 antibody, but may include constant regions from an antibody of another species (e.g., a human). In some embodiments, the antibodies or variants thereof may comprise a constant region that is a hybrid of several different antibody subclass constant domains (e.g., any combination of IgG1, IgG2a, IgG2b, IgG3 and IgG4, from any species or combination of species). In some embodiments, the antibodies or variants thereof (e.g., the internalizing moiety) comprise the following constant domain scheme: IgG2a CH1-IgG1 hinge-IgG1 CH2-CH3, for example, any of the foregoing may be human IgG or murine IgG. Other suitable combinations are also contemplated. In other embodiments, the antibody comprises a full length antibody and the CH1, hinge, CH2, and CH3 is from the same constant domain subclass (e.g., IgG1). In some embodiments, the antibodies or variants thereof are antibody fragments (e.g., the internalizing moiety is an antibody fragment comprising an antigen binding fragment; e.g., the internalizing moiety is an antigen binding fragment) comprising a portion of the constant domain of an immunoglobulin, for example, the following constant domain scheme: IgG2a CH1-IgG1 upper hinge. In some embodiments, the antibodies or variants thereof comprise a kappa constant domain (e.g., SEQ ID NO: 15). Heavy chain constant domains (whether for a full length antibody or for an antibody fragment (e.g., an antigen binding fragment) comprising an amino acid substitution, relative to native IgG domains, to decrease effector function and/or facilitate production are included within the scope of antibodies and antigen binding fragments. For example, one, two, three, or four amino acid substitutions in a heavy chain, relative to a native murine or human immunoglobulin constant region, such as in the hinge or CH2 domain of a heavy chain constant region.

In certain embodiments, an internalizing moiety comprises an antibody, and the heavy chain comprises a VH region, and a constant domain comprising a CH1, hinge, CH2, and CH3 domain. In certain embodiments, a heavy chain comprises a VH region, and a constant domain comprising a CH1 domain and, optionally, the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In some embodiments, the internalizing moiety comprises all or a portion of the Fc region of an immunoglobulin. In other words, in addition to an antigen binding portion, in certain embodiments, the internalizing moiety comprises all or a portion of a heavy chain constant region of an immunoglobulin (e.g., one or two polypeptide chains of a heavy chain constant region. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region, or a portion of a hinger (e.g., an upper hinge). In certain embodiments, an internalizing moiety further comprises a light chain constant region (CL).

In some embodiments, the Fc portion of any of the internalizing moieties described herein has been modified such that it does not induce antibody-dependent cell-mediated cytotoxicity (ADCC). In some embodiments, the Fc portion has been modified such that it does not bind complement. In certain embodiments, a CH2 domain of the Fc portion comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In some embodiments, the internalizing moiety is any peptide or antibody-like protein having the complementarity determining regions (CDRs) of the 3E10 antibody sequence, or of an antibody that binds the same epitope (e.g., the same target, such as DNA) as 3E10. Also, transgenic mice, or other mammals, may be used to express humanized or human antibodies. Such humanization may be partial or complete.

In certain embodiments, the internalizing moiety comprises the monoclonal antibody 3E10 or an antigen binding fragment thereof. In other embodiments, the internalizing moiety comprises an antibody or an antigen binding fragment thereof, such as any of the antigen binding fragments described herein. For example, the antibody or antigen binding fragment thereof may be monoclonal antibody 3E10, or a variant thereof that retains cell penetrating activity, or an antigen binding fragment of 3E10 or said 3E10 variant. Additionally, the antibody or antigen binding fragment thereof may be an antibody that binds to the same epitope (e.g., target, such as DNA) as 3E10, or an antibody that has substantially the same cell penetrating activity as 3E10, or an antigen binding fragment thereof. These are exemplary of agents that can transit cells via ENT2. In certain embodiments, the internalizing moiety is capable of binding polynucleotides. In certain embodiments, the internalizing moiety is capable of binding DNA, such as double-stranded blunt DNA. In certain embodiments, the internalizing moiety is capable of binding DNA with a $K_D$ of less than 100 nM. In certain embodiments, the internalizing moiety is capable of binding DNA with a $K_D$ of less than 100 nM, less than 75 nM, less than 50 nM, or even less than 30 nM. $K_D$ is determined using SPR or QCM or ELISA, according to manufacturer's instructions and current practice. In some embodiments, $K_D$ is determined using a fluorescence polarization assay. In certain embodiments, $K_D$, with respect to binding to double stranded blunt DNA is evaluated using the following DNA as substrate: is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3' (SEQ ID NO: 18). In certain embodiments, the internalizing moiety is an anti-DNA antibody or antigen binding fragment.

In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced. At this point, 3E10 is generally not produced by the hybridoma but is produced recombinantly. Thus, in the context of the present application, 3E10 antibody, unless otherwise specified, will refer to an antibody having the sequence of the hybridoma or comprising a variable heavy chain domain comprising the amino acid sequence set forth in SEQ ID NO: 9 (which has a one amino acid substitution relative to that of the 3E10 antibody deposited with the ATCC, as described herein) and the variable light chain domain comprising the amino acid sequence set forth in SEQ ID NO: 7, and antibody fragments thereof.

The internalizing moiety may also comprise variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative or non-conservative substitutions are introduced into the heavy chain, the light chain and/or the constant region(s) of the antibody. Such variants include humanized versions of 3E10 or a 3E10 variant, particularly those with improved activity or utility, as provided herein. In some embodiments, the light chain or heavy chain may be modified at the N-terminus or C-terminus. Similarly, the foregoing description of variants applies to antigen binding fragments. Any of these antibodies, variants, or fragments may be made recombinantly by expression of the nucleotide sequence(s) in a host cell.

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety.

In certain embodiments, the internalizing moiety comprises an antibody or antigen binding fragment comprising an VH domain comprising an amino acid sequence at least 80%, 85%, 90%, 95%, 96%, 97%, 99%, or 100% identical to SEQ ID NO: 9 and/or a VL domain comprising an amino acid sequence at least 85%, 90%, 95%, 96%, 97%, 99%, or 100% identical to SEQ ID NO: 7, or a humanized variant thereof. In some embodiments, the internalizing moiety comprises any of the light chain variable domain described herein and a kappa constant domain (CL) having an amino acid sequence at least 85%, 90%, 95%, 96%, 97%, 99%, or 100% identical to SEQ ID NO: 15. In some embodiments, the internalizing moiety comprises an amino acid sequence at least 85%, 90%, 95%, 96%, 97%, 99%, or 100% identical to SEQ ID NO: 16. In some embodiments, the internalizing moiety comprises an amino acid sequence at least 85%, 90%, 95%, 96%, 97%, 99%, or 100% identical to SEQ ID NO: 17. It is understood that, when a signal sequence is included for expression of an antibody or antibody fragment, that signal sequence is generally cleaved and not presented in the finished chimeric polypeptide (e.g., the signal sequence is generally cleaved and present only transiently during protein production). Such internalizing moieties transit, in certain embodiments, cells via ENT2 and/or bind DNA. In certain embodiments, an internalizing moiety for use in the methods of the present disclosure (or an antibody or antigen binding fragment for such use) is not an antibody or antibody fragment having the VH and VL of the antibody produced by the hybridoma deposited with the ATCC under ATCC accession number PTA-2439. In some embodiments, an internalizing moiety for use in the methods of the present disclosure (or an antibody or antigen binding fragment for such use) is not an antibody or antibody fragment having a VH comprising the amino acid sequence set forth in SEQ ID NO: 9 and a VL comprising the amino acid sequence set forth in SEQ ID NO: 7.

In certain embodiments, the internalizing moiety is capable of binding polynucleotides. In certain embodiments, the internalizing moiety is capable of binding (specifically binding) DNA. In certain embodiments, the internalizing moiety is capable of binding DNA with a $K_D$ of less than 100 nM. In certain embodiments, the internalizing moiety is capable of binding DNA with a $K_D$ of less than 50 nM. In certain embodiments, the internalizing moiety is an anti-DNA antibody, such as an antibody or antigen binding fragment that binds double-stranded blunt DNA. In certain embodiments, the internalizing moiety is an anti-DNA antibody or antigen binding fragment (thereof), where $K_D$ is evaluated versus a double stranded DNA substrate, such as provided herein.

In certain embodiments, the internalizing moiety is cytotoxic and/or genotoxic to a tumor or cancerous cell but not to a non-tumor and/or non-cancerous cell. In some embodiments, the internalizing moiety is at least 10%, 20%, 30%, 40%, 50%, 60%, 70%, 80%, 90%, or 100% more toxic to a tumor or cancerous cell as compared to a non-tumor and/or non-cancerous cell. In some embodiments, an internalizing moiety of the disclosure, such as an antibody or antigen binding fragment of the disclosure, is at least 10%, 20%, 30%, 40%, 50%, 60%, 70%, 80%, 90%, or 100% more toxic to a tumor or cancerous cell, at a given concentration or dose, as compared to an Fv or scFv having an amino acid sequence of a murine 3E10, as deposited with the ATCC.

In certain embodiments, the internalizing moiety is an antigen binding fragment, such as a single chain Fv of 3E10

(scFv) comprising SEQ ID NOs: 7 and 9. In certain embodiments, the internalizing moiety comprises a single chain Fv of 3E10 (or another antigen binding fragment), and the amino acid sequence of the $V_H$ domain is at least 90%, 95%, 96%, 97%, 98%, 99%, or 100% identical to SEQ ID NO: 9, and amino acid sequence of the $V_L$ domain is at least 90%, 95%, 96%, 97%, 98%, 99%, or 100% identical to SEQ ID NO: 7. The variant 3E10 or fragment thereof retains the function of an internalizing moiety. When the internalizing moiety is an scFv, the VH and VL domains are typically connected via a linker, such as a gly/ser linker. The VH domain may be N-terminal to the VL domain or vice versa.

In certain embodiments, the internalizing moiety is an antigen binding fragment, such as a Fab comprising a VH and a VL. In certain embodiments, the internalizing moiety is a Fab (or another antigen binding fragment, such as a Fab'), and the amino acid sequence of the $V_H$ domain is at least 90%, 95%, 96%, 97%, 98%, 99%, or 100% identical to SEQ ID NO: 9. In certain embodiments, the internalizing moiety is a Fab (or another antigen binding fragment, such as a Fab'), and the amino acid sequence of the $V_L$ domain is at least 90%, 95%, 96%, 97%, 98%, 99%, or 100% identical to SEQ ID NO: 7. Our VH and VL domains, or combinations thereof, described herein are similarly contemplated. In certain embodiments, when the internalizing moiety is a Fab the heavy chain comprises a CH1 domain and an upper hinge of an immunoglobulin constant region. In certain embodiments, the upper hinge comprises a substitution, relative to a native immunoglobulin constant region, such as to decrease effector function and/or to eliminate a cysteine (e.g., a C to S). In certain embodiments, the upper hinge does not include a cysteine.

In certain embodiments, an internalizing moiety for use in the methods of the present disclosure (or an antibody or antigen binding fragment for such use) is not an antibody or antibody fragment having the VH and VL of the antibody produced by the hybridoma deposited with the ATCC under ATCC accession number PTA-2439. In some embodiments, an internalizing moiety for use in the methods of the present disclosure (or an antibody or antigen binding fragment for such use) is not an antibody or antibody fragment having a VH comprising the amino acid sequence set forth in SEQ ID NO: 9 and a VL comprising the amino acid sequence set forth in SEQ ID NO: 7.

In certain embodiments, the constant domain of the antibody or antibody fragment (e.g., antigen binding fragment) comprises all or a portion of a human Fc domain. In certain embodiments, the internalizing moiety is a full length antibody, and the constant domain of the antibody comprises a CH1, hinge, CH2 and CH3 domain. In certain embodiments, the constant domain comprises one or more substitutions, relative to a native immunoglobulin, that reduce effector function. Optionally, in certain embodiments, such a constant domain may include one or more (e.g., 1 substitution, 2 substitutions, 3 substitutions) substitutions in the heavy chain constant domain, such as in the hinge and/or CH2 domains, such as to reduce effector function. Such substitutions are known in the art.

In certain embodiments, the internalizing moiety is an antigen binding fragment—a fragment of an antibody comprising an antigen binding fragment. Suitable such fragments of antibodies, such as scFv, Fab, Fab' and the like are described herein. In certain embodiments, the internalizing moiety is an antigen binding fragment or a full length antibody. In certain embodiments, the internalizing moiety comprises a light chain comprising a constant region (CL). In certain embodiments, the internalizing moiety comprises a heavy chain comprising a constant region, wherein the constant region comprises a CH1 domain. In certain embodiments, the internalizing moiety comprises a heavy chain comprising a constant region and a light chain comprising a constant region, wherein the heavy chain constant region comprises a CH1 domain. Optionally, the internalizing moiety may further comprise a heavy chain constant region comprising all or a portion of a hinge (e.g., an upper hinge or more than the upper hinge). Optionally, the internalizing moiety may further comprise a heavy chain comprising a CH2 and/or CH3 domain.

In some embodiments, the internalizing moiety comprises one or more of the CDRs of the 3E10 antibody. In certain embodiments, the internalizing moiety comprises one or more of the CDRs of a 3E10 antibody comprising the amino acid sequence of a $V_H$ domain that is identical to SEQ ID NO: 9 and the amino acid sequence of a $V_L$ domain that is identical to SEQ ID NO: 7. The CDRs of the 3E10 antibody may be determined using any of the CDR identification schemes available in the art. For example, in some embodiments, the CDRs of the 3E10 antibody are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs of the 3E10 antibody are defined according to Chothia et al., 1987, J Mol Biol. 196: 901-917 and Chothia et al., 1989, Nature. 342:877-883. In other embodiments, the CDRs of the 3E10 antibody are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs of the 3E10 antibody are defined according to any of the CDR identification schemes discussed in Kunik et al., 2012, PLoS Comput Biol. 8(2): e1002388. In order to number residues of a 3E10 antibody for the purpose of identifying CDRs according to any of the CDR identification schemes known in the art, one may align the 3E10 antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence.

In certain embodiments, the internalizing moiety comprises at least 1, 2, 3, 4, or 5 of the CDRs of 3E10 as determined using the Kabat CDR identification scheme (e.g., the CDRs set forth in SEQ ID NOs: 32-37; the internalizing moiety is an antibody or antigen binding fragment thereof comprising a heavy chain comprising CDR1, CDR2, and CDR 3, as set forth in SEQ ID NOs: 32, 33 and 34, respectively, and a light chain comprising CDR1, CDR2, and CDR3, as set forth in SEQ ID NOs: 35, 36, and 37, respectively; e.g., and these CDRs in the internalizing moiety are as determined using the Kabat scheme). In other embodiments, the internalizing moiety comprises at least 1, 2, 3, 4 or 5 of the CDRs of 3E10 as determined using the IMGT identification scheme (e.g., the CDRs set forth in SEQ ID NOs: 1-6; the internalizing moiety is an antibody or antigen binding fragment thereof comprising a heavy chain comprising CDR1, CDR2, and CDR 3, as set forth in SEQ ID NOs: 1, 2, and 3, respectively, and a light chain comprising CDR1, CDR2, and CDR3, as set forth in SEQ ID NOs: 4, 5, and 6, respectively; e.g., and these CDRs in the internalizing moiety are as determined using the IMGT identification scheme). In certain embodiments, the internalizing moiety comprises all six CDRs of 3E10 as determined using the Kabat CDR identification scheme (e.g., comprises SEQ ID NOs 32-37). In other embodiments, the internalizing moiety comprises all six CDRS of 3E10 as determined using the IMGT identification scheme (e.g., which are set forth as SEQ ID NOs: 1-6). For any of the foregoing, in certain embodiments, the internalizing moiety is an antibody that binds the same epitope (e.g., the same target, such as DNA) as 3E10 and/or the internalizing moiety competes with 3E10 for binding to antigen. Exemplary internalizing moieties target and transit cells via ENT2. Exemplary internalizing moieties comprise antibodies or antigen binding fragments that bind DNA, such as double stranded blunt DNA.

In certain embodiments, the internalizing moiety comprising an antibody fragment, and the antibody fragment comprises an antigen binding fragment, such as an Fab or Fab'. In other words, in certain embodiments, the internalizing moiety comprises an Fab or Fab'.

In certain embodiments, the internalizing moiety competes with binding for a DNA substrate, such as double-stranded blunt DNA, with an antibody (or antigen-binding fragment) of the antibody produced by hybridoma 3E10 placed permanently on deposit with the American Type Culture Collection (ATCC) under ATCC accession number PTA-2439.

Preparation of antibodies or fragments thereof (e.g., a single chain Fv fragment encoded by $V_H$-linker-$V_L$ or $V_L$-linker-$V_H$ or a Fab) is well known in the art. In particular, methods of recombinant production of mAb 3E10 antibody fragments have been described in WO 2008/091911. Further, methods of generating scFv fragments of antibodies or Fabs are well known in the art. When recombinantly producing an antibody or antibody fragment, a linker may be used. For example, typical surface amino acids in flexible protein regions include Gly, Asn and Ser. One exemplary linker is provided in SEQ ID NO: 30, 31, or 45. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)$n, wherein n is an integer from 1-10, such as 2, 3, or 4. Other near neutral amino acids, such as Thr and Ala, can also be used in the linker sequence.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W. H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference.

These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

The disclosure contemplates the use of internalizing moieties (including antibodies or antigen binding fragments of the disclosure) described based on any combination of any of the foregoing or following structural and/or functional characteristics. Any such internalizing moieties, such as antibodies or antigen-binding fragments, are considered antibodies and antigen binding fragments of the disclosure and can be used for any of the uses or methods described herein, such as to treat cancer.

Further Examples of Antibodies or Antigen-Binding Fragments, such as Humanized Antibodies or Antigen Binding Fragments In some embodiments, the disclosure provides any of the antibodies or antigen-binding fragments disclosed herein, wherein the antibody or antigen-binding fragment is humanized. In other words, one class of internalizing moiety, such as antibody or antigen binding fragment, is a humanized antibody or antigen binding fragment. Such internalizing moiety may be humanized in whole or in part. Numerous examples are provided herein.

In one embodiment, the disclosure provides an antibody or antigen-binding fragment comprising a humanized antibody or antigen-binding fragment, wherein the humanized antibody or antigen-binding fragment comprises a light chain variable (VL) domain and a heavy chain variable (VH) domain; wherein the $V_H$ domain is humanized and comprises:
  a VH CDR1 having the amino acid sequence of SEQ ID NO: 1;
  a VH CDR2 having the amino acid sequence of SEQ ID NO: 2; and
  a VH CDR3 having the amino acid sequence of SEQ ID NO: 3;
and the VL is humanized and comprises:
  a VL CDR1 having the amino acid sequence of SEQ ID NO: 4;
  a VL CDR2 having the amino acid sequence of SEQ ID NO: 5; and
  a VL CDR3 having the amino acid sequence of SEQ ID NO: 6;
which CDRs are in accordance with the IMGT system, and
  wherein the humanized antibody or antigen-binding fragment has increased DNA binding and/or cell penetration, relative to that of a murine 3E10 antibody comprising a light chain variable (VL) domain having the amino acid sequence of SEQ ID NO: 7 and a heavy chain variable (VH) domain having the amino acid sequence of SEQ ID NO: 9. In certain embodiments, when comparing an antibody or antigen-binding fragment of the disclosure to a murine antibody or to another humanized antibody, the suitable comparison is between two proteins of the same structure (e.g., comparing a full length antibody to another full length antibody or comparing an Fab to another Fab). However, in other embodiments, the comparison is to an scFv or Fv of the murine antibody as a constant basis for comparison.

In some embodiments, an asparagine is mutated to another amino acid residue in the VH or VL domains in order to reduce N-linked glycosylation of the humanized antibody or antibody fragment. This humanized antibody or antibody fragment is based on a murine parent antibody—specifically a murine 3E10 antibody comprising a heavy chain and a light chain, wherein the light chain comprises a VL comprising the amino acid sequence of SEQ ID NO: 7 and the heavy chain comprises a VH comprising the amino acid sequence of SEQ ID NO: 9. In preferred embodiments, the internalizing moieties and fragments are associated with at least the cell-penetration properties associated with the murine 3E10 antibody (e.g., retain at least 75%, 80%, 85%, 90%, 95%, or greater than 95%) of the cell penetration properties. In certain embodiments, the humanized antibody or antibody fragment has one or more preferable cell penetration characteristics, such as improved penetration efficiency. In other embodiments, the humanized antibody or antibody fragment has improved DNA binding activity and/or a different range of DNA substrate affinity or specificity.

As used herein, the term "fragment" or "antigen-binding fragment" of a humanized antibody moiety or "antigen binding fragment" includes any fragment of a humanized internalizing moiety that retains at least the cell-penetration and/or DNA binding properties associated with the murine 3E10 antibody. In this application, the terms "fragment" and "antigen binding fragment" are used interchangeably. Exemplary antibody fragments include scFv fragments, Fab fragments (e.g., Fab' or F(ab')2), and the like.

In some embodiments, the humanized internalizing moiety (e.g., the humanized antibody and antigen binding fragments of the disclosure) is not directly fused to any heterologous agent or not fused or otherwise linked to a therapeutic or toxic heterologous agent. However, in such embodiments, and as described in greater detail below, the internalizing moiety may still be post-translationally modified (e.g., glycosylated or) and/or provided as part of a composition.

In other embodiments, the humanized internalizing moiety (e.g., the antibodies or antigen binding fragments of the disclosure, such as humanized antibodies or antibody binding fragments) is fused to a heterologous agent or a therapeutic or toxic heterologous agent. In some embodiments, the internalizing moiety effects delivery of a heterologous agent into a cell (i.e., penetrate desired cell; transport across a cellular membrane; deliver across cellular membranes to, at least, the cytoplasm). In certain embodiments, this disclosure relates to an internalizing moiety which promotes delivery of a heterologous agent into cancer or tumor cells, as well as certain other cell types. This portion promotes entry of the conjugate into cells. Like the murine, parental antibody, the humanized antibody and antigen binding fragments of the disclosure promote entry into cells via an ENT transporter, such as an ENT2 transporter and/or an ENT3 transporter. Without being bound by theory, ENT2 is expressed preferentially in certain cell types, including muscle (skeletal and cardiac), neuronal, liver and/or cancer/tumor cells. Accordingly, conjugates (e.g., conjugates in which a humanized antibody or antigen binding fragment of the disclosure is conjugated to a heterologous agent) are delivered into cells, but generally not ubiquitously. Rather, the conjugates may be delivered with some level of enrichment for particular tissues, including skeletal muscle, cardiac muscle, diaphragm, and ENT2 and/or ENT3 expressing cancer cells.

In certain embodiments, the internalizing moiety is capable of binding polynucleotides (e.g., a target/antigen for an antibody of the disclosure is DNA). This is consistent with the properties of the 3E10 antibody which is known to bind DNA (e.g., to specifically bind DNA). In certain embodiments, the internalizing moiety is capable of binding DNA. In certain embodiments, the internalizing moiety is capable of binding DNA with a $K_D$ of less than 100 nM. In certain embodiments, the internalizing moiety is capable of binding DNA (e.g., single stranded DNA or blunt double stranded DNA) with a $K_D$ of less than 500 nM, less than 100 nM, less than 75 nM, less than 50 nM, or even less than 30 nM, less than 20 nM, less than 10 nM, or even less than 1 nM. $K_D$ can be measured using Surface Plasmon Resonance (SPR) or Quartz Crystal Microbalance (QCM), or by ELISA, in accordance with currently standard methods. By way of example, an antibody or antibody fragment comprising a VH having the amino acid sequence set forth in SEQ ID NO: 10 and a VL having an amino acid sequence set forth in SEQ ID NO: 8 specifically binds DNA with a $K_D$ of less than 100 nM, and is an example of an anti-DNA antibody. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed.3004385), such as by ELISA, QCM, or Biacore. In certain embodiments, the foregoing $K_D$ of the antibody or antibody fragment (such as an antibody fragment comprising an antigen-binding fragment) is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3' (SEQ ID NO: 18)). In certain embodiments, the internalizing moiety is an anti-DNA antibody. Thus, in certain embodiments, an internalizing moiety (e.g., an antibody or antigen binding fragment) for use alone or associated with a heterologous agent comprises an antibody or antibody fragment that can transit cellular membranes into the cytoplasm and/or the nucleus and is capable of binding to DNA. In certain embodiments, the antibody and antigen binding fragments of the disclosure, such as humanized antibodies and antigen binding fragments, are based upon a murine, parental 3E10 antibody having VH and VL domains, as described above.

Preferably, the humanized antibody has the same, substantially the same, or even improved cell penetration and/or DNA binding characteristics in comparison to the murine, parental antibody, including a murine parental antibody comprising, when present, a murine constant domain.

In certain embodiments, the antibodies and antigen binding fragments of the disclosure have the same CDRs, as defined using the IMGT system, as the murine, parent antibody (e.g., the antibody comprising a heavy chain comprising a VH comprising the amino acid sequence set forth in SEQ ID NO: 9 and a light chain comprising a VL comprising the amino acid sequence set forth in SEQ ID NO: 7). In certain embodiments, the antibodies and antigen binding fragments of the disclosure have at least one CDR of the heavy chain and/or the light chain that differs from that of the murine, parent antibody (e.g., differ at VH CDR2 and/or VL CDR2 and/or VL CDR1, according to Kabat). In some embodiments, a humanized antibody or antigen binding fragment of the disclosure comprises a $V_H$ domain and a $V_L$ domain comprising:

a VH CDR1 having the amino acid sequence of SEQ ID NO: 1;
a VH CDR2 having the amino acid sequence of SEQ ID NO: 2;
a VH CDR3 having the amino acid sequence of SEQ ID NO: 3;
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are in accordance with the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 32;
a VH CDR2 having the amino acid sequence of SEQ ID NO: 33; and
a VH CDR3 having the amino acid sequence of SEQ ID NO: 34, which CDRs are according to Kabat; and
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are according to the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3, which CDRs are according to the IMGT system, and
a VL CDR1 having the amino acid sequence of SEQ ID NO: 35;
a VL CDR2 having the amino acid sequence of SEQ ID NO: 36; and
a VL CDR3 having the amino acid sequence of SEQ ID NO: 37, which CDRs are according to Kabat.

In certain embodiments, an antibody or antigen binding fragment of the disclosure comprises a $V_H$ domain comprising:

a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34, which CDRs are according to the Kabat system, and
a $V_L$ domain comprising
a VL CDR1 having the amino acid sequence of SEQ ID NO: 35 or 50;
a VL CDR2 having the amino acid sequence of SEQ ID NO: 51; and
a VL CDR3 having the amino acid sequence of SEQ ID NO: 37, which CDRs are according to Kabat.

As detailed throughout the application, the antibody or antigen-binding fragments of the disclosure, such as humanized antibody or antigen binding fragments, can be compared to the murine, parent antibody or to the original 3E10 antibody or antigen binding fragment thereof. Additionally or alternatively, antibodies of the disclosure (or antigen binding fragments thereof) can be compared to alternate antibodies and fragments (e.g., other humanized antibodies based on the same murine parent). In such scenarios, the comparison could be to an alternate antibody or antigen binding fragment have the foregoing 6 IMGT or Kabat CDRs, but have one or more changes in the framework regions relative to the humanized antibody or antigen-binding fragment of the disclosure. Also contemplated are antibodies or antigen binding fragments having the CDRs disclosed herein, but with one, two, three, or four amino acid substitutions in one or more CDRs (e.g., with one substitution in one CDR, with two substitution—one in each of two CDRS, or with three substitutions—one in each of three CDRs). When comparing activity, the ability and efficiency to penetrate cells, such as cancer or tumor cells, via ENT2 and/or ENT3 may be assessed. Activity will be considered comparable or substantially the same if it is approximately 70%, 75%, 80%, 85%, 90%, 95%, or greater than about 95% the activity of the murine, parental antibody. Activity is considered improved, relative to the murine, parental antibody, if a characteristic is at least about 5%, preferably at least about 10% better (e.g., approximately 105%, 110%, 115%, 120%, 125%, 130%, 150%, or greater than 150% the activity of the murine, parental antibody or an alternate humanized antibody). In certain embodiments, an activity is considered improved, relative to another antibody, if a characteristic is at least 2-fold better. In other embodiments, an activity is considered improved if a characteristic is at least 3-, 4-, 5-, 6-, 8, or 10-fold better.

Without being bound by theory, the internalizing moieties described herein are, in certain embodiments, capable of any one or more of the following: a) targeting (e.g., delivering) an agent conjugated to the internalizing moiety (e.g., any of the heterologous agents described herein) to muscle cells (e.g., cardiac or skeletal muscle), liver cells, neurons, glial cells and/or tumor or cancerous cells, b) killing and/or decreasing the growth, proliferation, size, survival or migration of a targeted tumor or cancer cell, c) sensitizing a tumor or cancer cell to the effects of any agent conjugated to the internalizing moiety (e.g., a chemotherapeutic attached thereto), and/or d) sensitizing a tumor or cancer cell to the effects of any separately administered agent or therapy (e.g., a chemotherapeutic agent or radiation therapy). In certain embodiments, the internalizing moiety is administered/delivered to cells in the absence of a heterologous agent (e.g., not interconnected to a heterologous agent; not interconnected to a therapeutic agent). For example, in certain embodiments, the internalizing moiety is administered to a subject having a tumor or a cancer to act itself as a therapeutic agent for treating the tumor or cancer.

In some embodiments, antibodies or humanized antibodies may comprise antibody fragments, derivatives or analogs thereof, including without limitation: antibody fragments comprising an antigen binding fragments (e.g., Fv fragments, single chain Fv (scFv) fragments, Fab fragments, Fab' fragments, F(ab')2 fragments, single domain antibodies, and multivalent versions of the foregoing; multivalent internalizing moieties including without limitation: Fv fragments, single chain Fv (scFv) fragments, Fab fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antigen-binding fragment is an scFv and a peptide linker interconnects the VH domain and the VL domain. In some embodiments, the antibodies or variants thereof may comprise a constant region that is a hybrid of several different antibody subclass constant domains (e.g., any combination of IgG1, IgG2a, IgG2b, IgG3 and IgG4).

In certain embodiments, the internalizing moiety is an antibody fragment comprising an antigen binding fragment. In other words, in certain embodiments, the internalizing moiety is not a full length antibody but is a fragment thereof comprising an antigen binding fragment. In certain embodiments, the internalizing moiety is an scFv, Fab, Fab', or Fab2'. In certain embodiments, the internalizing moiety is a full length antibody comprising a heavy chain comprising a CH1, hinge, CH2, and CH3 domains, optionally substituted to reduce effector function, such as in the hinge and/or CH2 domains, as described herein. In certain embodiments, the heavy chain comprises a VH domain, and a constant domain comprising a CH1, hinge, CH2, and CH3 domain. In certain embodiments, a heavy chain comprises a VH domain, and a constant domain comprising a CH1 domain and, optionally the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In certain embodiments, an antibody or antigen binding fragment as disclosed herein is a full length antibody comprising CH1, hinge, CH2, and CH3 of a heavy chain constant domain and a light chain constant domain. In certain embodiments the heavy chain constant region comprises one or more of a CH1, CH2, and CH3 domains, optionally with a hinge.

Monoclonal antibody 3E10 can be produced by hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used also herein to refer to a murine antibody (or antigen binding fragment) comprising the a VL domain comprising the amino acid sequence of SEQ ID NO: 7 and a VH domain comprising the amino acid sequence of SEQ ID NO: 9, regardless of the method used to produce the antibody. Thus, in the context of the present application, 3E10 antibody will refer, unless otherwise specified, to an antibody having the sequence of the hybridoma or comprising a variable heavy chain domain comprising the amino acid sequence set forth in SEQ ID NO: 9 (which has a one amino acid substitution relative to that of the 3E10 antibody deposited with the ATCC, as described herein and previously demonstrated as retaining cell penetration and DNA binding activity) and the variable light chain domain comprising the amino acid sequence set forth in SEQ ID NO: 7. However, in the context of the present disclosure, the parent murine antibody used as the basis for humanization was an antibody comprising the VL domain comprising the amino acid sequence of SEQ ID NO: 7 and a VH domain comprising the amino acid sequence of SEQ ID NO: 9. The disclosure provides, in certain embodiments, humanized antibodies based on murine 3E10.

Similarly, when referring to variants or antigen-binding fragments of 3E10, such terms are used without reference to the manner in which the antibody was produced. At this point, 3E10 is generally produced recombinantly.

The humanized internalizing moiety may also be derived from variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. In some embodiments, the light chain or heavy chain may be modified at the N-terminus or C-terminus. Moreover, the antibody or antibody fragment may be modified to facilitate conjugation to a heterologous agent. Similarly, the foregoing description of variants applies to antigen binding fragments. Any of these antibodies, variants, or fragments may be made recombinantly by expression of the nucleotide sequence(s) in a host cell. Such internalizing moieties can transit cells via an ENT transporter, such as ENT2 and/or ENT3 and/or bind the same epitope (e.g., target, such as DNA) as 3E10.

The humanized internalizing moiety may also be derived from mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain or the light chain. Numerous variants of mAb 3E10 have been characterized in, e.g., U.S. Pat. No. 7,189,396 and WO 2008/091911, the teachings of which are incorporated by reference herein in their entirety. In the examples provided herein, the parent, murine 3E10 comprises a VH comprising the amino acid sequence set forth in SEQ ID NO: 9 and a VL comprising the amino acid sequence set forth in SEQ ID NO: 7.

In certain embodiments, the internalizing moiety is an antigen binding fragment, such as a humanized single chain Fv (scFv). In other embodiments, the humanized antibody is a Fab' fragment.

In some embodiments, the internalizing moiety is an antibody or antibody fragment comprising an immunoglobulin heavy chain constant region or fragment thereof. As is known, each immunoglobulin heavy chain constant region comprises four or five domains. The domains are named sequentially as follows: $C_H1$-hinge-$C_H2$-$C_H3$(-$C_H4$). The DNA sequences of the heavy chain domains have cross-homology among the immunoglobulin classes, e.g., the $C_H2$ domain of IgG is homologous to the $C_H2$ domain of IgA and IgD, and to the $C_H3$ domain of IgM and IgE. As used herein, the term, "immunoglobulin Fc region" is understood to mean the carboxyl-terminal portion of an immunoglobulin heavy chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In one embodiment, the immunoglobulin Fc region comprises at least an immunoglobulin hinge region a CH2 domain and a CH3 domain, and lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region may comprise at least a portion of a hinge domain, and preferably at least a portion of a CH3 domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. In certain embodiments, the constant region domains are human. In some embodiments, the Fc portion of any of the internalizing moieties described herein has been modified such that it does not induce antibody-dependent cell-mediated cytotoxicity (ADCC). In some embodiments, the Fc portion has been modified such that it does not bind complement. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In some embodiments, the antibody or antigen binding fragment comprises hybrid heavy chain constant regions, i.e., the antibody or antigen binding fragment comprise multiple heavy chain constant region domains selected from: a CH1 domain, a CH2 domain, a CH3 domain, and a CH4 domain; wherein at least one of the constant region domains in the antibody or antigen binding fragment is of a class or subclass of immunoglobulin distinct from the class or subclass of another domain in the antibody or antigen binding fragment. In some embodiments, at least one of the constant region domains in the antibody or antigen binding fragment is an IgG constant region domain, and at least one of the constant region domains in the antibody or antigen binding fragment is of a different immunoglobulin class, i.e., an IgA, IgD, IgE, or IgM constant region domain. In some embodiments, at least one of the constant region domains in the antibody or antigen binding fragment is an IgG1 constant region domain, and at least one of the constant region domains in the antibody or antigen binding fragment is of a different IgG subclass, i.e., an IgG2A, IgG2B, IgG3 or IgG4. Suitable constant regions may be human or from another species (e.g., murine). Humanized antibodies and antigen binding fragments of the disclosure are consider humanized regardless of whether and constant region sequence (heavy or light chain), if present, corresponds to that of a human immunoglobulin or corresponds to that of another species.

The cell penetrating ability of the humanized internalizing moieties or fragments or variants may be utilized to promote delivery of a heterologous agent. Humanized moieties derived from 3E10 are particularly well suited for this because of their demonstrated ability to effectively promote delivery to tumor or cancer cells. Thus, humanized internalizing moieties are especially useful for promoting effective delivery into cells in subjects, such as human patients or model organisms. In certain embodiments, antibodies and antigen binding fragments of the disclosure are useful as intermediates for further conjugation to a heterologous agent, such as a heterologous protein, peptide, polynucleotide, or small molecule. However, in other embodiments, the humanized internalizing moieties or fragments or variants are not utilized to deliver any heterologous agent.

Preparation of antibodies or fragments thereof (e.g., a single chain Fv fragment encoded by $V_H$-linker-$V_L$ or $V_L$-linker-$V_H$) is well known in the art. In particular, methods of recombinant production of mAb 3E10 antibody fragments have been described in WO 2008/091911. Further, methods of generating scFv fragments of antibodies are well known in the art. When recombinantly producing an antibody or antibody fragment, a linker may be used. For example, typical surface amino acids in flexible protein regions include Gly, Asn and Ser. One exemplary linker is provided in SEQ ID NO: 30, 31 or 45. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4. Other near neutral amino acids, such as Thr and Ala, can also be used in the linker sequence.

In addition to linkers interconnecting portions of, for example, an scFv, the disclosure contemplates the use of additional linkers to, for example, interconnect the heterologous agent to the antibody portion of a conjugate or to interconnect the heterologous agent portion to the antibody portion of conjugate.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co.

(1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the humanized internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising an peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

A "Fab fragment" is comprised of one light chain and the $C_H1$ and variable regions of one heavy chain. Generally, the heavy chain of a Fab molecule cannot form a disulfide bond with another heavy chain molecule. A Fab may optionally include a portion of the hinge, such as the upper hinge.

A "Fab' fragment" contains one light chain and one heavy chain that contains more of the constant region, between the $C_H1$ and $C_H2$ domains, such that an interchain disulfide bond can be formed between two heavy chains to form a $F(ab')_2$ molecule.

A "$F(ab')_2$ fragment" contains two light chains and two heavy chains containing a portion of the constant region between the CH1 and CH2 domains, such that an interchain disulfide bond is formed between two heavy chains.

Native antibodies are usually heterotetrameric glycoproteins of about 150,000 daltons, composed of two identical light (L) chains and two identical heavy (H) chains.

Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the disclosure include full length or intact antibody, antibody fragments, native sequence antibody or amino acid variants, human, humanized (a form of chimeric antibodies), post-translationally modified, chimeric antibodies, immunoconjugates, and functional fragments thereof. The antibodies can be modified in the Fc region to provide desired effector functions or serum half-life.

Preparation of Antibodies

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. See, e.g., Fundamental Immunology, Ch. 7, 2.sup.nd ed., (Paul, W., ed.), 1989, Raven Press, N.Y. (incorporated by reference in its entirety for all purposes). The combination of the variable regions of each light chain/heavy chain pair typically forms the antigen-binding site. In some embodiments, antibodies or antigen binding fragments of the disclosure comprise the following constant domain scheme: IgG2a CH1-IgG1 hinge-IgG1 CH2-CH3. Other suitable combinations are also contemplated. In other embodiments, the antibody comprises a full length antibody and the CH1, hinge, CH2, and CH3 is from the same constant domain subclass (e.g., IgG1). In some embodiments, the antibodies or antigen binding fragment comprises an antigen binding fragment comprising a portion of the constant domain of an immunoglobulin, for example, the following constant domain scheme: IgG2a CH1-IgG1 upper hinge. In some embodiments, the antibodies or antigen binding fragments of the disclosure comprise a kappa constant domain (e.g., SEQ ID NO: 15).

The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific target (e.g., antigen, DNA in the context of the present disclosure). From N-terminal to C-terminal, both light and heavy chain variable regions typically comprise the domains FR1, CDR1, FR2, CDR2, FR3, CDR3 and FR4. The assignment of amino acids to each domain (FR or CDR) is typically in accordance with the definitions of Kabat Sequences of Proteins of Immunological Interest (1987 and 1991, National Institutes of Health, Bethesda, Md.). In certain embodiments, the CDRs of a particular antibody, such as an antibody provided herein, are CDRs, as defined by this Kabat system (e.g., the CDRs being referred to for an antibody or antigen binding fragment are identified using the Kabat system). Similarly, in certain embodiments, particularly when the CDRs are defined or identified as by the Kabat system, the FR regions are also defined and/or identified using the Kabat system. However, alternative systems for identifying CDR and FR regions are also available, including the IMGT system (described herein). In certain embodiments, the CDRs of a particular antibody, such as an antibody provided herein, are CDRs as defined by the IMGT system (e.g., CDRs for an antibody or antigen binding fragment are identified using the IMGT system).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63). In many cases, hybridomas are used to generate an initial antibody of murine or rodent origin. That initial antibody may then be modified, such as using recombinant techniques to produce rodent variants, chimeric antibodies, humanized antibodies and the like. Other methods exist to produce an initial antibody, and such methods are known in the art. However, regardless of the method used to generate an initial antibody or even a variant of that initial antibody, any given antibody of non-human origin can then be modified to increase its humanness.

It can be advantageous to increase the humanness of a non-human antibody to make it more suitable for use in human subject and cells, whether for diagnostic, therapeutic, or research purposes. Antibodies may be modified for use as therapeutics. Examples of such antibodies (including antibody fragments) include chimeric, humanized, and fully human antibodies. Numerous methods exist in the art for the generation of chimeric, humanized and human antibodies. In the context of the present disclosure, an antibody is considered humanized if at least one of the VH domain or VL domain is humanized. Moreover, an VH or VL domain is humanized if the amino acid sequence of at least a portion of at least one FR regions has been modified, relative to a parent murine antibody, such that the amino acid sequence of that portion corresponds to that of a human antibody or a human consensus sequence. In certain embodiments, at least one, two, three, or four FR regions of the VH domain and/or at least one, two, three, or four FR regions of the VL domain have been modified (in whole or in part) so that their sequence is more closely related to a human sequence. For any of the foregoing in certain embodiments, a humanized antibody fragment may be provided in the context of a human or non-human light chain and/or heavy chain constant region (e.g., comprising a CL and one or more of a CH1, hinge, CH2, and/or CH3 domains). In certain embodiments, a humanized antibody or antigen binding fragment of the disclosure is provided in the context of human light and/or heavy chain constant domains, when present. Numerous examples of humanized light and heavy chain variable domains based on a 3E10 parent antibody are provided herein. Antibodies and antibody binding fragments combining any of the humanized light chain variable domains and/or heavy chain variable domains described herein are exemplary of antibodies and antigen binding fragments of the disclosure.

Once the nucleotide sequences encoding such antibodies have been determined, chimeric or humanized antibodies may be produced by recombinant methods. Nucleic acids encoding the antibodies are introduced into host cells and expressed using materials and procedures generally known in the art.

In certain embodiments, the antibodies or antigen binding fragments of the disclosure are of the IgG1, IgG2, or IgG4 isotype. In certain embodiments of the disclosure, the antibodies comprise a human kappa light chain and a human IgG1, IgG2, or IgG4 heavy chain. In certain embodiments, the antibodies of the disclosure have been cloned for expression in mammalian cells.

Regardless of when an antibody of the disclosure is a full length antibody or an antigen binding fragment, antibodies and antigen binding fragments of the disclosure can be recombinantly expressed in cell lines. In these embodiments, sequences encoding particular antibodies can be used for transformation of a suitable host cell, such as a mammalian host cell or yeast host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the disclosure, a nucleic acid molecule encoding the amino acid sequence of a heavy chain constant region (all or a portion), a heavy chain variable region of the disclosure, a light chain constant region, or a light chain variable region of the disclosure is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, Meth. Enzymol. Vol. 185, Academic Press. N.Y. In the context of antibody expression, both the heavy and light chain may be expressed from the same vector (e.g., from the same or different promoters present on the same vector) or the heavy and light chains may be expressed from different vectors. In certain embodiments, the heavy and light chains are expressed from different vectors which are transfected into the same host cell and co-expressed. Regardless of when the heavy and light chains are expressed in the same host cell from the same or a different vector, the chains can then associate to form an antibody (or antibody fragment, depending on the portions of the heavy and light chain being expressed).

In some embodiments, an antibody or antigen binding fragment of the disclosure is not conjugated to a heterologous agent. In other embodiments, an antibody or antigen binding fragment of the disclosure is conjugated to a heterologous agent. In certain embodiments, the heterologous agent is a protein or peptide. That protein or peptide may be expressed as an inframe, co-translation fusion protein with, for example, the heavy chain, and expressed as described herein. Chemical conjugation is also possible. Conjugated as described in detail herein and unless otherwise specified, refers to scenarios where any of the antibody or antigen binding portions of the disclosure are associated with or interconnected with the heterologous agent, regardless of the interconnection (e.g., the interconnection/association may comprise a chemical conjugation, covalent bond, di-sulfide bond, etc. or combinations thereof). In certain embodiments, at least a portion of the interconnection is via a covalent bond, such as the forming of a fusion protein between a heavy chain of the antibody of the disclosure and the heterologous agent (which may further associate with a light chain of the antibody of the disclosure). Accordingly, the disclosure provides such conjugates and pharmaceutical compositions comprising such conjugates. A conjugate is a molecule comprising an antibody or antigen binding portion of the disclosure associate with a heterologous agent. Similarly, antibodies or antigen binding fragments of the disclosure may further comprise a heterologous agent. Conjugates along molecules where the two portions are associated or interconnected (e.g., the interconnection may comprise a chemical conjugation, covalent bond, di-sulfide bond, etc. or combinations thereof). In certain embodiments, at least a portion of the interconnection is via a covalent bond, such as the forming of a fusion protein between a heavy chain of an antibody of the disclosure and the heterologous agent (which may further associate with a light chain of the antibody or antibody fragment of the disclosure).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These portions of vectors are well known, and there are numerous generally available vectors that can be selected and used for the expression of proteins. One can readily selected vectors based on the desired host cell and application.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

The expression and cloning vectors of the disclosure will typically contain a promoter that is recognized by the host organism and operably linked to the molecule encoding heavy and/or light chain. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the heavy chain or light chain comprising an antibody or antigen binding fragment of the disclosure. In certain embodiments, the same promoter is used for both the heavy and light chain. In other embodiments, different promoters (present on the same or different vectors) are used for each.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, Nature 290:304-10); the CMV promoter; the promoter contained in the 3' long terminal repeat of Rous sarcoma virus (Yamamoto et al., 1980, Cell 22:787-97); the herpes thymidine kinase promoter (Wagner et al., 1981, Proc. Natl. Acad. Sci. USA 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. USA 75:3727-31); or the tac promoter (DeBoer et al., 1983, Proc. Natl. Acad. Sci. USA 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol. 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol. 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:338-40; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

The vector may also include an enhancer sequence to increase transcription of DNA encoding light chain or heavy chain.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an antibody or antigen binding fragment of the disclosure has been inserted into the proper site of the vector, the completed vector may be inserted into a suitable host cell for amplification and/or polypeptide expression. The transformation of an expression vector into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes the antibody or antigen binding fragment of the disclosure that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, one may select a cell line from the B cell lineage that does not make its own antibody but has a capacity to make and secrete a heterologous antibody (e.g., mouse myeloma cell lines NS0 and SP2/0). In other embodiments, a cell other than a mammalian cell is used, such as a yeast cell line (e.g., Pichia).

In certain embodiments, the cell line stably expresses an antibody or antigen binding fragment of the disclosure. In other embodiments, the cells transiently express an antibody or antigen binding fragment of the disclosure.

In certain embodiments is provided antibodies of the disclosure (including antigen binding fragments) that are substantially purified/isolated. Numerous methods, filters, and devices for substantially purifying antibodies grown in recombinant cell culture are available.

Antibody fragments can also be made by enzymatic digestion of a full length antibody.

In certain embodiments, the antibodies or antigen binding fragments of the disclosure, whether provided alone or as conjugates with a heterologous agent, are detectably labeled. In certain embodiments, the detectable label is itself an example of a heterologous agent. Methods for conjugation to a substance, such as a detectable label, are well known in the art. In one embodiment, the attached substance is a detectable label (also referred to herein as a reporter molecule). Suitable substances for attachment to include, but are not limited to, a fluorophore, a chromophore, a dye, a radioisotope, and combinations thereof. Methods for conjugation or covalently attaching another substance to an antibody are well known in the art.

The terms "label" or "labeled" refers to incorporation of a detectable marker, e.g., by incorporation of a radiolabeled amino acid or attachment to a polypeptide of biotin moieties that can be detected by marked avidin (e.g., streptavidin preferably comprising a detectable marker such as a fluorescent marker, a chemiluminescent marker or an enzymatic activity that can be detected by optical or colorimetric methods). Various methods of labeling polypeptides and glycoproteins are known in the art and may be used advantageously in the methods disclosed herein. Examples of labels for polypeptides include, but are not limited to, the following: radioisotopes or radionuclides (e.g., $^3$H, $^{14}$C, $^{15}$N, $^{35}$S, $^{90}$Y, $^{99}$mTc, $^{111}$In, $^{125}$I, $^{131}$I). In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^3$H), indium ($^{111}$In, $^{112}$In, $^{113}$mIn, $^{115}$mIn,) technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$SM, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh and $^{97}$Ru.).

Further examples of labels include fluorescent labels (e.g., fluoroscein isothiocyanate (FITC), rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

When present, regardless of the particular label, one of skill can select an appropriate label to facilitate purification, diagnostic, or research use. In other embodiments, the heterologous agent is a therapeutic molecule and either does not include a detectable label and/or epitope tag, or includes a therapeutic molecule in addition to the detectable label and/or epitope tag.

"Humanized" refers to an immunoglobulin such as an antibody, wherein the amino acids directly involved in antigen binding, the so-called complementary determining regions (CDR), of the heavy and light chains are not necessarily of human origin, while at least a portion of the rest of the variable domain (e.g., one or more of FR1, FR2, FR3, FR4) of one or both chains of the immunoglobulin molecule, the so-called framework regions of the variable heavy and/or light chains, and, if present, optionally the constant regions of the heavy and light chains are modified so that their amino acid sequence more closely correspond to human sequences.

A "humanized antibody" as used herein in the case of a two or greater chain antibody is one where at least one chain is humanized. A humanized antibody chain has a variable region where one or more of the framework regions are human or contain alterations, relative to a murine parent, so that one or more framework regions are more human than a murine parent. A humanized antibody which is a single chain is one where the chain has a variable region where one or more of the framework regions are human or contain alterations, relative to a murine parent, so that one or more framework regions are more human. The non-human portions of the variable region of the humanized antibody chain or antigen-binding fragment is derived from a non-human source, particularly a non-human antibody, typically of rodent origin. The non-human contribution to the humanized antibody is typically provided in the form of at least one CDR region which is interspersed among framework regions derived from one (or more) human immunoglobulin(s). In addition, framework support residues may be altered to preserve binding affinity. Thus, as is understood in the art, an entire framework region or all of the framework regions on a particular chain need not contain residues corresponding to a human antibody in order for the antibody to be considered humanized.

A "humanized antibody" may further comprise constant regions (e.g., at least one constant region or portion thereof, in the case of a light chain, and in some embodiments three constant regions in the case of a heavy chain). The constant regions of a humanized antibody, if present, typically are human in origin.

In some embodiments, a humanized antibody is generated by first subjecting a murine 3E10 light or heavy chain antibody sequence (e.g., the murine 3E10 antibody light and heavy chain amino acid sequences of SEQ ID NO: 7 and 9, respectively) to a sequence database search (e.g., BLAST) in order to identify the top closest human immunoglobulin kappa or heavy chain homologues in sequence similarity (e.g., the top 1, 2, 3, 4, 5, 6, 7, 8, 9 or 10 closest immunoglobulin kappa or heavy chain homologues). The top closest human immunoglobulin kappa or heavy chain homologues are considered candidates for kappa or heavy chain CDR grafting. In some embodiments, sequence alignment tools, such as Vector NTi sequence alignment tools, are then used to analyze the chimeric amino acid sequences consisting of the CDRs from the 3E10 kappa or heavy chain and the framework regions of any one of the top human immunoglobulin kappa or heavy chain homologues.

In general, as used herein, humanized antibodies comprise one or two variable domains in which all or part of the CDR regions correspond to parts derived from the non-human parent sequence and in which all or part of the FR regions are derived from a human immunoglobulin sequence. The humanized antibody can then, optionally, comprise at least one portion of a constant region of immunoglobulin (Fc), in particular that of a selected reference human immunoglobulin.

In some embodiments, the antibodies and antigen binding fragments of the disclosure (e.g., an antibody or antigen binding fragment, such as a humanized antibody or antigen binding fragment) comprises one or more of the CDRs of the 3E10 antibody. In certain embodiments, the antibodies and antigen binding fragments comprise one or more of the CDRs of a 3E10 antibody comprising a $V_H$ domain comprising the amino acid sequence set forth in SEQ ID NO: 9 and a $V_L$ domain comprising the amino acid sequence set forth in SEQ ID NO: 7. Either or both of the Kabat or IMGT CDRs may be used to refer to or describe an antibody. CDRs of the 3E10 antibody or an antibody of the disclosure may be determined using any of the CDR identification schemes available in the art, and such scheme may be used to describe the antibody. For example, in some embodiments, the CDRs are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs are defined according to Chothia et al., 1987, J Mol Biol. 196: 901-917 and Chothia et al., 1989, Nature. 342: 877-883. In other embodiments, the CDRs are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs are defined according to any of the CDR identification schemes discussed in Kunik et al., 2012, PLoS Comput Biol. 8(2): e1002388. In certain embodiments, antibodies and antigen binding fragments of the disclosure comprise one or more differences in the Kabat CDRs as compared to the murine, parent antibody. For example, in certain embodiments, the antibodies and antigen binding fragments of the disclosure differ at VH CDR2 and/or VL CDR2 and, optionally, at VL CDR1 in comparison to the murine, parent antibody. However, in certain embodiments, such antibodies share the IMGT CDRs of the murine, parent antibody.

Herein, the amino acid positions of residues in the VH and VL domains are referred to by linear sequence relative to, for example, SEQ ID NO: 7 or 9. Thus, the sequence of the VH and/or VL of an antibody or antigen binding fragment of the disclosure can be described relative to the corresponding amino acid position(s) of SEQ ID NO: 7 or 9. For example, an VH or VL domain may include an alteration at a particular amino acid position, and that position may correspond to a particular position in SEQ ID NO: 7 or 9.

However, the CDR identification scheme also provide numbering systems that may be used to facilitate comparisons between antibodies. Although not specifically used herein, one of skill in the art can readily use the available numbering scheme to refer to the CDRs described herein using a uniform numbering system, rather than by referring to the linear sequence. In certain embodiments, to number residues of an antibody for the purpose of identifying CDRs according to any of the CDR identification schemes known in the art, one may align the antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence. These uniform schemes for numbering residues are not expressly used herein, but can be readily used based on the disclosed sequences and identified CDRs.

In certain embodiments, the antibodies and antigen binding fragments of the disclosure (e.g., a humanized antibody or antigen binding fragment of the disclosure) comprises Kabat CDRs. In some embodiments, the antibodies and antigen binding fragments comprise a $V_H$ CDR1 that corresponds to amino acid residues 31-35 of SEQ ID NO: 9, a $V_H$ CDR2 that corresponds to amino acid residues 50-66 of SEQ ID NO: 9, and/or a $V_H$ CDR3 that corresponds to amino acid residues 99-105 of SEQ ID NO: 9. We note that this numbering of amino acid residues is with reference to the linear amino acid sequence of SEQ ID NO: 9. One of skill in the art can readily use the Kabat system to identify these residues using Kabat numbering. In certain embodiments, the antibodies and antigen binding fragments comprise a $V_L$ CDR1 that corresponds to amino acid residues 24-38 of SEQ ID NO: 7, a $V_L$ CDR2 that corresponds to amino acid residues 54-60 of SEQ ID NO: 7, and/or a $V_L$ CDR3 that corresponds to amino acid residues 93-101 of SEQ ID NO: 7. We note that this numbering of amino acid residues is with reference to the linear amino acid sequence of SEQ ID NO: 7. One of skill in the art can readily use the Kabat system to identify these residues using Kabat numbering.

In certain embodiments, the antibodies and antigen binding fragments of the disclosure comprise CDRs that are defined using the IMGT system. In some embodiments, the antibodies and antigen binding fragments comprise $V_H$ CDR1 that corresponds to amino acid residues 26-33 of SEQ ID NO: 9, a $V_H$ CDR2 that corresponds to amino acid residues 51-58 of SEQ ID NO: 9, and/or a $V_H$ CDR3 that corresponds to amino acid residues 97-105 of SEQ ID NO: 9. We note that this numbering of amino acid residues is with reference to the linear amino acid sequence of SEQ ID NO: 9. In certain embodiments, the antibodies and antigen binding fragments comprise a $V_L$ CDR1 that corresponds to amino acid residues 27-36 of SEQ ID NO: 7, a $V_L$ CDR2 that corresponds to amino acid residues 54-56 of SEQ ID NO: 7, and/or a $V_L$ CDR3 that corresponds to amino acid residues 93-101 of SEQ ID NO: 7. We note that this numbering of amino acid residues is with reference to the linear amino acid sequence of SEQ ID NO: 7. In certain embodiments, an antibody or antigen binding fragment of the disclosure comprises all 6 of the foregoing CDRs. In certain embodiments, the antibody or antigen binding fragment comprises 4 of the foregoing CDRs, and a VH CDR2 as set forth in SEQ ID NO: 49 and a VL CDR 2 as set forth in SEQ ID NO: 51.

In certain embodiments, the antibodies and antigen binding fragments of the disclosure comprise at least 1, 2, 3, 4, or 5 of the CDRs of 3E10 as determined using the Kabat CDR identification scheme (e.g., the CDRs set forth in SEQ ID NOs: 32-37). In certain embodiments, the antibody or antigen binding fragment further comprises a VH CDR2 as set forth in SEQ ID NO: 49 and/or a VL CDR2 as set forth in SEQ ID NO: 51 and/or a VL CDR1 as set forth in SEQ ID NO: 50. In certain embodiments, the antibodies and antigen binding fragments comprise at least 1, 2, 3, 4 or 5 of the CDRS of 3E10 as determined using the IMGT identification scheme (e.g., the CDRs set forth in SEQ ID NOs: 1-6). In certain embodiments, the antibodies and antigen binding fragments comprise all six CDRs of 3E10 as determined using the Kabat CDR identification scheme (e.g., comprises SEQ ID NOs 32-37). In other embodiments, the antibodies and antigen binding fragments comprise all six CDRS of 3E10 as determined using the IMGT identification scheme (e.g., which are set forth as SEQ ID NOs: 1-6). For any of the foregoing, in certain embodiments, the antibodies and antigen binding fragments is an antibody that binds the same epitope (e.g., the same target, such as DNA) as 3E10 and/or the internalizing moiety competes with 3E10 for binding to antigen (e.g., DNA). Exemplary antibodies and antigen binding fragments can transit cells via ENT2 and/or ENT3. In certain embodiments, antibodies or antigen binding fragments of the disclosure comprise 6 of the foregoing CDRs, but include 1, 2 3, or 4 amino acid substitutions in one or more CDRs. For example, the antibodies or antigen binding fragments comprise 3 CDR substitutions: one substitution in each of three CDRs.

In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using IMGT numbering (e.g., in one or more CDRs having the amino acid sequence of any one of SEQ ID NOs: 1-6, such as having 1-2, 1-3, 1-4, or 1-5 alternations) or Kabat numbering (e.g., in one or more CDRs having the amino acid sequence of any one of SEQ ID NOs: 32-37, such as having 1-2, 1-3, 1-4, or 1-5 alterations). In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using Kabat numbering (e.g., in one or more CDRs having the amino acid sequence of any one of SEQ ID NOs: 32-37, such as have 2, 3, 4, or 5 alterations) In some embodiments, antibodies or antigen binding fragments of the disclosure comprise a $V_L$ domain comprising one or more of the following amino acid alterations: M37L, H38A or E59Q, as compared with and numbered with respect to the linear amino acid sequence of SEQ ID NO: 7. In some embodiments, any of the antibodies or antigen binding fragments disclosed herein comprise a $V_H$ domain comprising a T63S alteration, as compared with and numbered with respect to the linear amino acid sequence of SEQ ID NO: 9. In some embodiments, antibodies or antigen binding fragments of the disclosure comprise a $V_L$ domain comprising an E59Q alteration as compared with and numbered with respect to the linear amino acid sequence of SEQ ID NO: 7, and a $V_H$ domain comprising a T63S alteration as compared with and numbered with respect to the linear amino acid sequence of SEQ ID NO: 9.

Without wishing to be bound by theory, one of the surprising findings of the present disclosure is the ability to generate antibodies and antigen-binding fragments that—have improved DNA binding activity versus murine 3E10, and further include an amino acid alteration (here, a substitution) in certain Kabat CDRs. Moreover, in certain embodiments, these improved antibodies having CDR substitutions are, in certain embodiments, also humanized.

In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In certain embodiments, the antibodies and antigen binding fragments of the disclosure comprise a variable heavy chain domain comprising at least one CDR different from the corresponding CDR set forth in SEQ ID NO: 9, as determined using the Kabat CDR identification scheme. In some embodiments, the at least one different CDR is $V_{H\ CDR}2$ as set forth in SEQ ID NO: 49.

In certain embodiments, the antibodies and antigen binding fragments of the disclosure comprise a variable light chain domain comprising at least one CDR different from the corresponding CDR set forth in SEQ ID NO: 7, as determined using the Kabat CDR identification scheme. In some embodiments, the at least one different CDR is a $V_{L\ CDR}1$ as set forth in SEQ ID NO: 50. In some embodiments, the at least one different CDR is a $V_L$ CDR2 as set forth in SEQ ID NO: 51.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in public databases. Regardless of the specific methodologies used to generate a humanized antibody or antibody fragment, the antibody must be evaluated to make sure that it (i) retains the desired function of the parent, murine antibody (or optionally has enhanced function); (ii) does not have deleterious properties that make it difficult to make or use; and preferably (iii) possesses one or more advantageous properties in comparison to the murine, parent antibody. Whether and to what extent any or all of these occur for any specific humanized antibody is unpredictable and uncertain. This is particularly true where substitutions are also introduced into the CDRs. Moreover, amongst a panel of humanized antibodies or antibody fragments, some may not have the required activity and one or more antibodies that do have the required activity may have advantageous properties in comparison to other humanized antibodies. This too is unpredictable and uncertain.

In certain embodiments, the antibodies or antigen-binding fragments of the disclosure comprise a light chain variable (VL) domain and a heavy chain variable (VH) domain; wherein the VL domain is humanized and comprises:
a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3; which CDRs are in accordance with the IMGT system
and the VH domain is humanized and comprises:
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6; which CDRs are in accordance with the IMGT system, and wherein the antibody or antigen-binding fragment has increased DNA binding and/or cell penetration, relative to that of a murine 3E10 antibody comprising a light chain variable (VL) domain having the amino acid sequence of SEQ ID NO: 7 and a heavy chain variable (VH) domain having the amino acid sequence of SEQ ID NO: 9.

In certain embodiments the antibodies or antigen-binding fragments of the disclosure comprise a light chain variable (VL) domain and a heavy chain variable (VH) domain; wherein the VH domain comprises:
a VH CDR1 having the amino acid sequence of SEQ ID NO: 32;

a VH CDR2 having the amino acid sequence of SEQ ID NO: 49; and
a VH CDR3 having the amino acid sequence of SEQ ID NO: 34,
which CDRs are according to the Kabat system;
and the VL comprises:
a VL CDR1 having the amino acid sequence of SEQ ID NO: 50;
a VL CDR2 having the amino acid sequence of SEQ ID NO: 51; and
a VL CDR3 having the amino acid sequence of SEQ ID NO: 37,
which CDRs are according to the Kabat system;
wherein the antibody or antigen-binding fragment binds DNA.

In certain embodiments the antibodies or antigen-binding fragments of the disclosure comprise a light chain variable (VL) domain and a heavy chain variable (VH) domain; wherein the VH domain comprises:
a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34,
which CDRs are according to Kabat;
and the VL comprises:
a VL CDR1 having the amino acid sequence of SEQ ID NO: 35;
a VL CDR2 having the amino acid sequence of SEQ ID NO: 51; and
a VL CDR3 having the amino acid sequence of SEQ ID NO: 37,
which CDRs are according to Kabat;
wherein the antibody or antigen-binding fragment binds DNA.

In certain embodiments, antibodies or antigen binding fragments of the disclosure penetrate cells (e.g., can transit the plasma membrane and enter into cells, such as cells expressing ENT2).

In some embodiments, the VH domain is humanized. In some embodiments, the VL domain is humanized.

In certain embodiments the antibodies or antigen-binding fragments of the disclosure comprise a $V_L$ domain that comprises the amino acid sequence set forth in SEQ ID NO: 40, or an amino acid sequence that differs from SEQ ID NO: 40 by the presence of a total of 1, 2, 3, 4, 5, or 6 amino acid substitutions, insertions and/or deletions in the framework regions, as defined by the IMGT system, relative to SEQ ID NO: 40. In other embodiments, the $V_L$ domain comprises the amino acid sequence set forth in SEQ ID NO: 8, or an amino acid sequence that differs from SEQ ID NO: 8 by the presence of a total of 1, 2, 3, 4, 5, or 6 amino acid substitutions, insertions and/or deletions in the framework regions, as defined by the IMGT system, relative to SEQ ID NO: 8. In some embodiments, the VL domain comprises the amino acid sequence set forth in SEQ ID NO: 40. In some embodiments, the VL domain comprises the amino acid sequence set forth in SEQ ID NO: 8.

In certain embodiments the antibodies or antigen-binding fragments of the disclosure comprise a $V_H$ domain that comprises the amino acid sequence set forth in SEQ ID NO: 38, or an amino acid sequence that differs from SEQ ID NO: 38 by the presence of a total of 1, 2, 3, 4, 5, or 6 amino acid substitutions, insertions and/or deletions in the framework regions, as defined by the IMGT system, relative to SEQ ID NO: 38. In some embodiments, the $V_H$ domain comprises the amino acid sequence set forth in SEQ ID NO: 39, or an amino acid sequence that differs from SEQ ID NO: 39 by the presence of a total of 1, 2, 3, 4, 5, or 6 amino acid substitutions, insertions and/or deletions in the framework regions, as defined by the IMGT system, relative to SEQ ID NO: 39. In some embodiments, the $V_H$ domain comprises the amino acid sequence set forth in SEQ ID NO: 10, or an amino acid sequence that differs from SEQ ID NO: 10 by the presence of a total of 1, 2, 3, 4, 5, or 6 amino acid substitutions, insertions and/or deletions in the framework regions, as defined by the IMGT system, relative to SEQ ID NO: 10. In some embodiments, the VH domain comprises the amino acid sequence set forth in SEQ ID NO: 38. In some embodiments, the VH domain comprises the amino acid sequence set forth in SEQ ID NO: 39. In some embodiments, the VH domain comprises the amino acid sequence set forth in SEQ ID NO: 10.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 8; wherein the $V_H$ domain comprises three CDRs of the amino acid sequence set forth in SEQ ID NO: 9, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells.

In certain embodiments, the $V_H$ domain of the antibodies or antigen-binding fragments described herein comprise:
a VH CDR1 having the amino acid sequence of SEQ ID NO: 1;
a VH CDR2 having the amino acid sequence of SEQ ID NO: 2; and a VH CDR3 having the amino acid sequence of SEQ ID NO: 3.

In certain embodiments, the $V_L$ domain of the antibodies or antigen-binding fragments described herein comprise:

a VL CDR1 having the amino acid sequence of SEQ ID NO: 4;

a VL CDR2 having the amino acid sequence of SEQ ID NO: 5; and a VL CDR3 having the amino acid sequence of SEQ ID NO: 6.

In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 8; wherein the $V_H$ domain comprises three CDRs of the amino acid sequence set forth in SEQ ID NO: 9, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells.

In some embodiments, an antibody or antigen-binding fragment of the disclosure comprises: a) a humanized $V_H$ domain that comprises the amino acid sequence of SEQ ID NO: 10, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 10, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 10, and b) a humanized $V_L$ domain that comprises the amino acid sequence of SEQ ID NO: 40. In some embodiments, an antibody or antigen-binding fragment of the disclosure comprises: a) a humanized $V_H$ domain that comprises the amino acid sequence of SEQ ID NO: 38, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 38, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 38, and b) a humanized $V_L$ domain that comprises the amino acid sequence of SEQ ID NO: 40. In some embodiments, an antibody or antigen-binding fragment of the disclosure comprises: a) a humanized $V_H$ domain that comprises the amino acid sequence of SEQ ID NO: 39, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 39, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 39, and b) a humanized $V_L$ domain that comprises the amino acid sequence of SEQ ID NO: 40. In some embodiments, an antibody or antigen-binding fragment of the disclosure comprises: a) a $V_H$ domain that comprises the amino acid sequence of SEQ ID NO: 9, and b) a humanized $V_L$ domain that comprises the amino acid sequence of SEQ ID NO: 8. In some embodiments, an antibody or antigen-binding fragment of the disclosure comprises: a) a $V_H$ domain that comprises the amino acid sequence of SEQ ID NO: 9, and b) a humanized $V_L$ domain that comprises the amino acid sequence of SEQ ID NO: 40.

In some embodiments, an antibody or antigen-binding fragment of the disclosure includes a signal sequence. In some embodiments, the signal sequence is conjugated to the N-terminal portion of any of the $V_L$ sequences disclosed herein (e.g., SEQ ID NO: 8). In some embodiments, the signal sequence conjugated to the light chain is SEQ ID NO: 16. In some embodiments, the signal sequence is conjugated to the N-terminal portion of any of the $V_H$ sequences disclosed herein (e.g., SEQ ID NO: 10). In some embodiments, the signal sequence conjugated to the heavy chain is SEQ ID NO: 17. It is understood that, when a signal sequence is included for expression of an antibody or antibody fragment, that signal sequence is generally cleaved and not present in the finished polypeptide (e.g., the signal sequence is generally cleaved and present only transiently during protein production).

In some embodiments, the $V_H$ domain of any of the antibodies or antigen-binding fragments of the disclosure described herein comprise one or more of the following amino acid alterations: V5Q, E6Q, L11V, V12I, K13Q, R18L, K19R, V37I, E42G, A49S, T63S, A75S, F80Y, T84N, S88A, M93V, T111L or L112V, as compared with an numbered with reference to the amino acid sequence of SEQ ID NO: 9. In other words, in certain embodiments, an antibody or antigen-binding fragment comprises one or more amino acid alteration at a position corresponding to the foregoing, where the corresponding position is compared with SEQ ID NO: 9. In certain embodiments, the $V_H$ domain comprises one or more of the following amino acid alterations: V5Q, L11V, K13Q, R18L, K19R, V37I, E42G, A49S, T63S, A75S, F80Y, T84N, M93V, T111L or L112V, as compared with and numbered with reference to the amino acid sequence of SEQ ID NO: 9. In certain embodiments, the $V_H$ domain comprises at least 5, at least 6, at least 7, at least 8, at least 9, at least 10, at least 11, at least 12, at least 13, at least 14, at least 15, at least 16, or at least 17 of said alterations, as compared with and numbered with reference to the amino acid sequence of SEQ ID NO: 9. In certain embodiments, at least one of the alterations in the $V_H$ domain is a V5Q alteration, as compared with and numbered with reference to the amino acid sequence of SEQ ID NO: 9. In certain embodiments, at least one of the alterations in the $V_H$ domain is a E6Q alteration, as compared with and numbered with reference to the amino acid sequence of SEQ ID NO: 9. In certain embodiments, at least one of the alterations in the $V_H$ domain is a L11V alteration, as compared with and numbered with reference to the amino acid sequence of SEQ ID NO: 9. In certain embodiments, at least one of the alterations in the $V_H$ domain is a V37I alteration, as compared with and numbered with reference to the amino acid sequence of SEQ ID NO: 9. In certain embodiments, the $V_H$ domain retains a serine at the amino acid position corresponding to amino acid position 88 of SEQ ID NO: 9. In certain embodiments, the $V_H$ domain retains a valine at the amino acid position corresponding to amino acid position 12 of SEQ ID NO: 9. In certain embodiments, the $V_H$ domain retains a tryptophan at the amino acid position corresponding to amino acid position 47 of SEQ ID NO: 9. All operable combinations of the foregoing are contemplated, as are combinations with any of the aspect and embodiments provided herein for the VL. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In certain embodiments of any of the foregoing, or of any of the aspects and embodiments disclosed herein, the $V_L$ domain of any of the humanized antibodies or antigen-binding fragments described herein comprise one or more of the following amino acid alterations: V3Q, L4M, A9S, A12S, V13A, L15V, Q17D, A19V, S22T, M37L, H38A, G45E, Q46K, P47A, E59Q, A64S, H76T, N78T, H80S, P81S, V82L, E83Q, E84P, A87V, A87F, or G104A, as compared with and numbered with reference to the amino acid sequence of SEQ ID NO: 7. In certain embodiments, the $V_L$ domain comprises one or more of the following amino acid alterations: V3Q, L4M, A9S, A12S, V13A, L15V, Q17D, A19V, G45E, Q46K, P47A, E59Q, A64S, H76T, N78T, H805, P81S, V82L, E83Q, E84P, A87V, or G104A, as compared with and numbered with reference to the amino acid sequence of SEQ ID NO: 7. In certain embodiments, the $V_L$ domain comprises at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 of said amino acid alterations, as compared with and numbered with reference to the amino acid sequence of SEQ ID NO: 7.

It should be understood that any of the foregoing variations at particular positions are referred to relative to the amino acid sequence set forth in SEQ ID NO: 7 or 9. An antibody or antigen binding fragment of the disclosure may comprise one or more of such amino acid alterations at the corresponding position, relative to the amino acid sequence of SEQ ID NO: 7 or 9. By way of example, in certain embodiments, the VH domain comprises an L to V alteration at a position corresponding to position 11 of SEQ ID NO: 9 (e.g., an L11V alteration). This is exemplary of how all of the foregoing alterations can also be described, and such description is expressly contemplated. By way of another example, in certain embodiments, the VL domain comprises a V to Q alteration at a position corresponding to position 3 of SEQ ID NO: 7 (e.g., a V3Q alteration).

In certain embodiments, the $V_L$ domain comprises a serine at each of the amino acid positions corresponding to amino acid positions 80 and 81 of SEQ ID NO: 7. In certain embodiments, the $V_L$ domain retains a lysine at the amino acid position corresponding to amino acid position 53 of SEQ ID NO: 7. In certain embodiments, the $V_L$ domain does not have any one or more of the following amino acid combinations:

a) asparagine and serine at the amino acid positions corresponding to amino acid positions 80 and 81 of SEQ ID NO: 7, respectively; or b) asparagine and glycine at the amino acid positions corresponding to amino acid positions 80 and 81 of SEQ ID NO: 7, respectively; or c) asparagine and proline at the amino acid positions corresponding to amino acid positions 80 and 81 of SEQ ID NO: 7, respectively. All operable combinations of the foregoing are contemplated, as are combinations with any of the aspect and embodiments provided herein for the VH. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In some embodiments, the humanized internalizing moiety (e.g., a humanized antibody or antigen-binding fragment comprising a light chain variable ($V_L$) domain comprising the amino acid sequence set forth in SEQ ID NO: 8 and a heavy chain variable ($V_H$) domain comprising the amino acid sequence set forth in SEQ ID NO: 10) is associated with at least one superior physiological or biological property as compared to a reference non-humanized internalizing moiety (e.g., the murine, parent 3E10 antibody). In other embodiments, the humanized internalizing moiety is associated with at least two superior physiological or biological properties as compared to a reference non-humanized internalizing moiety. In other embodiments, the humanized internalizing moiety is associated with at least three superior physiological or biological properties as compared to a reference non-humanized internalizing moiety (e.g., the murine, parent 3E10 antibody). In some embodiments, the reference non-humanized internalizing moiety comprises the murine parent antibody comprising a VH comprising the amino acid sequence of SEQ ID NO: 9 and a VL comprising the amino acid sequence of SEQ ID NO: 7. In some embodiments, the reference humanized internalizing moiety is an antibody comprising the amino acid sequence of SEQ ID NO: 43. In some embodiments, the reference internalizing moiety is a humanized antibody or antigen binding fragment comprising the $V_H$ amino acid sequence of SEQ ID NO: 42 and the $V_L$ amino acid sequence of SEQ ID NO: 41.

In certain embodiments, the antibodies or antigen-binding fragments described herein are humanized and are associated with at least one superior biological or physiological property as compared to a murine antibody, which murine antibody comprises a $V_L$ domain comprising the amino acid sequence set forth in SEQ ID NO: 7 and a $V_H$ domain comprising the amino acid sequence set forth in SEQ ID NO: 9, and/or as compared to an alternative antibody or antigen-binding fragment thereof, wherein said alternative antibody or antigen-binding fragment comprises a $V_L$ domain comprising the CDRs of the amino acid sequence set forth in SEQ ID NO: 7 and a $V_H$ domain comprising the CDRs of the amino acid sequence set forth in SEQ ID NO: 9; and wherein said alternative antibody or fragment does not comprise a $V_L$ domain comprising the amino acid sequence of SEQ ID NO: 8 or 40, and/or wherein said alternative antibody or fragment does not comprise a $V_H$ domain comprising the amino acid sequence of any of SEQ ID NOs: 10, 38 or 39; or, in some embodiments, wherein said alternative antibody or fragment does not comprise a $V_L$ domain comprising the amino acid sequence of SEQ ID NO: 8, and/or wherein said alternative antibody or fragment does not comprise a $V_H$ domain comprising the amino acid sequence of any of SEQ ID NOs: 10.

In some embodiments, a humanized internalizing moiety of the disclosure (e.g., a humanized antibody or antigen-binding fragment thereof comprises a light chain variable ($V_L$) domain comprising the amino acid sequence set forth in SEQ ID NO: 8 and a heavy chain variable ($V_H$) domain comprising the amino acid sequence set forth in SEQ ID NO: 10) is associated with at least one superior physiological or biological property as compared to an alternative internalizing moiety or fragment thereof (e.g., a different humanized antibody based on the same parent, murine antibody and, optionally, having the same CDRs). In other embodiments, a humanized internalizing moiety of the disclosure is associated with at least two superior physiological or biological properties as compared to the alternative internalizing moiety (e.g., a different humanized antibody based on the same parent, murine antibody and, optionally, having the same CDRs). In other embodiments, the humanized internalizing moiety of the disclosure is associated with at least three superior physiological or biological properties as compared to the alternative internalizing moiety (e.g., a different humanized antibody based on the same parent, murine antibody and, optionally, having the same CDRs). In some embodiments, the alternative antibody is the parent antibody from which the humanized antibody was derived (e.g., the parent, murine antibody). In some embodiments, the alternative antibody is another humanized antibody that is derived from the 3E10 antibody but that has a different amino acid sequence than the humanized internalizing moieties or antigen-binding fragments thereof of the present disclosure. In some embodiments, an antibody or antigen binding fragment of the disclosure has one or more improved characteristics in comparison to the murine parent antibody and/or an alternative humanized antibody. In some embodiments, the alternative humanized antibody has one, two, or three amino acid substitutions in the Kabat CDRs, as compared to an antibody of the disclosure. In some embodiments, the alternative internalizing moiety or fragment thereof comprises:

a VH CDR1 having the amino acid sequence of SEQ ID NO: 32;
a VH CDR2 having the amino acid sequence of SEQ ID NO: 33;
a VH CDR3 having the amino acid sequence of SEQ ID NO: 34;
a VL CDR1 having the amino acid sequence of SEQ ID NO: 35;
a VL CDR2 having the amino acid sequence of SEQ ID NO: 36; and
a VL CDR3 having the amino acid sequence of SEQ ID NO: 37, which CDRs are defined in accordance with Kabat, but does not comprise the same scaffold amino acid sequence present in the humanized internalizing moieties or fragments thereof of the present disclosure (e.g. a humanized internalizing moiety or fragment thereof comprising the amino acid sequence of any of SEQ ID NOs: 8, 10, or 38-40).

In some embodiments, the superior biological or physiological property associated with the humanized internalizing moieties or fragments of the disclosure described herein is that the humanized internalizing moiety or antigen-binding fragment is associated with reduced immunogenicity in a human patient as compared to the immunogenicity of the non-humanized or to the alternative antibody or antigen-binding fragment in a human patient. The skilled worker is familiar with numerous assays for determining the immunogenicity of the antibodies. In preferred embodiments, the humanized antibodies of the disclosure are associated with reduced immunogenicity in a human patient, but retain the cell penetration properties associated with the murine 3E10 antibody.

In some embodiments, the superior biological or physiological property associated with the humanized internalizing moieties or fragments of the disclosure described herein is that the humanized internalizing moiety or antigen-binding fragment is associated with increased solubility in a physiologically acceptable carrier as compared to the solubility of the non-humanized or to the alternative antibody or antigen-binding fragment in the same type of physiologically acceptable carrier. As used herein, a physiologically acceptable carrier includes include water, ethanol, polyols (such as glycerol, propylene glycol, polyethylene glycol, and the like), and suitable mixtures thereof, vegetable oils, such as olive oil, and injectable organic esters, such as ethyl oleate. In some embodiments, the humanized internalizing moiety or fragment is associated with at least 5%, 10%, 25%, 50%, 75%, 100%, 150%, 200% or 300% greater solubility in a physiologically acceptable carrier as compared to a non-humanized or alternative internalizing moiety or antigen-binding fragment in the same type of physiologically acceptable carrier. The skilled worker is aware of routine experiments that may be utilized for testing the solubility of the humanized internalizing moieties or fragments thereof. Examples of solubility assays include standard turbidity or light-scattering assays, commercial solubility assays, such as the OptiSol™ solubility assay kit (DiLyx, Seattle, Wash.), or the protein solubility assay screen described in Bondos et al., 2003, Analytical Biochemistry, 316:223-231 may be utilized.

In some embodiments, the superior biological or physiological property associated with the humanized internalizing moieties or fragments of the disclosure described herein is that the humanized internalizing moiety or antigen-binding fragment is associated with a higher expression level in a type of cell as compared to the expression level of the non-humanized or alternative antibody or antigen-binding fragment in the same type of cell. In some embodiments, the humanized internalizing moiety or fragment is associated with at least 5%, 10%, 25%, 50%, 75%, 100%, 150%, 200% or 300% higher expression level in a cell as compared to the expression level of a non-humanized or alternative internalizing moiety or antigen-binding fragment in the same type of cell. The skilled worker is aware of routine experiments that may be utilized for testing the expression level of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with lower toxicity (e.g., cytotoxicity and/or genotoxicity) in a cell type as compared to the toxicity in the same type of cell that is associated with the non-humanized or alternative antibody or antigen-binding fragment. In some embodiments, the humanized internalizing moiety or fragment is associated with at least 5%, 10%, 25%, 50%, 75%, 100%, 150%, 200% or 300% lower toxicity as compared to the toxicity of a non-humanized or alternative internalizing moiety or antigen-binding fragment in the same type of cell. In some embodiments the cell is a mammalian cell. In some embodiments the cell is a human cell. In some embodiments, the cell is in an organism, such as a mammal. In some embodiments, the cell is a human cell in a human organism. The skilled worker is aware of routine experiments that may be utilized for testing the toxicity of the humanized internalizing moieties or fragments thereof. For example, the toxicity of the humanized internalizing moieties or fragments of the disclosure and of the non-humanized or alternative internalizing moieties or fragments thereof may be tested in an in vitro cell or cell culture, such as in a cell or cell culture derived from human cells, or may be tested in an in vitro animal model such as a mouse or rat.

In some embodiments, the superior biological or physiological property associated with the humanized internalizing moieties or fragments of the disclosure described herein is that the humanized internalizing moiety or antigen-binding fragment is associated with reduced aggregation in a physiologically acceptable carrier as compared to aggregation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less aggregation in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with reduced aggregation after a period of at least 1 hour, 6 hours, 12 hours, 18 hours, 24 hours, 36 hours, 2 days, 5 days, one week, two weeks, four weeks, one month, two months, three months, six months or one year. The skilled worker is aware of routine experiments that may be utilized for testing the aggregation of the humanized internalizing moieties or fragments thereof. Examples of aggregation assays include standard turbidity or light-scattering assays (e.g., A600 nm assay), visual inspection, SDS-PAGE, commercial aggregation assays, such as the OptiSol™ aggregation assay kit (DiLyx, Seattle, Wash.), HP-SEC analysis, or the protein aggregation assay screen described in Bondos et al., 2003, Analytical Biochemistry, 316:223-231 may be utilized.

In some embodiments, the superior biological or physiological property associated with the humanized internalizing moieties or antigen-binding fragments of the disclosure described herein is that the humanized internalizing moiety or antigen-binding fragment is associated with increased stability in a physiologically acceptable carrier as compared to the stability of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% greater stability in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with increased stability after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the stability of the humanized internalizing moieties or fragments thereof. For example, the skilled worker could test the stability of the humanized and non-humanized or alternative internalizing moieties or fragments thereof after various intervals of being stored in a physiologically acceptable carrier. Commercial assays such as the ProteoStat™ Thermal shift stability assay (Enzo, Farmingdale, N.Y.) may be utilized in assessing the stability of the moieties or fragments thereof. Alternatively, the stability of the moieties or fragments thereof may be determined by HP-SEC or by SDS-PAGE analysis.

In some embodiments, the superior biological or physiological property associated with the humanized internalizing moieties or antigen-binding fragments of the disclosure described herein is that the humanized internalizing moiety or antigen-binding fragment is associated with improved cell penetration as compared to the cell penetration of the non-humanized or alternative antibody or antigen-binding fragment. In some embodiments, the improved penetration is due to the increased efficiency of the humanized internalizing moiety or antigen-binding fragment to be internalized by an ENT transporter (e.g., an ENT2 and/or ENT3 transporter). In some embodiments, the humanized internalizing moiety or fragment is associated with at least 5%, 10%, 25%, 50%, 75%, 100%, 150%, 200% or 300% greater cell penetration as compared to a non-humanized or alternative internalizing moiety or antigen-binding fragment in the same type of physiologically acceptable carrier. The skilled worker is aware of routine experiments that may be utilized for testing the cell penetration of the humanized internalizing moieties or fragments thereof. For example, the humanized internalizing moieties or fragments thereof may be labeled (e.g. fluorescently or radiolabeled) and administered to a cell or cell culture in order to determine the cell penetration of the humanized internalizing moieties or fragments thereof. Alternatively, the humanized internalizing moieties or fragments may be administered to a cell or cell culture and then detected with a secondary agent, e.g., a fluorescently labeled or radiolabeled secondary antibody, in order to determine the cell penetration of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with reduced glycosylation in a cell type as compared to the glycosylation of the non-humanized or alternative antibody or antigen-binding fragment in the same cell type. In some embodiments, an asparagine is mutated to another amino acid residue in the VH or VL domains in order to reduce N-linked glycosylation of the humanized antibody or antibody fragment. In other embodiments, the superior biological or physiological property associated with the humanized internalizing moieties or fragments described herein is that the humanized internalizing moiety or antigen-binding fragment is associated with increased glycosylation in a cell type as compared to the glycosylation of the non-humanized or alternative antibody or antigen-binding fragment in the same cell type. In some embodiments, the superior biological or physiological property associated with the humanized internalizing moieties or fragments described herein is that the humanized internalizing moiety or antigen-binding fragment is associated with a specific pattern of glycosylation in a cell type that differs from the glycosylation pattern of the non-humanized or alternative internalizing moiety or antigen-binding fragment in the same type of cell. For example, the humanized internalizing moiety or antigen-binding fragment may be hemi-glycosylated in a cell type while the non-humanized or alternative internalizing moiety or antigen-binding fragment is not hemi-glycosylated in the same type of cell. In some embodiments, the superior biological or physiological property associated with the humanized internalizing moieties or fragments described herein is that the humanized internalizing moiety or antigen-binding fragment is post-translationally modified with a specific glycosylation group in a cell type that differs from the post-translational modification of the non-humanized or alternative internalizing moiety or antigen-binding fragment in the same type of cell. The skilled worker is aware of routine experiments that may be utilized for testing the glycosylation patterns of the humanized internalizing moieties or fragments thereof. Examples of experiments for testing the glycosylation levels and patterns of the internalizing moieties and fragments thereof include protocols described in Mohammad, 2002, Protein Protocols Handbook, pages 795-802; standard procedures involving mass spectrometry and/or HPLC; GLYCO-PRO™ (Sigma-Aldrich); and Qproteome Total Glycoprotein Kit™ (Qiagen, Valencia, Calif.). In order to identify the exact sites of glycosylation in a protein sequence, standard endoproteinase cleavage may be performed (e.g. tryptic digest) followed by analysis by LC/MS or HILIC-MS/MS, similar to the protocols described in Zauner G et al., 2010, J Sep Sci., 33:903-10.

In some embodiments, the superior biological or physiological property associated with the humanized internalizing moieties or fragments of the disclosure described herein is that the humanized internalizing moiety or antigen-binding fragment is associated with reduced deamidation in a physiologically acceptable carrier as compared to deamidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less deamidation in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with reduced deamidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the deamidation of the humanized internalizing moieties or fragments thereof. Examples of assays for testing protein deamidation include commercially available deamidation assays such as the ISOQUANT® Isoaspartate Detection Kit (Promega, Madison Wis.) or Dionex UltiMate 3000 Titanium System (Dionex, Sunnyvale, Calif.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced oxidation in a physiologically acceptable carrier as compared to oxidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less oxidation in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with reduced oxidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the oxidation of the humanized internalizing moieties or fragments thereof. For example, oxidation levels may be assessed by using any one of several commercially available oxidation assays, such as the Methionine Sulfoxide Immunoblotting Kit (Cayman Chemical, Ann Arbor, Mich.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced lipidation when produced in a cell type as compared to the lipidation of the non-humanized or alternative antibody or fragment when produced in the same type of cell. In other embodiments, the superior biological or physiological property associated with the humanized internalizing moieties or fragments described herein is that the humanized internalizing moiety or antigen-binding fragment is associated with increased lipidation when produced in a cell type as compared to the lipidation of the non-humanized or alternative antibody or antigen-binding fragment when produced in the same type of cell. In some embodiments, the superior biological or physiological property associated with the humanized internalizing moieties or fragments described herein is that the humanized internalizing moiety or antigen-binding fragment is associated with a specific pattern of lipidation when produced in a cell type that differs from the lipidation pattern of the non-humanized or alternative internalizing moiety or antigen-binding fragment when produced in the same type of cell. In some embodiments, the superior biological or physiological property associated with the humanized internalizing moieties or fragments described herein is that the humanized internalizing moiety or antigen-binding fragment is post-translationally modified with a specific lipidation group when produced in a cell type that differs from the post-translational modification of the non-humanized or alternative internalizing moiety or antigen-binding fragment when produced in the same type of cell. The skilled worker is aware of routine experiments that may be utilized for testing the lipidation patterns of the humanized internalizing moieties or fragments thereof. For example, the internalizing moieties or fragments thereof may be assessed by the protocols described in Gelb et al., 1999, Protein Lipidation Protocols, Humana Press, pages 1-256.

In some embodiments, the superior biological or physiological property associated with the humanized internalizing moieties or fragments of the disclosure described herein is that the humanized internalizing moiety or antigen-binding fragment is capable of binding a polynucleotide (e.g., DNA) with higher affinity (lower $K_D$) as compared to the binding affinity of the non-humanized, parent antibody or an alternative antibody or fragment, such as a different humanized antibody. In some embodiments, the humanized internalizing moiety or fragment is associated with at least 5%, 10%, 25%, 50%, 75%, 100%, 150%, 200% or 300% stronger binding affinity for a polynucleotide (e.g., DNA; double stranded blunt DNA) as compared to a non-humanized or alternative internalizing moiety or antigen-binding fragment in the same type of physiologically acceptable carrier. The skilled worker is aware of routine experiments that may be utilized for testing the binding affinity ($K_D$) of the humanized internalizing moieties or fragments thereof. Binding affinity can be measured using Surface Plasmon Resonance (SPR) or Quartz Crystal Microbalance (QCM), in accordance with currently standard methods and the manufacturer's protocols.

III. Heterologous Agents

In some embodiments, an antibody or antigen-binding fragment, as described herein (e.g., a humanized antibody or antigen-binding fragment thereof of the present disclosure) is not conjugated to a heterologous agent (e.g., a chemotherapeutic agent), particularly a toxic or therapeutic heterologous agent. In other embodiments, an antibody or antigen-binding fragment, as described herein (e.g., a humanized antibody or antigen-binding fragment thereof of the present disclosure) may be conjugated to a heterologous agent (e.g., a chemotherapeutic agent). Accordingly, the disclosure provides conjugates comprising an antibody or antigen-binding fragment of the disclosure associated with a heterologous agent. By heterologous, it is meant that the agent is not itself a portion of the antibody or antigen binding fragment and/or is not a natural, endogenous target of the antibody or antigen binding fragment. In certain embodiments, the heterologous agent is conjugated to the antibody or antigen binding fragment (e.g., the two portions are joined by a covalent bond, such as via co-translational fusion or chemical conjugation).

In some embodiments, the heterologous agent is a polypeptide or peptide. In other embodiments, the heterologous agent is a polynucleotide (e.g., comprises a nucleic acid, such as DNA or RNA, including antisense DNA or RNA). In other embodiments, the heterologous agent is a small organic molecule. In certain embodiments, the polypeptide, peptide, or polynucleotide is a therapeutic agent. In certain embodiments, the small organic molecule is a therapeutic agent. In other embodiments, the heterologous agent is a toxin.

In other embodiments, the heterologous agent is a radionucleide or other detectable label. Exemplary radionucleides and detectable labels facilitate visualization or localization of a conjugate in vivo or in vitro, and thus, facilitate diagnostic use as well as in vitro studies using conjugates of the disclosure.

In some embodiments, the heterologous agent is a polynucleotide. In some embodiments, the polynucleotide is administered to a cell as a form of gene therapy. In some embodiments, the polynucleotide increases the expression of a gene already expressed in the cell. In some embodiments, the polynucleotide is a wildtype copy of a gene, and the cell expresses a mutant copy of the gene. In some embodiments, the polynucleotide is a mutant copy of a gene. In some embodiments, the polynucleotide is a mutant copy of a gene, and the cell expresses a wildtype copy of the gene. In some embodiments, the polynucleotide is a mutant copy of a gene, and the cell expresses a mutant copy of the gene. In some embodiments, the polynucleotide is an antisense molecule. In some embodiments, the polynucleotide is an RNAi molecule. In particular embodiments, the polynucleotide is an siRNA molecule. In some embodiments, the polynucleotide is one or both of trRNA and/or crRNA for use in CRISPR technology. In some embodiments, the polynucleotide is a synthetic single guide RNA (sgRNA). See, e.g., Jinek, M., et al. (2012) Science, 337, 816-821. In some embodiments, the trRNA, crRNA and/or sgRNA are administered in combination with a Cas9 protein or a polynucleotide encoding a Cas9 protein. In some embodiments, the Cas9 protein or polynucleotide encoding the Cas9 protein is administered to a cell by means of any of the internalizing moieties described herein. In some embodiments, the Cas9 protein has a D10A and/or an H840A mutation. In some embodiments, the polynucleotide encodes for a Cas9 protein having a D10A and/or an H840A mutation. See, e.g., Cong L., et al. (2013) Science, 339, 819-823; Jinek, M., et al. (2012) Science, 337, 816-821; Gasiunas, G., et al. (2012) Proc. Natl. Acad. Sci. USA, 109, E2579-2586; and Mali, P., et al. (2013) Science, 339, 823-826; each of which is incorporated by reference herein in its entirety. In some embodiments, any of the internalizing moieties described herein is conjugated to a Cas9 protein having both a D10A and H840A mutation, and in some embodiments, this mutant Cas9 protein may be used to target protein domains for transcriptional regulation (Perez-Pinera, P., et al. (2013) Nat. Methods, 10, 239-242., Mali, P., et al. (2013) Nat. Biotechnol. 31, 833-838; Cheng, A. W., et al. (2013) Cell Res. 23, 1163-1171), epigenetic modification (Hu, J., et al. (2014) Nucleic Acids Res. doi:10.1093/nar/gku109), and microscopic visualization of specific genome loci (Chen, B., et al. (2013) Cell, 155, 1479-1491).

In some embodiments, the heterologous agent is a chemotherapeutic agent. Exemplary chemotherapeutic agent agents are known in the art. In some embodiments, the chemotherapeutic agent is an RNA polymerase inhibitor, hydroxyureataxanes (such as paclitaxel and doxetaxel) and/or anthracycline antibiotics; alkylating agents; alkyl sulfonates; aziridines; ethylenimines and methylarnelamines; acetogeains; delta-9-tetrahydrocannabinol; beta-lapachone; lapachol; colchicines; betulinic acid; a camptothecin; bryostatin; callystatin; CC-1065; podophyllotoxin; podophyllinic acid; teniposide; cryptophycins; dolastatin; duocarmycin; eleutherobin; pancratistatin; a sarcodictyin; spongistatin; nitrogen mustards; nitrosureas; antibiotics; folic acid analogues; purine analogs; pyrimidine analogs; androgens; anti-adrenals; folic acid replenisher; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids; mitoxantrone; mopidanmol; nitraerine; pentostatin; phenamet; pirarubicin; losoxantrone; 2-ethylhydrazide; procarbazine; PSK(R)

polysaccharide complex; razoxane; rhizoxin; sizofiran; spirogermanium; tenuazonic acid; triaziquone; 2,2',2''-trichlorotriethyiamine; trichothecenes; urethan; vindesine; dacarbazine; mannomustine; mitobronitol; mitolactol; pipobroman; gacytosine; arabinoside ("Ara-C"); thiotepa; taxoids; chloranbucil; gemcitabine (GEMZAR®); 6-thioguanine; mercaptopurine; methotrexate; platinum analogs; vinblastine; platinum; etoposide; ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluorometlhylornithine; retinoids; capecitabine; pharmaceutically acceptable salts, acids or derivatives of any of the above.

In some embodiments, the chemotherapeutic agent is a PARP inhibitor. Examples of PARP inhibitors include iniparib, talazoparib, olaparib, rucaparib, veliparib (ABT-888), CEP-9722, MK 4827, BGB 290 and 3-aminobenzamide.

In other embodiments, chemotherapeutic agents are antihormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON®toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RFVISOR® vorozole, FEMARA® letrozole, and ARIMDDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTTN® vaccine, and VAXID® vaccine; LURTOTECAN® topoisomerase 1 inhibitor; ABARELDC® rmRH; lapatinib ditosylate (an ErbB-2 and EGFR dual tyrosine kinase small-molecule inhibitor also known as GW572016); and pharmaceutically acceptable salts, acids or derivatives of any of the above.

In some embodiments, the chemotherapeutic agent is a growth inhibitor agent. A "growth inhibitory agent" when used herein refers to a compound or composition which inhibits growth of a cell. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase H inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995). The taxanes or hydroxyureataxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). These molecules promote the assembly of microtubules from tubulin dimers and stabilize microtubules by preventing depolymerization, which results in the inhibition of mitosis in cells.

In some embodiments, chemotherapeutic agents are enzymatically active toxins and fragments thereof that include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyapates (such as tolyene 2,6-diisocyanate), and bis-active fluorine compounds (such as 1,5-difluoro-2,4-dinitrobenzene). For example, a ricin immunotoxin can be prepared as described in Vitetta et aL, Science, 238: 1098 (1987). Carbon-14-labeled 1-isothiocyanatobenzyI-3-methyldiethylene triaminepentaacetic acid (MX-DTPA) is an exemplary chelating agent for conjugation of radionucleotide to the antibody. See WO94/11026.

In some embodiments, the heterologous agent is a DNA-damaging compound. In some embodiments, the DNA-damaging compound is a DNA cross-linker (e.g., a platin such as cisplatin, carboplatin, oxaliplatin or an active analog thereof), an inhibitor of DNA synthesis (e.g., methotrexate or an active analog thereof), a topoisomerase poison (e.g., doxorubicin, daunorubicin, or an active analog thereof), a DNA alkylating agent (e.g., a nitrosurea, triazene compound or an active analog thereof), and/or an antimetabolite (e.g., a pyrimidine analog such as 5-fluorouracil or an active analog thereof).

In some embodiments, conjugation between the antibody or antigen-binding fragment (e.g., a humanized antibody or antigen-binding fragment thereof of the disclosure) and the heterologous agent is accomplished by generating a fusion protein containing a heterologous agent polypeptide and an internalizing moiety, expressed as one contiguous polypeptide chain. It is recognized that, in the case of conjugation of a full length antibody or Fab, the final product comprises more than one polypeptide chain, but the heterologous agent may be covalently associated (e.g., produced as an inframe, co-translational fusion) to one of the chains, such as the heavy chain. In either case, such polypeptides are referred to herein as being recombinantly conjugated or as comprising a fusion protein. This is one example of conjugation (e.g., interconnection; association) between an antibody or antigen-binding fragment and a heterologous agent. In preparing such fusion proteins, a fusion gene is constructed comprising nucleic acids which encode a heterologous agent polypeptide and an internalizing moiety, and optionally, a peptide linker sequence to span the heterologous agent polypeptide and the internalizing moiety. The disclosure contemplates that suitable complexes, such as fusion proteins, may be in either orientation. In other words, the humanized antibody or antigen-binding fragment thereof portion may be N-terminal or C-terminal to the heterologous agent. When the final product comprises one that one polypeptide chain that, for example, an antibody where the heavy and light chains associate following expression in host cells, the disclosure contemplates that the heavy and light chains (optionally with heterologous agent expressed as a fusion protein with, for example the heavy chain) may be expressed from a single vector or from a set of vectors expressed in the same host cell.

In certain specific embodiments, conjugates for use in the methods of the present disclosure can be produced by using a universal carrier system. For example, a heterologous agent polypeptide can be conjugated to a common carrier such as protein A, poly-L-lysine, hex-histidine, and the like. The conjugated carrier will then form a complex with an antibody which acts as an internalizing moiety, e.g., the humanized antibody or antigen-binding fragment thereof of the present disclosure. A small portion of the carrier molecule that is responsible for binding immunoglobulin could be used as the carrier.

In some embodiments, a humanized antibody or antigen-binding fragment of the disclosure is chemically conjugated to the heterologous agent. In certain embodiments, the humanized antibody or antigen-binding fragment thereof is chemically conjugated using well-known cross-linking reagents and protocols. For example, there are a large number of chemical cross-linking agents that are known to those skilled in the art and useful for cross-linking the heterologous agent with the humanized antibody or antigen-binding fragment thereof. For example, the cross-linking agents may be heterobifunctional cross-linkers, which can be used to link molecules in a stepwise manner. Examples of representative cross-linking agents, including representative heterobifunctional cross-linkers, are provided herein.

The foregoing is exemplary. Numerous methods exist to conjugate or otherwise join an antibody or antigen binding fragment of the disclosure to a heterologous agent, regardless of whether that heterologous agent is a protein, peptide, polynucleotide, or small molecule (e.g., a chemotherapeutic agent small molecule). One of skill in the art can select the appropriate scheme to associate an antibody or antigen binding fragment of the disclosure with a heterologous agent, including doing so directly or via a linker (e.g., a polypeptide or other linker).

As described above, the disclosure contemplates that a heterologous agent suitable for conjugation to an antibody or antigen binding fragment of the disclosure may be a polypeptide, peptide, small molecule (e.g., small organic or inorganic molecules such as a chemotherapeutic agent small molecule), or polynucleotide (e.g., nucleic acid, such as DNA or RNA).

IV. Conjugates

In certain embodiments, any of the internalizing moieties disclosed herein is not conjugated to a heterologous agent. In other embodiments, the disclosure provides conjugates of the disclosure. Conjugates of the disclosure comprise (i) an antibody or antigen binding fragment of the disclosure associated with (fused or otherwise conjugated to) (ii) a heterologous agent, particularly a therapeutic or toxic heterologous agent. Conjugates of the disclosure and for use in the present disclosure can be made in various manners. In certain embodiments, the heterologous agent is a polypeptide, and the C-terminus of a heterologous agent can be linked to the N-terminus of a humanized internalizing moiety. Alternatively, the C-terminus of a humanized internalizing moiety can be linked to the N-terminus of the heterologous agent. For example, conjugates can be designed to place the heterologous agent at the amino or carboxy terminus of either the antibody (or antibody fragment) heavy or light chain. In certain embodiments, potential configurations include the use of truncated portions of an antibody's heavy and light chain sequences (e.g., 3E10) as needed to maintain the functional integrity of the attached heterologous agent. Further still, the internalizing moiety can be linked to an exposed internal (non-terminus) residue of the heterologous agent. In further embodiments, any combination of the heterologous agent-internalizing moiety configurations can be employed, thereby resulting in an heterologous agent: internalizing moiety ratio that is greater than 1:1 (e.g., two heterologous agent molecules to one internalizing moiety).

In certain embodiments, the conjugates comprise a "AGIH" portion (SEQ ID NO: 28) on the N-terminus of the polypeptide, and such conjugates may be provided in the presence or absence of one or more epitope tags. In further embodiments, the chimeric polypeptide comprises a serine at the N-terminal most position of the polypeptide. In some embodiments, the conjugates comprise an "SAGIH" (SEQ ID NO: 29) portion at the N-terminus of the polypeptide, and such conjugates may be provided in the presence or absence of one or more epitope tags.

In some embodiments (e.g., when the heterologous agent is a peptide or polypeptide), the heterologous agent and the internalizing moiety may be conjugated directly to each other. Alternatively, they may be linked to each other via a linker sequence, which separates the heterologous agent and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the heterologous agent polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 15 amino acids can be used to provide a suitable separation of functional protein domains, although longer or shorter linker sequences may also be used. The length of the linker sequence separating the heterologous agent and the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the heterologous agent to an internalizing moiety can be a constant domain of an antibody (e.g., constant domain of Ab 3E10 or all or a portion of an Fc region of another antibody). By way of example, the linker that joins heterologous agent with an internalizing moiety may be GSTSGSGKSSEGKG (see, e.g., SEQ ID NO: 31). In certain embodiments, the linker is a cleavable linker. As noted above, the conjugate may include more than one linker, such as a linker joining the internalizing moiety to the heterologous agent and a linker joining portions of the internalizing moiety to each other (e.g., a linker joining a VH and VL domain of a single chain Fv fragment). When the conjugate includes more than one linker, such as two linkers, the linkers are independently selected and may be the same or different.

In certain embodiments, the conjugates for use in the methods of the present disclosure can be generated using well-known cross-linking reagents and protocols. For example, there are a large number of chemical cross-linking agents that are known to those skilled in the art and useful for cross-linking the heterologous agent with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HC1 (DMP) are examples of useful homobifunctional cross-linking agents, and bis-[B-(4-azidosalicylamido)ethyl]disulfide (BASED) and N-succinimidyl-6(4'-azido-2'-nitrophenylamino) hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with—SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, conjugates for use in the methods of the present disclosure can be produced by using a universal carrier system. For example, a heterologous agent polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, conjugates for use in the methods of the present disclosure can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of a heterologous agent to an internalizing moiety, a cleavable domain or cleavable linker can be used. Cleavage will allow separation of the internalizing moiety and the heterologous agent. For example, following penetration of a cell by a conjugate, cleavage of the cleavable linker would allow separation of the heterologous agent from the internalizing moiety.

In certain embodiments, the conjugates for use in the methods of the present disclosure are generated as a fusion protein containing a heterologous agent polypeptide and an internalizing moiety, expressed as one contiguous polypeptide chain. Such conjugates are referred to herein as recombinantly conjugated. In preparing such fusion proteins, a fusion gene is constructed comprising nucleic acids which encode a heterologous agent polypeptide and an internalizing moiety, and optionally, a peptide linker sequence to span the heterologous agent polypeptide and the internalizing moiety. Alternatively, one or more portions of the conjugate may be recombinantly produced separately, and the portions may be later combined chemically or recombinantly. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The conjugates encoded by the fusion gene may be recombinantly produced using various expression systems as is well known in the art (also see below).

Recombinantly conjugated conjugates include embodiments in which the heterologous agent polypeptide is conjugated to the N-terminus or C-terminus of the internalizing moiety.

In some embodiments, the immunogenicity of the conjugate may be reduced by identifying a candidate T-cell epitope within a junction region spanning the conjugate and changing an amino acid within the junction region as described in U.S. Patent Publication No. 2003/0166877.

V. Nucleic Acids and Expression

In certain embodiments, the present disclosure makes use of nucleic acids for producing any of the antibodies or antigen-binding fragments of the disclosure (e.g., humanized internalizing moieties or fragments thereof), or any of the conjugates disclosed herein.

The nucleic acids may be single-stranded or double-stranded, DNA or RNA molecules. In further embodiments, the humanized internalizing moiety or fragment thereof nucleic acid sequences can be isolated, recombinant, and/or fused with a heterologous nucleotide sequence, or in a DNA library.

In certain embodiments, humanized internalizing moieties or fragments thereof nucleic acids also include nucleotide sequences that hybridize under highly stringent conditions to a polynucleotide encoding any of the above-mentioned humanized internalizing moieties or fragments thereof nucleotide sequence, or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the humanized internalizing moieties or fragment thereof nucleic acids due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant humanized internalizing moieties or fragments thereof and/or conjugate encoding nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a humanized internalizing moieties or fragments thereof and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This disclosure also pertains to a host cell transfected with a recombinant gene which encodes a humanized internalizing moieties or fragment thereof or a conjugate for use in the methods of the disclosure. The host cell may be any prokaryotic or eukaryotic cell. For example, a humanized internalizing moiety or fragment thereof or a conjugate may be expressed in bacterial cells such as *E. coli*, insect cells (e.g., using a baculovirus expression system), yeast, or mammalian cells. Other suitable host cells are known to those skilled in the art. In some embodiments, the host cell is immortalized or is stably transfected to express a vector. The present disclosure also provides for a method of producing a polypeptide (e.g., any of the antibodies or antigen binding fragments described herein), comprising providing the host cell and culturing the host cells under suitable condition to produce the polypeptide.

The present disclosure further pertains to methods of producing a humanized internalizing moiety or fragment thereof, an internalizing moiety, and/or a conjugate for use in the methods of the disclosure. For example, a host cell transfected with an expression vector encoding a humanized internalizing moiety or fragment thereof or a conjugate can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides. In a preferred embodiment, the polypeptide is a fusion protein, and may optionally contain a domain which facilitates its purification.

A recombinant humanized internalizing moiety or fragment thereof (or other antibody or antigen-binding fragment of the disclosure) nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2 gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, $2^{nd}$ Ed., ed. By Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

It should be understood that conjugates can be made in numerous ways. For example, a humanized internalizing moiety (or fragment thereof) and a heterologous agent can be made separately, such as recombinantly produced in two separate cell cultures from nucleic acid constructs encoding their respective proteins. Once made, the proteins can be chemically conjugated directly or via a linker. By way of another example, the conjugate can be made as an inframe fusion in which the entire conjugate, optionally including one or more linkers, and optionally including one or more epitope tags, is made from a nucleic acid construct that includes nucleotide sequence encoding both the heterologous agent and the internalizing moiety. By way of another example, the conjugate comprises: a) a humanized internalizing moiety (or fragment thereof) that comprises a light chain variable ($V_L$) domain (e.g., SEQ ID NO: 8) that is fused to a heavy chain variable ($V_H$) domain (e.g., SEQ ID NO: 10) by means of an inframe fusion; and b) a heterologous agent; wherein the humanized internalizing moiety and the heterologous agent are conjugated together by means of a universal carrier system or by means of chemical conjugation.

Antibodies of the disclosure, provided alone or as a conjugate with a heterologous agent, have numerous uses, including in vitro and in vivo uses. In vivo uses include not only therapeutic uses but also diagnostic and research uses in, for example, animal models of a particular disease. By way of example, conjugates of the disclosure may be used as research reagents and delivered to animals to understand bioactivity, localization and trafficking, protein-protein interactions, enzymatic activity, and impacts of the heterologous agent on animal physiology in healthy or diseases animals.

Conjugates may also be used in vitro to evaluate, for example, bioactivity, localization and trafficking, protein-protein interactions, and enzymatic activity of the heterologous agent in cells in culture, including healthy and diseased cells (e.g., cancer cells) in culture. The disclosure contemplates that conjugates comprising (i) an antibody or antigen binding fragment of the disclosure and (ii) a heterologous agent (e.g., such as conjugates comprising an antibody or antigen binding fragment of the disclosure and a heterologous protein or peptide) may be used to deliver the heterologous agent to cytoplasm, lysosome, and/or autophagic vesicles of cells, including cells in culture.

VI. Methods of Administration

Various delivery systems are known and can be used to administer the internalizing moieties of the disclosure, such as antibodies or antigen-binding fragments of the disclosure (whether provided alone or as a conjugate with another agent) (any one or more of which may be referred to as "compositions of the disclosure" or "humanized compositions of the disclosure"), e.g., various formulations, encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, and oral routes. In particular embodiments, parenteral introduction includes intramuscular, subcutaneous, intravenous, intravascular, and intrapericardial administration.

The present disclosure provides systemic delivery of one or more doses of antibodies or antigen-binding fragments of the disclosure (whether provided alone or as a conjugate with another agent) (any one or more of which may be referred to as "compositions of the disclosure" or "humanized compositions of the disclosure"). Systemic delivery includes, for example, subcutaneous, intravenous, or intramuscular.

The antibodies or antigen binding fragments of the disclosure, including those internalizing moieties or fragments thereof conjugated to heterologous agents, may be administered by any convenient route, for example, by infusion or bolus injection.

In certain embodiments, antibodies or antigen binding fragments of the disclosure, including those conjugated to heterologous agents, are administered by intravenous infusion. In certain embodiments, the conjugates are infused over a period of at least 10, at least 15, at least 20, or at least 30 minutes. In other embodiments, antibodies or antigen binding fragments of the disclosure (provided alone or as a conjugate with heterologous agent) are infused over a period of at least 60, 90, or 120 minutes. Regardless of the infusion period, the disclosure contemplates that each infusion is part of an overall treatment plan where a composition of the disclosure is administered according to a regular schedule (e.g., weekly, monthly, etc.).

The composition and route of administration is chosen depending on the particular use of the technology. For example, a different composition and/or route of administration may be appropriate when using the compositions of the disclosure for research purposes, such as in vitro or in an animal model, versus when using for diagnostic or therapeutic purposes in human patients. One of skill in the art can select the appropriate route of administration depending on the particular application of the technology.

The amount of the compositions of the disclosure for use in the methods of the present disclosure can be determined by standard clinical techniques and may vary depending on the particular indication or use. Effective doses may be extrapolated from dose-response curves derived from in vitro or animal model test systems.

Dosages may be readily determined by techniques known to those of skill in the art or as taught herein. Toxicity and therapeutic efficacy of any of the internalizing moieties disclosed herein may be determined by standard pharmaceutical procedures in experimental animals.

In some embodiments, each dose administered to a subject having a tumor is equivalent to a dose of less than or of about 1 mg/kg, 5 mg/kg, 10 mg/kg, 15 mg/kg, 20 mg/kg, 25 mg/kg, 30 mg/kg or 35 mg/kg. Guidance for deriving a human equivalent dose (HED) from a dose effective in treating a mouse is provided, for example, in the July 2005 U.S. Food and Drug Administration's Guidance for Industry: Estimating the Maximum Safe Starting Dose in Initial Clinical Trials for Therapeutics in Adult Healthy Volunteers. In some embodiments, any of the antibodies or antigen binding fragments described herein is administered to a human subject at a dose of less than or about 20 mg/kg, 15 mg/kg, 10 mg/kg, 5 mg/kg, 3 mg/kg, less than 1.5 mg/kg, less than 2 mg/kg, less less than 1.5 mg/kg, less than 1 mg/kg, or less than or equal to 0.8 mg/kg (e.g., where each dose of a multi-dose regiment may be at this dosage).

VII. Pharmaceutical Compositions

In certain embodiments, internalizing moieties of the disclosure, such as antibodies or antigen-binding fragments of the disclosure (whether provided alone or as a conjugate with another agent) (any one or more of which is referred to as "compositions of the disclosure" or "humanized compositions of the disclosure") are formulated with a pharmaceutically acceptable carrier. For example, the disclosure provides a composition comprising an antibody or antigen-binding fragment of the disclosure (optionally conjugated to another agent) formulated with one or more pharmaceutically acceptable carriers and/or excipients. One or more such compositions of the disclosure (whether provided alone or as a conjugate with another agent) can be administered alone or as a component of a pharmaceutical formulation (composition). The compositions of the disclosure (whether provided alone or as a conjugate with another agent) may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the disclosure include those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining the therapeutic agent and a carrier and, optionally, one or more accessory ingredients. In general, the formulations can be prepared with a liquid carrier, or a finely divided solid carrier, or both, and then, if necessary, shaping the product.

Pharmaceutical compositions suitable for parenteral administration may comprise one or more compositions of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers (e.g., HEPES buffer), bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the present disclosure, the compositions of the disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The foregoing applies to any of the compositions and methods described herein. The disclosure specifically contemplates any combination of the features of compositions of the present disclosure (alone or in combination) with the features described for the various pharmaceutical compositions and route of administration described in this section.

VII. Methods of Treatment

For any of the methods described herein, the disclosure contemplates the use of any of the compositions of the disclosure (whether alone or in combination with any of the heterologous agents or additional therapeutic treatments disclosed herein). Compositions of the disclosure may be described based on any combination of structural and/or functional features provided herein. In addition, for any of the methods described herein, the disclosure contemplates the combination of any step or steps of one method with any step or steps from another method. In certain embodiments, the antibodies or antigen-binding fragments are not conjugated to any heterologous agent or to any therapeutic or toxin heterologous agent. In other embodiments, the internalizing moieties are conjugated to a heterologous agent. The internalizing moieties conjugated to a heterologous agent can be used in methods of treatment and/or in methods of delivering a heterologous agent into cells in vitro or in vivo (e.g., such as to a human subject). These methods involve administering to an individual in need thereof an effective amount of a compound of the disclosure appropriate for the particular disease or condition. In specific embodiments, these methods involve delivering any of the antibodies or antigen binding fragments disclosed herein to the cells of a subject in need thereof.

In certain embodiments, the disclosure provides methods of treating a cancer or tumor in a subject, comprising administering an effective amount of any of the internalizing moieties disclosed herein (alone or in combination with any of the heterologous agents or additional therapeutic treatments disclosed herein), to a subject in need thereof according to a dosing regimen (e.g., a dose and dosing schedule) and/or dosing schedule effective to, e.g., treat the cancer or tumor in the subject, ameliorate one or more symptoms of the cancer or tumor; and/or reduce growth, proliferation or survival of the cancer or tumor.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

In certain embodiments of any of the foregoing, the disclosure provides a method of treating a tumor or cancer cell with any of the internalizing moieties described herein (alone or in combination with any of the heterologous agents or additional therapeutic treatments disclosed herein). In some embodiments, the tumor or cancer cell is present in a tumor or cancer tissue. In some embodiments, the tumor or cancer cell or tumor or cancer tissue is present in a subject. In some embodiments, the subject is a human. In some embodiments, the tumor or cancer cell is a malignant tumor or cancer cell. Without being bound by theory, the internalizing moieties described herein are, in certain embodiments, capable of any one or more of the following: a) targeting (e.g., delivering) an agent conjugated to the internalizing moiety (e.g., any of the heterologous agents described herein) to a tumor or cancer cell, b) killing and/or decreasing the growth, proliferation, size, survival or migration of a tumor or cancer cell, c) sensitizing a tumor or cancer cell to the effects of any agent conjugated to the internalizing moiety (e.g., a chemotherapeutic agent), and/or d) sensitizing a tumor or cancer cell to the effects of any separately administered agent or therapy (e.g., a chemotherapeutic agent or radiation therapy). In certain embodiments, the internalizing moiety is administered/delivered to cells in the absence of a heterologous agent (e.g., not interconnected to a therapeutic or toxic heterologous agent) or in the absence of a therapeutic heterologous agent. For example, in certain embodiments, an internalizing moiety is administered to cells in the absence of a heterologous agent for delivery into a tumor or cancer cell. In other embodiments, the internalizing moiety is conjugated to a heterologous agent (e.g., a chemotherapeutic agent) and administered to a tumor or cancer cell.

Treating a cancer or a tumor in a subject refers to improving (improving the subject's condition), alleviating, delaying or slowing progression or onset, decreasing the severity of one or more symptoms associated with the cancer or tumor. For example, treating a cancerous tumor includes any one or more of: reducing growth, proliferation and/or survival of cancer cells, killing cancer cells (e.g., by necrosis, apoptosis or autophagy), decreasing tumor size, decreasing rate of tumor size increase, halting increase in tumor size, decreasing the number of metastases, decreasing pain, increasing survival, and increasing progression free survival.

In some embodiments, any of the internalizing moieties of the disclosure are capable of inducing apoptosis in a tumor or cancer cell. In some embodiments, any of the internalizing moieties of the disclosure are administered to a subject in order to induce apoptosis in the tumor or cancer cell. In certain aspects, the disclosure provides a method of triggering, promoting, inducing and/or increasing apoptosis in a subject in need thereof, such as of cancer cells in such a subject, comprising administering an internalizing moiety (e.g., an antibody or antigen binding fragment thereof of the disclosure) of the disclosure. In certain aspects, the disclosure provides a method of triggering, promoting, inducing and/or increasing apoptosis of cells of a tumor in a subject in need thereof, comprising administering an internalizing moiety (e.g., an antibody or antigen binding fragment thereof of the disclosure) of the disclosure. The disclosure provides, in certain embodiments, that such cancer or tumor is any of the cancers or tumors disclosed herein—characterized based on tissue type or mutational status.

"Diagnosing" refers to the process of identifying or determining the distinguishing characteristics of a disease or tumor. In the case of cancer, the process of diagnosing is sometimes also expressed as staging or tumor classification based on severity or disease progression.

Subjects in need of treatment or diagnosis include those already with a tumor or cancer as well as those prone to having or those in whom a tumor or cancer is to be prevented. For example, a subject or mammal is successfully "treated" for a cancer or tumor if, according to the method of the present disclosure, after receiving a therapeutic amount of an internalizing moiety (alone or in combination with another therapeutic agent), the subject shows observable and/or measurable reduction in or absence of one or more of the following: reduction in the number of tumor cells or absence of such cells; reduction in the tumor size; inhibition (i.e., slow to some extent and preferably stop) of tumor cell infiltration into peripheral organs including the spread of cancer into soft tissue and bone; inhibition (i.e., slow to some extent and preferably stop) of tumor metastasis; inhibition, to some extent, of tumor growth; and/or relief to some extent, of one or more of the symptoms associated with the specific cancer; reduced morbidity and mortality, and improvement in quality of life issues. Reduction of these signs or symptoms may also be felt by the patient. To the extent such internalizing moieties may prevent growth and/or kill existing tumor or cancer cells, the internalizing moiety may be cytostatic and/or cytotoxic. In some embodiments, the internalizing moieties are genotoxic.

In some embodiments, the effects of administration of any of the internalizing moieties disclosed herein (whether alone or in combination with any of the additional therapies described herein) may be determined by assessing the treated subject before and after treatment, and determining whether the treatment has any effect on the tumor or cancer. The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and tests for calcium level and other enzymes to determine the extent of metastasis. CT scans can also be done to look for spread to regions outside of the tumor or cancer. In some embodiments, the subject is assessed by measuring tumor size/volume. In some embodiments, the marker is a marker for cell necrosis or cell apoptosis. In some embodiments, the subject is assessed by magnetic resonance imaging. In some embodiments, the subject is assessed by determining levels or staining patterns of specific markers in a sample from the subject (e.g., a tumor biopsy, blood, urine or stool sample), wherein the marker is associated with the specific tumor or cancer in the subject. In some embodiments, the marker is a marker for cell proliferation, such as Ki67. In some embodiments, the marker is a marker for endothelial cells, such as CD-31. In some embodiments, the marker is a marker for apoptosis, such as RNA or protein of any one or more of Bad, Bax, Bcl-2, Bcl-w, BID, BIM, Caspase3, caspase8, CD40, CD4OL, cIAP-2, cytoC, DR6, Fas, FasL, HSP27, HSP60, HSP70, HTRA, IGF-I, IGF-II, IGFBP-1, IGFBP-2, IGFBP-3, IGFBP-4, IGFBP-5, IGFBP-6, IGF-lsR, livin, p21, p2'7, p53, SMAC, Survivin, sTNF-R1, sTNF-R2, TNF-alpha, TNF-beta, TRAILR-1, TRAILR-2, TRAILR-3, TRAILR-4, and/or XIAP. In some embodiments, the marker for apoptosis is DNA fragmentation (which may be detected, for example, by using agarose gel electrophoresis and determining whether a DNA ladder pattern is present), cell staining patterns (e.g., annexin V staining patterns, TUNEL staining), cell morphological studies, and cell viability assays (e.g., using propidium iodide and/or 7-aminoactinomycin D). Increases in pro-apoptotic markers or decreases in anti-apoptotic markers in tumor or cancer cells treated with any of the internalizing moieties disclosed herein is suggestive that apoptosis is being activated in the tumor or cancer cells.

A "therapeutically effective amount" or "effective amount" of a composition is a predetermined amount calculated to achieve the desired result (e.g., effective in reducing tumor growth, proliferation or survival in a subject). The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. A therapeutically effective amount of compound of this invention is typically an amount such that when it is administered in a physiologically tolerable excipient composition, it is sufficient. Therapeutically effective amounts may be administered according to a dosing schedule.

A "patient," "subject" or "individual" are used interchangeably and refer to either a human or non-human animal. The term includes mammals such as humans.

"Mammal" for purposes of the treatment of, alleviating the symptoms of or diagnosis of a disease (e.g., cancer) refers to any animal classified as a mammal, including humans, domestic and farm animals, and zoo, sports, or pet animals, such as dogs, cats, cattle, horses, sheep, pigs, goats, rabbits, ferrets, etc. In some embodiments, the mammal is human. In some embodiments, the mammal is post-natal. In some embodiments, the mammal is pediatric. In some embodiments, the mammal is adult.

In some embodiments, therapy comprising of administering internalizing moieties may be especially desirable in elderly patients who do not tolerate the toxicity and side effects of chemotherapy well and in metastatic disease where radiation therapy has limited usefulness. In some embodiments, the internalizing moieties of the present disclosure may also be used to alleviate cancers upon initial diagnosis of the disease or during relapse. For therapeutic applications, such internalizing moieties can, in some embodiments, be used in combination with, before or after application of other conventional agents and/or methods for the treatment of a tumor, e.g., hormones, antiangiogens, or radiolabeled compounds, or with surgery, cryotherapy, radiotherapy and/or chemotherapy. In some embodiments, the disclosure provides any of the foregoing methods comprising administering any of the antibodies or antigen-binding fragments of the disclosure.

In some embodiments, the internalizing moieties of the present disclosure may be used to treat a tumor. In certain embodiments, the tumor is a cancer. In some embodiments, the cancer is a cancer of any of the following tissues: skin, lung, breast, blood, liver, kidney, stomach, esophagus, head, neck, brain, eye, mouth, throat, pancreas, testicle, ovary, vagina, penis, prostate, colon, intestine, uterus, urethra, gall bladder, bone, salivary gland, anus, thyroid gland, peripheral nervous system, central nervous system, parathyroid gland, pituitary gland, nose, pharanx, and/or cervix. In some embodiments, the cancer is any one of, but is not limited to: epithelial cancer, head and neck cancer, prostate cancer, bladder cancer, lung cancer (including small cell and non-small cell), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, neuroblastoma, primitive neuroectodermal tumor (including medulloblastoma), glioma, melanoma (e.g., uveal melanoma), or pancreatic cancer. Additional cancer types include cancer of skeletal or smooth muscle, stomach cancer, cancer of the small intestine, cancer of the salivary gland, anal cancer, rectal cancer, thyroid cancer, parathyroid cancer, pituitary cancer, blood and bone marrow cancers (e.g., leukemia, lymphoma, and/or myeloma) and nasopharyngeal cancer. In certain embodiments, the cancer is a solid tumor. In other embodiments, the cancer is a blood cancer. In some embodiments, the disclosure provides any of the foregoing methods comprising administering any of the antibodies or antigen-binding fragments of the disclosure.

In certain embodiments, the disclosure provides a method of treating ovarian cancer in a subject in need thereof by administering any of the internalizing moieties of the present disclosure to the subject. In certain embodiments, the disclosure provides a method of treating colon cancer or colorectal cancer in a subject in need thereof by administering any of the internalizing moieties of the present disclosure to the subject. In certain embodiments, the disclosure provides a method of treating pancreatic cancer in a subject in need thereof by administering any of the internalizing moieties of the present disclosure to the subject. In certain embodiments, the disclosure provides a method of treating a hereditary non-polyposis colon cancer (HNPCC) in a subject in need thereof by administering any of the internalizing moieties of the present disclosure to the subject. In certain embodiments, the disclosure provides a method of treating an adenocarcinoma in a subject in need thereof by administering any of the internalizing moieties of the present disclosure to the subject.

In certain embodiments, the cancer is a primary cancer. In some embodiments, the cancer is a metastatic cancer. In certain embodiments, the cancer is advanced or metastatic cancer. In certain embodiments, administration of antibodies or antigen binding fragments of the disclosure is useful for inhibiting metastases. In some embodiments, the disclosure provides any of the foregoing methods comprising administering any of the antibodies or antigen-binding fragments of the disclosure.

In some embodiments, the internalizing moieties of the present disclosure are used to treat a tumor or cancer that has a DNA repair mutation (e.g., a mutation in BRAF, BRCA2, and/or PTEN). In some embodiments, the internalizing moieties are used to treat a cancer or tumor that is associated with larger than normal insertion-deletion loops (IDLs) as a result of the DNA repair mutation (e.g., a cancer or tumor having IDLs similar to HT-29 colon cancer cells). In some embodiments, the internalizing moieties are used to treat a tumor or cancer in which DNA damage has been induced by treatment with either radiotherapy or with a chemotherapeutic agent. In some embodiments, the disclosure provides any of the foregoing methods comprising administering any of the antibodies or antigen-binding fragments of the disclosure.

In some embodiments, the internalizing moieties of the disclosure are useful for treating a tumor or cancer that does not have a mutation in a DNA repair gene (e.g., a mutation in BRAF, BRCA2, and/or PTEN). In some embodiments, the internalizing moiety has a mutation in a DNA repair gene either does not express the encoded DNA repair protein or expresses a lower level of functional In some embodiments, the internalizing moieties are used to treat a cancer or tumor that is associated with a mutation in a tumor suppressor gene (e.g., TP53). In some embodiments, the internalizing moieties are used to treat a cancer or tumor that is associated with a mutation in a gene encoding a protein involved in transcription or translation. In some embodiments, the internalizing moieties are used to treat a cancer or tumor that is associated with an RNA polymerase mutation (e.g., a mutation in the POLR2A gene). In some embodiments, the internalizing moities are used to treat a cancer or tumor that is associated with a mutation in any one or more of the following proteins: KRAS, CDKN2A/p16, SMAD4/DPC4, PIK3CA, and/or APC.

In some embodiments, the internalizing moieties are used to treat a cancer or tumor caused by similar mutations as those resulting in the cancerous phenotype associated with the SW837 or SW480 cancer cell lines. In some embodiments, the disclosure provides any of the foregoing methods comprising administering any of the antibodies or antigen-binding fragments of the disclosure. In some embodiments, the internalizing moieties are used to treat a cancer or tumor caused by similar mutations as those resulting in the cancerous phenotype associated with the SW780, MCF7, HSF78T, T47D, MDAMB231, BT-549, NIC/ADR-RES, PC-3, DU-145, 786-0, A498, ACHN, CAKI-1, RXF-393, SN12C, TK-10, UO-31, A2780, IGR-OV1, OVCAR-3, OVCAR-4, OVCAR-5, OVCAR-8, SKOV-3, TOV-21G, UACC-62, UACC-257, SK-MEL-1, M14, CaCO2, WiDr, SW48, HCT8, HCT15, SW837, SW403, SW480, HCT-116, HT-29, AsPC-1, CD18, EPP85-181P, EPP85-181RDB, PANC-1, CAPAN-1, AGC, BON, EPG85-257P, KATO III, TMK-1, HeLa, RL95-2, SiHa, BEL-7402, HA22T, Hep3B, HepG2, HLF, 6647, HOS-1, MG-63, PDE02, SaOs-2, SW872, BFTC905, EJ, J82, RT112, T42, TSGH8301, ES-2, PEO1, HT-29, DLD1, U251, CCD-18Co, HC-59, SF-295, SK-N-AS, U87 MG, U251, BT474, HCC-1806, HCC-1954, JIMT-1, MCF-7, MDA-MB-231, CL-34, COLO 205, HCT 116, HCT-15, HT-29, LoVo, LS-174T, LS411N, RKO, SW48, SW480, SW620, N87, SNU-5, FaDu, HL-60, K-562, MOLM-13, MOLT-4, MV4-11, SET2, Hep3B, HuH-7, SNU-398, A-427, A549, Calu-6, H1299, H1975, H226, H292, H460, H520, H522, H647, H727, H810, HCC-44, NCI-H2122, SK-MES-1, H69, H82, H211, H526, SHP-77, DMS 114, Daudi, DoHH-2, Granta 519, JEKO-1, Namalwa, Raji B, Ramos, REC-1, RL, SU-DHL-4, WSU-DLCL2, MSTO-211H, MSTO-211H, H929, OPM-2, RPMI 8226, BxPc-3, HPAC, KP4, MIA PaCa-2, 22Rv.1, PC3, 786-0, G-401, G-402, HT-1080, SJSA-1, 8505C, FTC-238, ECC-1, and/or MFE-280 cancer cell lines. In some embodiments, the disclosure provides any of the foregoing methods comprising administering any of the antibodies or antigen-binding fragments of the disclosure.

In some embodiments, any of the internalizing moieties of the disclosure are for use in treating a tumor or cancer, wherein the tumor or cancer is resistant to treatment with DNA repair inhibitors. In some emdodiments, the internalizing moieties are for use in treating a tumor or cancer associated with microsatellite instability. In some embodiments, the internalizing moities are for use in treating a tumor or cancer having deficient DNA mismatch repair. In some embodiments, the internalizing moieties are for use in treating a tumor or cancer having a mutation in the hMSH2, MSH6 or hMLH1 genes. In some embodiments, the internalizing moities are for use in treating a hereditary non-polyposis colon cancer (HNPCC). In some embodiments, the disclosure provides any of the foregoing methods comprising administering any of the antibodies or antigen-binding fragments of the disclosure.

In some embodiments, the internalizing moieties of the disclosure are for use in promoting collapse of tumor capillary blood vessels in a tumor. In some embodiments, the internalizing moieties promote the disruption of tumor architecture. In some embodiments, the disruption of tumor architecture sensitizes the tumor to an additional therapeutic treatment. In some embodiments, the internalizing moieties are for use in inhibiting Ki-67 expression in a tumor. In some embodiments, the internalizing moieties are for use in inhibiting CD-31 expression in a tumor. In some embodiments, the tumor is a cancer. In some embodiments, the tumor is in a subject. In some embodiments, the subject is a human. In some embodiments, the disclosure provides any of the foregoing methods comprising administering any of the antibodies or antigen-binding fragments of the disclosure.

In some embodiments, any of the internalizing moieties may be used to treat a tumor and/or cancer that is resistant to other chemotherapeutic drugs. In some embodiments, the tumor or cancer is platin resistant. "Platins" are platinum-containing anti-cancer drugs that include cisplatin, carboplatin and oxaliplatin, which all work by binding to and causing crosslinking of DNA in a cancer cell, ultimately triggering apoptosis. However, drugs like cisplatin are associated with numerous side effects, including nephrotoxicity, neurotoxicity, nausea and vomiting, ototoxicity, electrolyte disturbance, myelotoxicity and hemolytic anemia. In addition, the majority of cancer patients administered platins will eventually relapse with cisplatin-resistant disease. However, the internalizing moieties described herein were surprisingly found to be effective in inducing cell killing in representative platin-resistant cells. See Example 4. In some embodiments, the disclosure provides any of the foregoing methods comprising administering any of the antibodies or antigen-binding fragments of the disclosure.

In some embodiments, the platin-resistant tumor or cancer is resistant to any one or more of cisplatin, carboplatin, satraplatin, heptaplatin, picoplatin, nedaplatin, triplatin, lipoplatin and/or oxaliplatin. In some embodiments, the platin-resistant tumor or cancer is an ovarian, peritoneal, lung, testicular, colon, skin (e.g. melanoma), prostate, pancreatic, bone, blood, liver, muscular, neuronal, glioma, or breast cancer. In some embodiments, the platin-resistant tumor or cancer is an ovarian cancer. In some embodiments, the disclosure provides any of the foregoing methods comprising administering any of the antibodies or antigen-binding fragments of the disclosure.

In some embodiments, the internalizing moiety for use in any of the methods disclosed herein is a full-length antibody. In some embodiments, any one or more of the treatment effects disclosed herein (e.g., reduction of growth, proliferation or survival of a tumor cell; change in gene or marker expression) may be achieved using a full-length antibody at a lower concentration and/or less frequent dosing schedule needed to achieve the same effect using a corresponding fragment of the same antibody (e.g., an Fv, scFv, Fab, Fab'). In some embodiments, the full-length antibody is at least 10%, 20%, 30%, 40%, 50%, 60%, 70%, 80%, 90%, 100%, 150%, 200%, 300%, 400%, or 500% more effective at achieving any one or more treatment effects disclosed herein (e.g., reduction of growth, proliferation or survival of a tumor cell; change in gene or marker expression) as compared to a corresponding fragment of the same antibody (e.g., an Fv, scFv, Fab, Fab') when administered at the same concentration and dosage schedule. In some embodiments, the disclosure provides any of the foregoing methods comprising administering any of the antibodies or antigen-binding fragments of the disclosure.

In some embodiments, any of the internalizing moieties described herein may be administered in combination with any of the additional therapeutic treatments described herein. In some embodiments, the additional therapeutic treatment is radiotherapy, chemotherapy or tumor resection.

Administration "in combination with" one or more further therapeutic agents includes simultaneous (concurrent) and consecutive administration in any order. In some embodiments, any of the internalizing moieties described herein are administered to a subject in combination with an additional therapeutic treatment, wherein the subject has a tumor or cancer. In some embodiments, the additional therapeutic treatment is radiotherapy. In some embodiments, the additional therapeutic treatment is chemotherapy. In some embodiments, the additional therapeutic treatment is tumor resection. In some embodiments, the additional therapeutic treatment is a treatment that induces DNA damage in the tumor or cancer.

In some embodiments, the combined administration includes coadministration, using separate formulations or a single pharmaceutical formulation, and consecutive administration in either order, wherein preferably there is a time period while both (or all) active agents simultaneously exert their biological activities. In some embodiments, the additional therapeutic treatment and the antibody or antigen-binding fragment thereof are administered consecutively. In some embodiments, the additional therapeutic treatment is administered concurrently with the antibody or antigen-binding fragment thereof. In some embodiments, the additional therapeutic treatment is administered prior to the administration of the antibody or antigen-binding fragment thereof.

In some embodiments, combined therapy results in a cumulative therapeutic effect. In some embodiments, combined therapy results in a synergistic therapeutic effect. In some embodiments, the therapeutically effective amount of each of: a) the antibody or antigen binding fragment, and/or b) the additional therapeutic treatment is less than that required to achieve a therapeutic effect when one or both agents is administered as a monotherapy.

Exemplary additional therapeutic agents are known in the art. In some embodiments, the additional therapeutic agent is an RNA polymerase inhibitor, hydroxyureataxanes (such as paclitaxel and doxetaxel) and/or anthracycline antibiotics; alkylating agents; alkyl sulfonates; aziridines; ethylenimines and methylarnelamines; acetogeains; delta-9-tetrahydrocannabinol; beta-lapachone; lapachol; colchicines; betulinic acid; a camptothecin; bryostatin; callystatin; CC-1065; podophyllotoxin; podophyllinic acid; teniposide; cryptophycins; dolastatin; duocarmycin; eleutherobin; pancratistatin; a sarcodictyin; spongistatin; nitrogen mustards; nitrosureas; antibiotics; folic acid analogues; purine analogs; pyrimidine analogs; androgens; anti-adrenals; folic acid replenisher; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids; mitoxantrone; mopidanmol; nitraerine; pentostatin; phenamet; pirarubicin; losoxantrone; 2-ethylhydrazide; procarbazine; PSK(R) polysaccharide complex; razoxane; rhizoxin; sizofiran; spirogermanium; tenuazonic acid; triaziquone; 2,2',2"-trichlorotriethyiamine; trichothecenes; urethan; vindesine; dacarbazine; mannomustine; mitobronitol; mitolactol; pipobroman; gacytosine; arabinoside ("Ara-C"); thiotepa; taxoids; chloranbucil; gemcitabine (GEMZAR®); 6-thioguanine; mercaptopurine; methotrexate; platinum analogs; vinblastine; platinum; etoposide; ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluorometlhylornithine; retinoids; capecitabine; pharmaceutically acceptable salts, acids or derivatives of any of the above.

In other embodiments, therapeutic agents are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON®toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RFVISOR® vorozole, FEMARA® letrozole, and ARIMDDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTTN® vaccine, and VAXID® vaccine; LURTOTECAN® topoisomerase 1 inhibitor; ABARELDC® rmRH; lapatinib ditosylate (an ErbB-2 and EGFR dual tyrosine kinase small-molecule inhibitor also known as GW572016); and pharmaceutically acceptable salts, acids or derivatives of any of the above.

In some embodiments, the additional therapeutic agent is a growth inhibitor agent. A "growth inhibitory agent" when used herein refers to a compound or composition which inhibits growth of a cell. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase H inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995). The taxanes or hydroxyureataxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). These molecules promote the assembly of microtubules from tubulin dimers and stabilize microtubules by preventing depolymerization, which results in the inhibition of mitosis in cells.

In some embodiments, the additional therapeutic agent is a PARP inhibitor. Examples of PARP inhibitors include iniparib, talazoparib, olaparib, rucaparib, veliparib (ABT-888), CEP-9722, MK 4827, BGB 290, and 3-aminobenzamide.

In some embodiments, the additional therapeutic agent is a DNA-damaging compound. In some embodiments, the DNA-damaging compound is a DNA cross-linker (e.g., a platin such as cisplatin, carboplatin, oxaliplatin or an active analog thereof), an inhibitor of DNA synthesis (e.g., methotrexate or an active analog thereof), a topoisomerase poison (e.g., doxorubicin, daunorubicin, or an active analog thereof), a DNA alkylating agent (e.g., a nitrosurea, triazene compound or an active analog thereof), and/or an antimetabolite (e.g., a pyrimidine analog such as 5-fluorouracil or an active analog thereof).

In some embodiments, the additional therapeutic agent is an enzymatically active toxin or fragment thereof that includes diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyapates (such as tolyene 2,6-diisocyanate), and bis-active fluorine compounds (such as 1,5-difluoro-2,4-dinitrobenzene). For example, a ricin immunotoxin can be prepared as described in Vitetta et aL, Science, 238: 1098 (1987). Carbon-14-labeled 1-isothiocyanatobenzyI-3-methyldiethylene triaminepentaacetic acid (MX-DTPA) is an exemplary chelating agent for conjugation of radionucleotide to the antibody. See WO94/11026. Conjugates of an antibody and one or more small molecule toxins, such as a calicheamicin, maytansinoids, a trichothene, and CC 1065, and the derivatives of these toxins that have toxin activity, are also contemplated herein.

In some embodiments, the additional therapeutic therapeutic treatment is an additional therapeutic agen that is conjugated to the internalizing moiety as a heterologous agent, such as chemically conjugated. In other embodiments, the additional therapeutic is separately administered (e.g., not conjugated to the antibody or antigen binding fragment of the disclosure). Combination therapeutics may be administered at the same or different times, via the same or different route of administration, according to the same or differing dosing schedule. In certain embodiments, the combination therapeutic is co-formulated so it can be administerd together in a single infusion.

The Physicians' Desk Reference (PDR) discloses dosages of these additional agents that have been used in treatment-of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

VIII. Other Uses

The compositions of the disclosure have numerous uses. For example, the humanized antibodies and antigen binding fragments, either alone or conjugated to a heterologous agent, are useful for studying preferential cell and tissue distribution in cells and in tissues in vitro and/or in vivo. Similarly, the humanized antibodies and antigen binding fragments, either alone or conjugated to a heterologous agent are useful as imaging agents, such as for ex vivo or in vivo diagnostic applications. For example, the humanized antibodies or antigen binding fragments conjugated to a radioactive moiety are useful for ex vivo or in vivo imaging studies. Such studies are particularly useful for imaging cancer and defects or injuries of skeletal and cardiac muscle—due to localization of the antibody portion to such tissues. See, WO 2012/145125. Similarly, any of the antibodies or antigen binding fragments of the disclosure are similarly useful.

Moreover, the antibodies and antigen binding fragments of the disclosure, such as humanized antibodies and antigen binding fragments are useful for delivering heterologous agents into cells and tissues, either in vitro or in vivo. By way of example, the disclosure provides methods of delivering a conjugate or other conjugate comprising a heterologous agent into cells. When used in vitro, conjugates of the disclosure are suitable for identifying binding partners for the internalizing moieties or heterologous agent being delivered (e.g., identifying proteins or peptides that bind the internalizing moiety or heterologous agent), and for evaluating localization and trafficking. Similarly, when used in vivo, conjugates of the disclosure are suitable for identifying binding partners for the internalizing moieties or for the heterologous agent being delivered (e.g., identifying proteins or peptides that bind the internalizing moiety or heterologous agent), for evaluating localization and trafficking, for evaluating biodistribution and half-life, and for evaluating immunogenicity.

Moreover, antibodies and antigen binding fragments of the disclosure, such as humanized antibodies or antigen binding fragment of the disclosure are useful as diagnostic agents in vitro or in vivo, such as in human subjects. For example, an antibody or antigen binding fragment of the disclosure can be labeled, such as with a detectable label suitable for imaging. The labeled antibody or antigen binding fragment can be administered to cells, ex vivo, or to subjects and use to evaluate localization of the antibody in cells and tissues and/or to evaluate clearance. Given that 3E10 antibodies have been shown to localize to cancers, in certain embodiments, labeled antibodies are useful as diagnostic reagents for imaging and/or diagnosing ENT2 expressing cancers.

In certain embodiments, the humanized antibodies and antigen binding fragments have decreased immunogenicity, in comparison to a murine antibody, and thus are preferred for use in human subjects. Finally, the humanized antibodies and antigen binding fragments, either alone or conjugated to a heterologous agent, are useful for elucidating the comparative properties of this humanized antibody in comparison to the murine parent antibody, as well as other humanized antibodies. Such comparisons are useful for optimizing delivery agents, both from an efficacy perspective, as well as for characteristics that improve manufactureability. Similarly, any of the antibodies or antigen binding fragments of the disclosure are similarly useful.

IX. Model Systems

Numerous animal models of cancer are known in the art. For example, various human tumor xenograft mouse models are widely used for studying different types of cancer. In these models, human tumor cells are transplanted, either under the skin or into the organ type in which the tumor originated, into immunocompromised mice (e.g., athymic mice, SCID, NON-SCID, or Rag2-knockout mice) that will not reject the human cells. Types of human tumor cells that have been used to successfully create tumor xenograft mouse models include, for example, bladder (SW780), brain (SF-295, SK-N-AS, U87 MG, U251), breast (BT474, HCC-1806, HCC-1954, JIMT-1, MCF-7, MDA-MB-231), colon (CL-34, COLO 205, DLD-1, HCT 116, HCT-15, HT-29, LoVo, LS-174T, LS411N, RKO, SW48, SW480, SW620, HT-29), epithelial (A-431), gastric (N87, SNU-5), head and neck (FaDu), leukemia (HL-60, K-562, MOLM-13, MOLT-4, MV4-11, SET2), liver (Hep3B, HuH-7, SNU-398), lung: non-small cell (A-427, A549, Calu-6, H1299, H1975, H226, H292, H460, H520, H522, H647, H727, H810, HCC-44, NCI-H2122, SK-MES-1), lung: small cell (H69, H82, H211, H526, SHP-77, DMS 114), lymphoma (Daudi, DoHH-2, Granta 519, JEKO-1, Namalwa, Raji B, Ramos, REC-1, RL, SU-DHL-4, WSU-DLCL2), melanoma (MSTO-211H), mesothelioma (MSTO-211H), multiple myeloma (H929, OPM-2, RPMI 8226), neuroblastoma (H929, OPM-2, RPMI 8226), ovarian (A2780, IGR0V1, OVCAR-3, OVCAR-5, SKOV-3, TOV-21G), pancreas (BxPc-3, HPAC, KP4, MIA PaCa-2, PANC-1, CAPAN-1), prostate (22Rv.1, PC3), renal (786-0, G-401, G-402), sarcoma (HT-1080, SJSA-1), thyroid (8505C, FTC-238), and/or uterine (ECC-1, MFE-280). The skilled worker is aware of additional cancer/tumor cell lines that would be appropriate for generating additional xenograft models. The skilled worker would also understand how to make new xenograft models using newly identified tumor/cancer cells.

In some embodiments, the internalizing moieties may be administered to an animal model having a genetic alteration that predisposes that animal to developing a tumor or cancer. The skilled worker is aware of numerous such genetically engineered models in the art. Examples of genetically engineered mouse models of different cancer types include: NSCLC lung cancer (K-ras$^{G12D-LA2}$ or K-ras$^{LSLG12D}$ or K-ras$^{LSG12V}$), SCLC lung cancer (RB$^{F1}$+p53$^{F1}$), breast (p53$^{LSLR270H}$ or Wnt-1±p53KO or p53-KO or c-MET±c-Myc), prostate (NKX3.1-KO+PTEN-KO+p27-KO or PTEN$^{F1}$ or PTEN$^{F1+p}$53$^{F1}$), colon (APC$^{min}$ or APC$^{66716}$+ SMAD4-KO, or APC$^{F1-580S}$), ovarian (p53-KO±K-ras$^{G12D}$ or c-MYC or AKT$^{Mye}$ or RB$^{F1}$+p53$^{F1}$ or K-ras$^{LSLG12D}$ +/−PTEN$^{F1}$), or pancreas (K-ras$^{LSLG12D}$ or p16/INK4A$^{F1}$ or p19/ARF$^{F1}$ or K-ras$^{LSLG12D}$ or p53$^{LSLR172H}$) cancer mouse models. See, e.g., Singh et al., 2006, Clin Cancer Res, 12(18):5312-5328. The skilled worker is aware of additional genetically engineered model animals that would be appropriate for testing any of the internalizing moieties described herein. In addition, the skilled worker would also understand how to test the internalizing moieties in genetically engineered model animals yet to be generated.

Accordingly, in certain embodiments, the present disclosure contemplates methods of surveying improvements in cancer or tumor phenotypes using any of the internalizing moieties described (alone or in combination with any of the heterologous agents and/or additional therapeutic treatments described herein) in any one or more animal models, such as the mouse models described herein. By way of example, various parameters can be examined in experimental animals treated with a subject internalizing moiety, and such animals can be compared to controls. Exemplary parameters that can be assessed to evaluate potential efficacy in cancer mouse models include, but are not limited to: reduction in the number of tumor cells or absence of such cells; reduction in the tumor size; inhibition (i.e., slow to some extent and preferably stop) of tumor cell infiltration into peripheral organs including the spread of cancer into soft tissue and bone; inhibition (i.e., slow to some extent and preferably stop) of tumor metastasis; inhibition, to some extent, of tumor growth; and/or relief to some extent, of one or more of the symptoms associated with the specific cancer; reduced morbidity and mortality, reduction in tumor cell proliferation (which may be measured, for example, by assessing Ki67 staining), promotion of collapse of capillary blood vessels in a tumor (which may be measured, for example, by assessing CD31 staining patterns), increase of necrosis and/or apoptosis of tumor cells (which may be measured, for example, by assessing hematoxylin and eosin staining patterns), and improvement in quality of life issues in a tumor and/or cancer animal (e.g., mouse) model.

Moreover, once it is established that, for example, any of the internalizing moieties described herein (alone or in combination with any of the heterologous agents and/or additional therapeutic treatments described herein) results in an improvement in any one or more of these phenotypes, a complete pharmacokinetic study to determine the effective dose, clearance rate, volume of distribution, and half-life of any of the internalizing moieties described herein (alone or in combination with any of the heterologous agents or additional therapeutic treatments described herein) can be determined. The pharmacokinetics of any of the internalizing moieties described herein (alone or in combination with any of the heterologous agents or additional therapeutic treatments described herein) will likely follow a multi-compartment model in which various tissues exhibit different degrees of clearance, and simple assessments of serum half-life will not provide sufficient information to calculate a therapeutic dosing rate. Therefore, the calculation of a dose and dosing rate will ultimately be derived from empirical observations of the pharmacokinetics, pharmacodynamics, toxicology of a given dose of the internalizing moiety, and the rate and extent to which an improvement in symptoms is observed. The dose and dosing rate of any of the internalizing moieties described herein (alone or in combination with any of the heterologous agents or additional therapeutic treatments described herein) determined in a subsequent pharmacokinetic study can be used as the standard comparator to evaluate optimized lots of, for example, any of the internalizing moieties described (alone or in combination with any of the heterologous agents and/or additional therapeutic treatments described herein). The PK/PD/TK of the final product can then be examined in larger animals such as rats, dogs, and primates.

The above models provide a suitable animal model system for assessing the activity and effectiveness of the subject internalizing moieties. These models have correlations with symptoms of different cancer and tumor types, and thus provide appropriate models for studying the effects of the internalizing moieties on cancer and tumors in animals. The skilled worker is aware of other available animal models in which effects of the internalizing moieties on cancer and tumors can be examined. Activity of the internalizing moiety can be assessed in these mouse models, and the results compared to that observed in wildtype control animals and animals not treated with the internalizing moieties.

Similarly, the subject internalizing moieties (alone or in combination with any of the heterologous agents or additional therapeutic treatments described herein) can be evaluated using cells in culture, for example, any of the numerous cancer cell lines available to the skilled worker or using cancer/tumor cells taken from a subject (e.g., a human). In some embodiments, the internalizing moieties may be tested in any of the patient-derived xenograft (PDX) cancer models described in the art (e.g., any of the PDX models available from Jackson Laboratory).

Examples of useful tumor or cancer cell lines include, but are not limited to, breast (MCF7, HSF78T, T47D, MDAMB231, BT-549, NIC/ADR-RES), prostate (PC-3, DU-145), renal (786-0, A498, ACHN, CAKI-1, RXF-393, SN12C, TK-10, UO-31), ovarian (IGR-OV1, OVCAR-3, OVCAR-4, OVCAR-5, OVCAR-8, SKOV-3), melanoma (UACC-62, UACC-257, SK-MEL-1, M14), colorectal (CaCO2, WiDr, SW48, HCT8, HCT15, SW837, SW403, SW480, HCT-116, HT-29), pancreatic (AsPC-1, CD18, EPP85-181P, EPP85-181RDB, PANC-1, CAPAN-1), stomach (AGC, BON, EPG85-257P, KATO III, TMK-1), uterine (HeLa, RL95-2, SiHa), liver (BEL-7402, HA22T, Hep3B, HepG2, HLF), bone (6647, HOS-1, MG-63, PDE02, SaOs-2, SW872), and bladder (BFTC905, EJ, J82, RT112, T42, TSGH8301). The skilled worker is aware of numerous other cancer cell lines that would be appropriate for testing the effects of any of the internalizing moieties described herein (alone or in combination with any of the heterologous agents or additional therapeutic treatments described herein). In some embodiments, any of the internalizing moieties described herein is administered to a cell line having DNA repair mutations. In some embodiments, the cell line having DNA repair mutations is, for example, ES-2, PEO1, HT-29, DLD1, U251 or CAPAN1. In some embodiments, any of the internalizing moieties described herein is administered to a cell line that is resistant to platins (e.g., SKOV-3). In some embodiments, the cell lines to be tested include cell lines having active mismatch repair, e.g., CCD-18Co (ATCC CRL-1459); HT-29 (ATCC HTB-38); or OVCAR-3 (ATCC HTB-161). In some embodiments, the cell lines to be tested include cell lines having inactive or deficient mismatch repair, e.g., HCT 116 (ATCC CCL-247); SK-OV-3 (ATCC HTB-77); and HC-59 (AddexBio C0026001).

Additional cell lines and animal models for testing any of the internalizing moieties described herein (alone or in combination with any of the heterologous agents described herein) in other cancer or tumor models are known in the art.

In certain embodiments, the disclosure provides methods of treating a subject in need thereof by administering an antibody or antigen binding fragment of the disclosure, wherein the subject in need there has a tumor comprising cells having one or more of the foregoing mutations or alterations. In certain embodiments, the disclosure provides methods of treating a subject in need thereof by administering an antibody or antigen binding fragment of the disclosure, wherein the subject in need there has a tumor characterized by the presence of cells having one or more of the foregoing mutations or alterations.

EXEMPLIFICATION

The disclosure now being generally described, it will be more readily understood by reference to the following examples, which are included merely for purposes of illustration of certain aspects and embodiments of the present disclosure, and are not intended to limit the disclosure.

Example 1: Generation of Antibodies of the Disclosure

Figure 10:
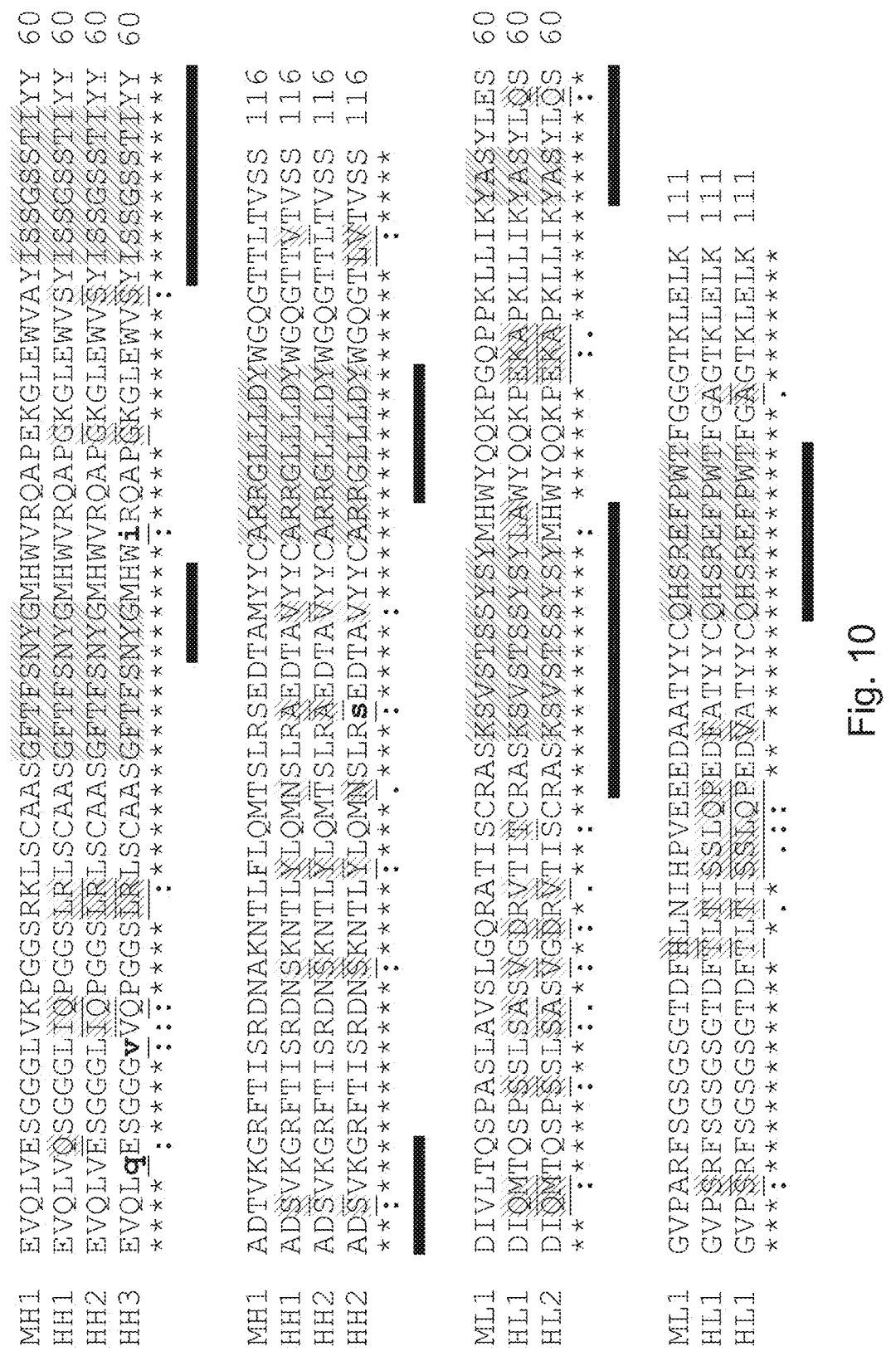

The heavy chain variable domain of murine 3E10 (MH1-SEQ ID NO: 9) and each of the HH1 (SEQ ID NO: 38), HH2 (SEQ ID NO: 39) and HH3 (SEQ ID NO: 10) heavy chain variable domains (where HH depicts humanized heavy chain variable domains) were expressed in various pairwise combinations with a light chain variable domain selected from: (i) the murine 3E10 (ML1-SEQ ID NO: 7), (ii) the HL1 (SEQ ID NO: 40), and (iii) the HL2 (SEQ ID NO: 8) (where HL depicts humanized light chain variable domains). A sequence alignment for each of the humanized sequences as compared to the murine SEQ ID NO: 7 or SEQ ID NO: 9 parent sequences is illustrated in FIG. 10. For simplicity, each pairwise combination will be referred to in these examples in terms of the heavy and light chain variable domains present in the respective antibodies (e.g., HH1/HL1 is an antibody comprising the HH1 heavy chain variable domain and the HL1 light chain variable domain). Note that, for these experiments, full length antibodies were made and tested with each pairwise combination of VHs and VLs expressed recombinantly on a human IgG1 Fc. Antibody fragments, such as Fabs or scFvs comprising combinations of heavy and light chain variable domains are similarly contemplated and can be made and evaluated as described herein. Moreover, antibodies can readily be made on other immunoglobulin backbones, including non-human backbones, but preferably, on other human immunoglobulin heavy and light chain constant backbones, such as an IgG2a, IgG3, or IgG4 backbone.

DNA encoding for each pairwise heavy/light combination (total of 12-see Table 1) was inserted into a single vector using the GS Xceed Gene Expression System (Lonza), and the resulting vector was stably transfected and expressed in CHOK1SV GS-KO cells.

TABLE 1

| Antibody Construct Designation | Description |
| --- | --- |
| MH1/ML1 | Comprises: a heavy chain comprising the murine, parent VH; and a light chain comprising the murine, parent VL |
| MH1/HL1 | Comprises: a heavy chain comprising the murine, parent VH; and a light chain comprising the HL1 light chain variable domain |
| MH1/HL2 | Comprises: a heavy chain comprising the murine, parent VH; and a light chain comprising the HL2 light chain variable domain |
| HH1/ML1 | Comprises: a heavy chain comprising the HH1 heavy chain variable domain; and a light chain comprising the murine, parent VL |
| HH1/HL1 | Comprises: a heavy chain comprising the HH1 heavy chain variable domain; and a light chain comprising the HL1 light chain variable domain |
| HH1/HL2 | Comprises: a heavy chain comprising the HH1 heavy chain variable domain; and a light chain comprising the HL2 light chain variable domain |
| HH2/ML1 | Comprises: a heavy chain comprising the HH2 heavy chain variable domain; and a light chain comprising the murine, parent VL |

TABLE 1-continued

| Antibody Construct Designation | Description |
|---|---|
| HH2/HL1 | Comprises: a heavy chain comprising the HH2 heavy chain variable domain; and a light chain comprising the HL1 light chain variable domain |
| HH2/HL2 | Comprises: a heavy chain comprising the HH2 heavy chain variable domain; and a light chain comprising the HL2 light chain variable domain |
| HH3/ML1 | Comprises: a heavy chain comprising the HH3 heavy chain variable domain; and a light chain comprising the murine, parent VL |
| HH3/HL1 | Comprises: a heavy chain comprising the HH3 heavy chain variable domain; and a light chain comprising the HL1 light chain variable domain |
| HH3/HL2 | Comprises: a heavy chain comprising the HH3 heavy chain variable domain; and a light chain comprising the HL2 light chain variable domain |

One transfection for each of the twelve constructs was set up in a 125 mL Erlenmeyer flask. The cultures were passaged to 100 mL culture when their viable cell density was higher than $0.6 \times 10^6$ cells/mL. Cells were further passaged to produce $2 \times 400$ mL cultures (800 mL total) in 1 L vented Erlenmeyer flasks for each variant. Good viability and antibody expression was observed in the stably-transfected cultures for all of the above antibodies made after 4-6 days in culture. The cells were harvested following six days in culture, and the clarified supernatants were pooled and purified on 5 mL HiTrap MabSelect SuRe Protein A columns. The eluted products were neutralized with 1 M Tris (1:40 volume ratio) and filtered through 0.22 μm filters. The final pH values for all products ranged from 7.2 to 7.6. Certain pairwise combinations have been produced and purified using alternative expression scheme.

An antibody lacking Fc effector function ("effector dead") was also generated. Briefly, 2×10L bioreactors were set up to produce a humanized antibody that lacked complement function due to an N to Q substitution at a position corresponding to Kabat position 297 in the CH2 region of the Fc domain. CHO cells were grown in PF-CHO media and the bioreactors were harvested on day 19 when the viability was between 83.5% and 85.0%. Antibody was purified using depth filtration followed by 0.2 μm filtration, and then MabSelect (GE Healthcare). Antibody was eluted using 20 mM citric acid and sodium citrate. Antibody was stored in 1M HEPES at pH 7.0 (~80 mM final).

Example 2: Nucleotide Binding of a Humanized Antibody i. Binding in a SNAP 10-mer Array The ability of a humanized 3E10 antibody (an antibody comprising humanized heavy chain (comprising the amino acid sequence of one of SEQ ID NO: 38, SEQ ID NO: 39 or SEQ ID NO: 10; associated with an IgG1 constant domain) and a humanized light chain (comprising one of SEQ ID NO: 8 or SEQ ID NO: 40)) to bind DNA was assessed using a SNAP (Specificity and Affinity for Protein) 10-mer array. The stock antibody used in this assay was at 6.4 mg/ml in 25 mM Tris pH 7.5.

The antibody was tested at up to 3 different conditions (concentration, buffer, length of incubation may be varied as needed) on an initial 10-mer array (25 bp hairpin with 3 base loop) to assess binding to all 10-mer DNA permutations and to examine reactivity of the antibody with the array background, hairpin loop, and probe constant regions. Detection of binding was with an Alexa Fluor labeled secondary Ab against the test Ab. The data was analyzed and provided as DNA binding motifs and/or sequence specificity landscapes.

Initial binding experiments showed a strong spatial effect on the array, likely caused by aggregation of the antibody. Increasing amounts of glycerol, detergent, and carrier proteins showed some improvement of the spatial effect, however it was not completely obviated. Despite these spatial effects, extraction and analysis of the array showed specific binding of the antibody to probes with a signal ~5-fold higher than non-specific binding (15000 vs. 3000). No non-specific binding to the ubiquitous probe hairpin was observed, and non-specific antibody binding to the array surface was minimal with signal intensity ~200.

Further analysis indicates preferential binding to DNA structures, comprised of a 5-mer variable region adjacent to a 7-base or 11-base bubble. Minimal binding to other control sets containing the 5-mer variable region suggest that this binding is structure-specific as opposed to sequence specific. In addition to structural controls, the antibody showed a preference for several control DNA probes bearing the FoxA1 motif of 5'-GTAAACAA-3' (SEQ ID NO: 14).

Motif analysis of all 8-mers present within the 10-mer probeset revealed a preference for mixed base AT-rich sequence of 4 bp in length, similar to the TATA-box binding protein (TBP). This may be indicative of a non-specific preference for groove width or DNA flexibility as is characteristic of AT rich DNA. Alternatively, several proteins recognize AT rich motifs, such as the TATA binding protein (TBP), and these results could be suggestive of specific sequence recognition.

ii. Binding in a SNAP 12-mer Array

In a similar experiment, the antibody tested in the 10-mer array described above was also tested in a SNAP 12-mer array. Specifically, 3 nM of the antibody in binding buffer (Tris, KCl, $MgCl_2$, EDTA, DTT, glycerol, plus detergent and carrier) was tested in a 385,000 DNA SNAP array bearing 12-mer DNA and multiple DNA sequences, controls and structures. Detection was carried out using an AlexFluor labeled anti-human antibody. These experiments were performed twice, with a signal to background of 3-5 fold.

Based on the results of the 12-mer array experiment, a sequence specificity landscape (SSL) was prepared. The SSL displays the comprehensive binding specificity and relative affinity of the DNA binding ligand for all sequences assayed. Intensities for each DNA sequence from the array are plotted on a series of concentric rings where each array sequence in the center ring contains a subsequence that perfectly matches the motif, sequences in the second ring have one mismatch, sequences in the third ring contain two mismatches, and so forth. The peak height corresponds to intensity or affinity, as verified by solution-based studies.

From performing these experiments, it was found that AT-rich sequences gave the highest intensity central ring in the SSL. When GC was used as the "seed motif," the highest intensity probes are found in the outer rings—indicating that GC-rich motifs are not preferred.

From these 12-mer array experiments, it was also found that the antibody preferably bound to the following motifs: a) 4-mer TATA motifs within a 6 base pair sequence, in permuted 12-mer; b) a T-rich bubble; and c) a Fox-motif (consensus is TRTTKRY (SEQ ID NO: 52), where R=A/G, Y=C/T, and K=T/G).

iii. Additional DNA Binding Experiments

The DNA binding of the antibody tested in the previous 10-mer experiments was tested in a modified 10-mer experiment. Initial assays were conducted on a validated array design that included more than 400,000 individual probe sequences, with constant (flank and loop) and variable regions within each probe. The probes comprised every possible 10-mer as a dsDNA with 3 bp loops for hairpin plus 69 additional probe groups of various controls, including: a) non B-form DNA structures, bubbles, bulges, g-quadruplexes, i-motif, stem-loops, ssDNA, and transcription factor consensus controls (ER, GR, AR, ERR, FoxA1, GATA3). In additional experiments, the effect of $MgCl_2$ on DNA binding was also tested.

From these experiments, it was determined that the antibody tested in the array with $MgCl_2$ showed higher total raw signal and less spatial artifacts due to aggregation in the assay. These experiments demonstrated that the antibody again preferably bound to a) AT rich sequence; b) a T-rich bubble (typically smaller bubbles); and c) a Fox-motif. Representative sequences bound strongly by the antibody included SEQ ID NOs: 19-23 (12-mers), SEQ ID NOs: 24-26 (FoxA1 probes) and SEQ ID NO: 27 (T-rich bubble). Sequences bound with weaker affinity by the antibody included SEQ ID NOs: 11 and 44 (12-mers) and SEQ ID NO: 46 (FoxA1 probe).

In further SNAP experiments, the ability of the antibody to bind various T-rich bubble structures demonstrated that, while the antibody was capable of binding T-rich bubble structures having smaller bubbles, the antibody showed nearly two-fold stronger binding to T-rich bubble structures having larger bubbles.

Example 3: Assessment of Genotoxicity and Cytotoxicity in Healthy Cells/Animals

Two different cytotoxicity assays were performed to evaluate cytotoxicity of the humanized antibodies generated.

In the first assay, the genotoxicity (i.e., the ability of an agent to cause damage to nucleic acids) and cytotoxicity of one of the humanized antibodies was assessed in a GreenScreen HC assay. In performing this test, a dilution series of the humanized antibody was generated in a 96-well, black microplate with an optically clear base. A standard genotoxic compound (methyl methanesulfonate, MMS) was also used as an intra-plate quality control check. Two strains of cultured human GreenScreen HC cells (lymphoblastoid TK6 cells) were used: the test strain (GenM-T01) and the non-fluorescent control strain (GenM-001), the latter used to allow correction for any autofluorescence from the test compounds. Incorporated in the test strain was a green fluorescent protein (GFP) reporter system that exploits the proper regulation of the GADD45a gene, which mediates the adaptive response to genotoxic stress. Exposure to a genotoxic compound increases expression of GFP and hence the induction of cellular fluorescence in the test strain. Each dilution of the antibody was combined with an equal volume of a specialized growth medium containing GreenScreen HC cells. The micro-plates were covered with a breathable membrane and incubated at 37° C. with 5% $CO_2$ and 95% humidity for 48 hours. The plates were analyzed at 24 hour and 48 hour time points using a microplate reader that provides measurements of light absorbance and fluorescence for cells and solutions in the micro-plate wells. Absorbance is proportional to cell proliferation, which was lowered by toxic analytes, and fluorescence is proportional to the activity of the cell's DNA repair system, which is increased by genotoxic analytes. Fluorescence was normalized to the absorbance signal to correct for variation in cell yield caused by cytotoxicity. The GreenScreen HC assay has automatic compensation for a test compound's auto-fluorescence by the use of the non-fluorescent control strain, fluorescence data (per cell) from which are subtracted from those of the test strain. In cases of more intense test article auto-fluorescence (automatically flagged in the data analysis template) a fluorescence polarization (FP) data collection protocol is then employed. Essentially, this exploits the high fluorescence anisotropy of GFP to discriminate GFP fluorescence from test compound auto-fluorescence. FP data were collected by illuminating each microplate well with parallel polarised light and measuring fluorescence intensity both parallel (Ipara) and perpendicular (Iperp) to the excitation light. The fluorescence intensity used for data analysis is the difference between these measurements (Ipara—Iperp), which is large for GFP and disproportionately small for auto-fluorescent test molecules that are commonly much smaller in size and with a low fluorescence anisotropy. There was no observed genotoxicity or cytotoxicity associated with the humanized antibody at a concentration of 5 µM in healthy human cells as determined by the Cyprotex GreenScreen assay.

The effects of an antibody of the disclosure (an antibody comprising humanized heavy chain (comprising the amino acid sequence of one of SEQ ID NO: 38, SEQ ID NO: 39 or SEQ ID NO: 10; associated with an IgG1 constant domain) and a humanized light chain (comprising one of SEQ ID NO: 8 or SEQ ID NO: 40)) were also tested in healthy cynomolgus monkeys. The humanized antibody used in this study lacked complement function due to an N to Q substitution at a position corresponding to Kabat position 297 in the CH2 region of the heavy chain. In this study, 3-year old cynomolgus monkeys were administered the antibody in the right leg (saphenous vein) for the first dose (5 mg/kg) and were administered all remaining doses as a slow bolus via intravenous catheter. Monkeys were administered either: a) consecutive weekly doses of 5, 10, 25 and 50 mg/kg of antibody or b) 50 mg/kg for all weekly doses. Blood and urine chemistry was assessed in the monkeys during the course of the study the day after treatment administration. No significant negative effects of antibody treatment were observed in the treated monkeys at any of the administered doses.

Example 4: Effects of a Humanized 3E10 Antibody on Cultured Cancer Cells

In order to test the effects of an antibody of the disclosure on cancer cells, a humanized 3E10 antibody (an antibody comprising humanized heavy chain (comprising the amino acid sequence of one of SEQ ID NO: 38, SEQ ID NO: 39 or SEQ ID NO: 10) and a humanized light chain (comprising one of SEQ ID NO: 8 or SEQ ID NO: 40)) was administered to various cultured cancer cell lines, and the effects of the antibody on the cancer cells was monitored in a manner similar to that described in Noble et al., 2015, Cancer Res., 75(11):1-7. Specifically, a pancreatic cancer cell line (CA-PAN1) and four colorectal cancer cell lines (HT29, SW837, SW480 and DLD-1) were plated in 48-well plates at $1 \times 10^4$ cells and allowed to adhere overnight. DLD-1 cells were either wildtype for BRCA2 protein expression or were deficient for BRCA2 activity. Cells were treated with saline buffer or 5, 10 or 15 µM of the antibody or with the antibody in combination with the RNA polymerase inhibitor alpha-amanitin (Sigma) or the PARP inhibitor ABT-888 (veliparib from Selleck Chemicals). Cells were treated every two days over a 4 day study for a total of two treatments. Surprisingly, while administration of 5 µM of the antibody did not have cytotoxic/genotoxic effects on healthy human cells (see Example 3), administration of the antibody at the same concentration to each of the four cancer cell lines resulted in toxicity (FIGS. 1A-1H). This toxicity was increased upon increasing the dose concentration of antibody administered to the cells (FIGS. 1A-1H). In addition, the cytotoxic effects of the alpha-amanitin and veliparib (ABT-888) on the cancer cells were increased when combined with treatment with the antibody (FIGS. 1A-1H). Surprisingly, the antibody-induced toxicity was observed in both BRCA2 proficient and BRCA2 deficient DLD-1 cell lines (FIGS. 1E-1H). In addition, while the PARP inhibitor ABT-888 had minimal effect on cell viability of BRCA2 proficient DLD-1 cell lines, the humanized 3E10 Mab antibody had a strong observeable effect on the viability of these cells.

In a separate experiment, the effect of a representative humanized internalizing moiety of the disclosure on induction of apoptosis is assessed. Specifically, levels of apoptotic markers are examined in treated and untreated cultures of at least or one or more of the following cell lines: HT29, CCD-18Co, HCT-116, OVCAR-3, SKOV-3 and HC-59. Each cell line is cultured in twelve separate T75 flasks (six control flasks and six treated flasks). Each cell line is cultured in RPMI-1640+10% FBS +2 mmol $L^{-1}$ L-glutamine, except for OVCAR-3 cells, which are cultured in RPMI-1640 ±20% FBS+2 mmol $L^{-1}$ L-glutamine, plus insulin. One of the duplicate cultures for each cell line is treated with buffer (70 mM HEPES-buffered citrate, pH 7.0), while the other culture are treated with 10 μM of the internalizing moiety in 70 mM HEPES-buffered citrate, pH 7.0. After 24 hours, three flasks from each treated cell line, and three flasks from each untreated control cell line are washed in cold PBS containing RNAse inhibitors, and the cells are harvested using cell scrapers, and collected by centrifugation at 400 g for 10 minutes. After 48 hrs, the remaining three flasks in each treatment condition (treated and untreated controls) are washed in cold PBS containing protease inhibitors, the cells harvested using cell scrapers, and collected by centrifugation at 400 g for 10 mins. Cell pellets are snap frozen and stored at −80° C. prior to further analysis. The cell pellets from the 24 hour flasks are assessed for RNA levels of apoptotic markers, and the cell pellets from the 48 hour flasks are assessed for protein levels of apoptotic markers. Protein levels are tested using a Human Apoptosis Antibody Array (abcam, ab134001), which tests for the presence of 43 different human apoptotic markers, including Bax, Bcl-2 and caspase-3. An increase in one or more pro-apoptotic markers and/or a decrease in one or more anti-apoptotic markers in internalizing moiety-treated samples as compared to untreated control samples is evaluated.

In alternative experiments, the cancer cell lines described above are grown in wells of a 48 well plate, treated with or without a representative internalizing moiety of the disclosure for four days beginning at 24 hours post-plating (with media replenishment at 48 hours post-initiation), and then assessed for RNA and protein levels of apoptotic markers on day five. An increase in one or more pro-apoptotic markers and/or a decrease in one or more anti-apoptotic markers in internalizing moiety-treated samples as compared to untreated control samples is evaluated.

In further alternative experiments, the cancer cell lines described above are grown in wells of a 48 well plate, treated with or without a representative internalizing moiety of the disclosure for four days beginning at 24 hours post-plating (with media replenishment at 48 hours post-initiation), and then treated with propidium iodide and Annexin V (Dead Cell Apoptosis Kit, ThermoFisher Scientific) on day five. Apoptotic cells appear as fluorescent green, necrotic cells appear as fluorescent red, and untreated cells do not show green or red fluorescence.

Figure 2A:
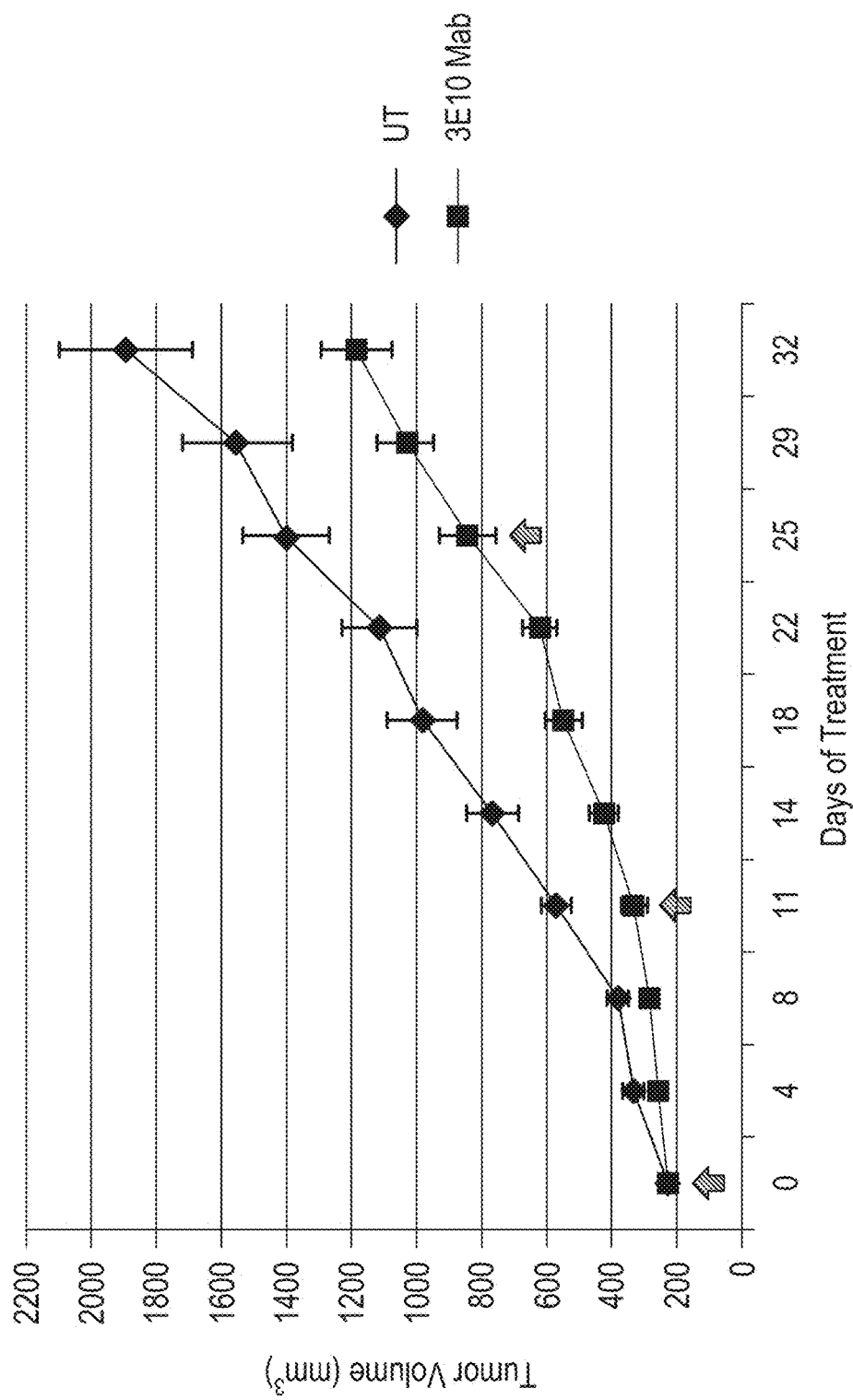
FIG. 2A is a line graph illustrating the effects of a humanized antibody (3E10 Mab) of the disclosure on tumor volume in an HT-29 xenograft mouse model as compared to an untreated (UT) control. Tumor volume was measured in ten treated and ten untreated mice at the indicated timepoints. Arrows indicate dates of antibody administration (1 mg/kg).
Figure 2B:
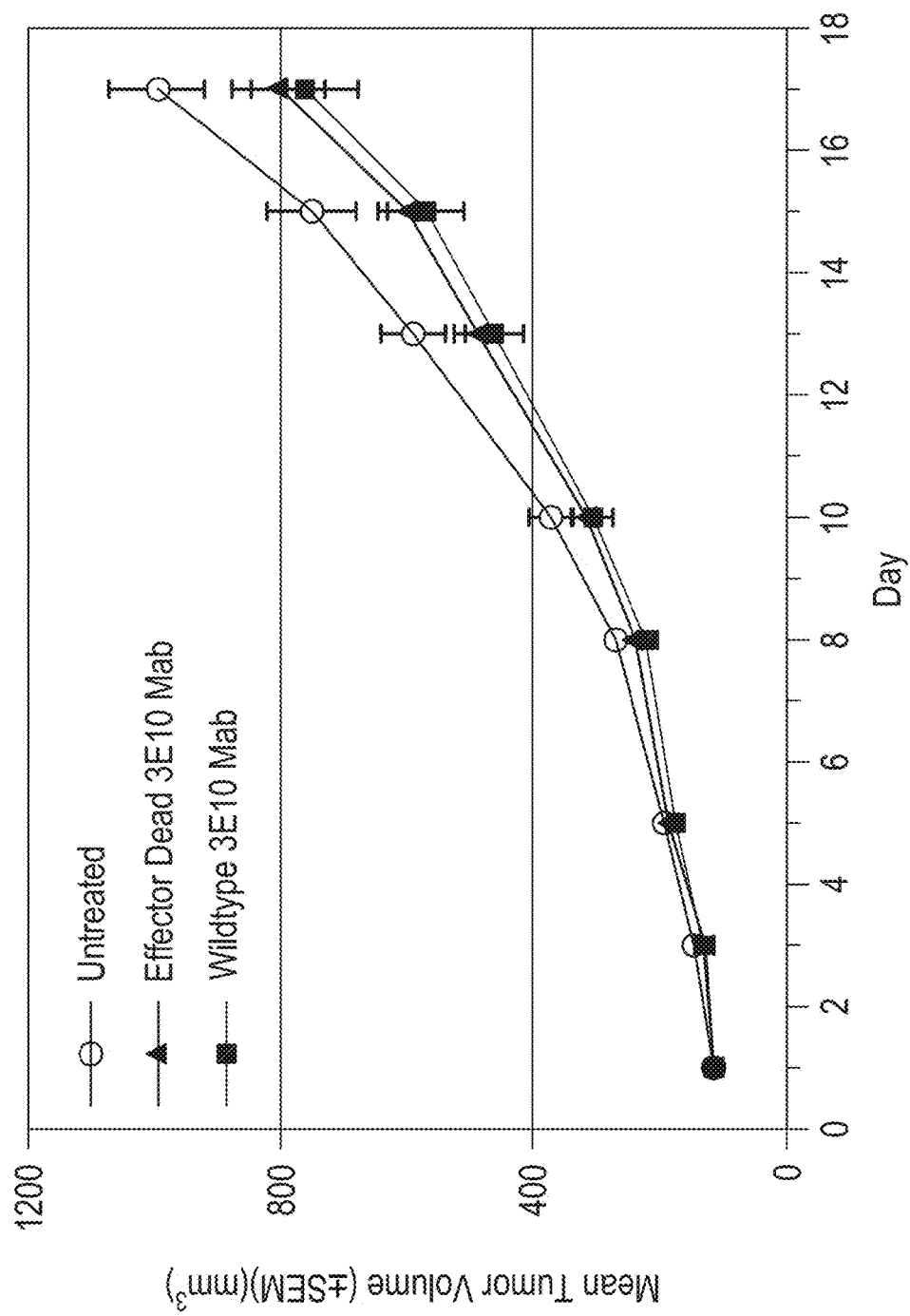
FIG. 2B is a line graph illustrating the effects of a single dose (1 mg/kg) of a humanized antibody of the disclosure retaining effector function (Wildtype 3E10 Mab) on tumor volume in an HT-29 xenograft mouse model as compared to a single dose (1 mg/kg) of the same antibody lacking effector function (Effector Dead 3E10 Mab) and untreated control. Tumor volume was measured in twenty mice from each treatment group at the indicated timepoints.
Figure 3A:
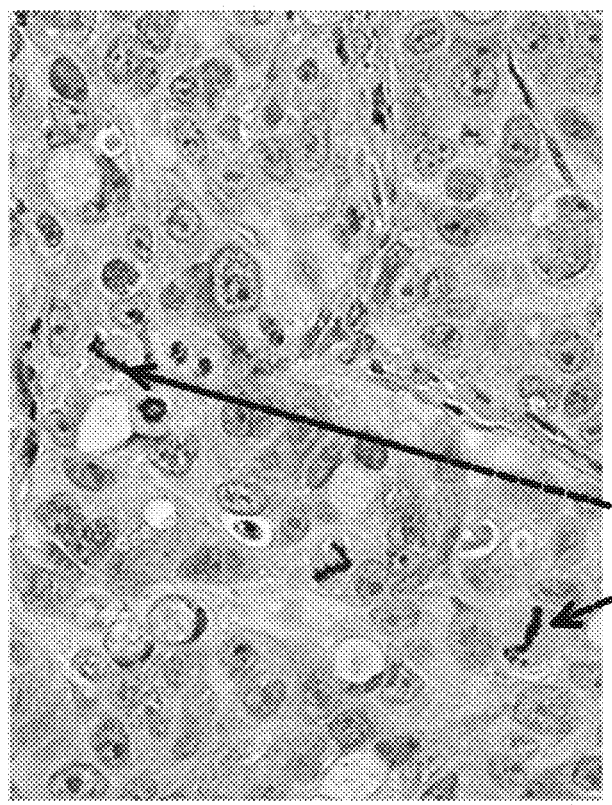
FIGS. 3A and 3B are hematoxylin and eosin stained tumor samples from untreated HT-29 xenograft mice (FIG. 3A) or from HT-29 xenograft mice treated with a humanized antibody of the disclosure (FIG. 3B). Dashed arrows point to cells undergoing mitosis. Solid arrows point to necrotic or apoptotic cells.
Figure 3B:
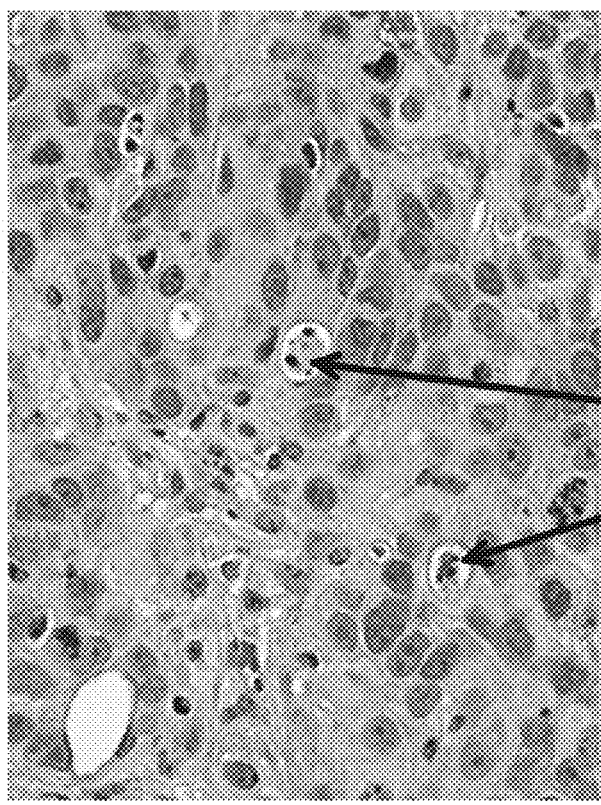
Figure 4B:
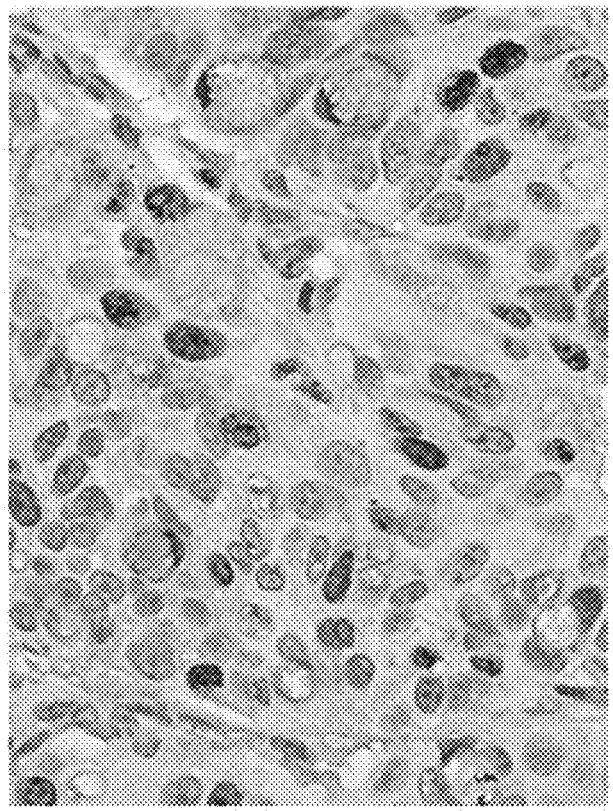
FIGS. 4A and 4B are Ki-67 stained tumor samples from untreated HT-29 xenograft mice (FIG. 4A) or from HT-29 xenograft mice treated with a humanized antibody of the disclosure (FIG. 4B). Stained nuclei are positive for Ki-67 and are indicative of actively dividing cells.
Figure 4A:
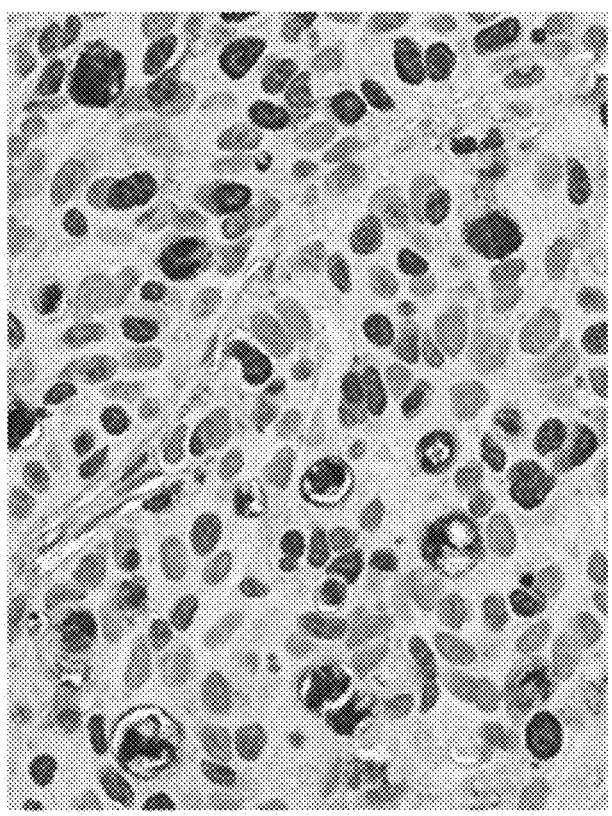
Figure 5A:
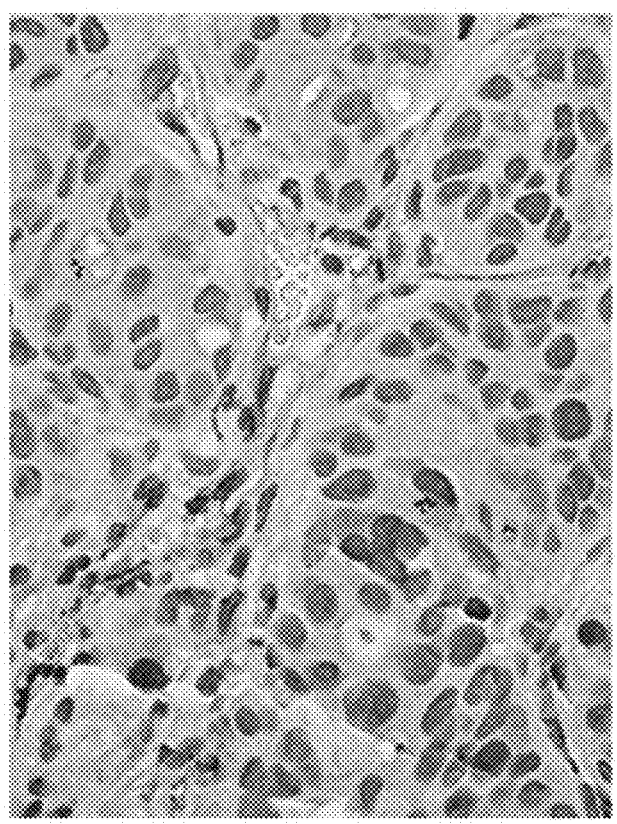
FIGS. 5A and 5B are CD-31 stained tumor samples from untreated HT-29 xenograft mice (FIG. 5A) or from HT-29 xenograft mice treated with a humanized antibody of the disclosure (FIG. 5B). Dark stain is positive for CD-31 and is indicative of endothelial cells.
Figure 5B:

Example 5: Effects of a Humanized 3E10 Antibody and Antibody Fragment on Xenograft Mice In order to test the effects of a humanized 3E10 antibody on tumor growth in a xenograft mouse model, an antibody of the disclosure (an antibody comprising humanized heavy chain (comprising the amino acid sequence of one of SEQ ID NO: 38, SEQ ID NO: 39 or SEQ ID NO: 10; associated with an IgG constant domain) and a humanized light chain (comprising one of SEQ ID NO: 8 or SEQ ID NO: 40)) was administered to an HT-29 (colon cancer) xenograft mouse model. HT-29 xenograft mice were generated by injecting HT-29 cells (with matrigel) subcutaneously into nu/nu mice and allowed to grow until tumors were a volume of 100 mm$^3$ before initiating treatment. Two groups of the HT-29 xenograft mice were either untreated or intravenously administered the antibody at 1 mg/kg three times over a four week period (day 1, day 11 and day 25). As demonstrated by FIG. 2, antibody administration significantly delayed tumor growth (as measured using calipers) in the xenograft mice as compared to untreated control mice. In addition, tumor samples from treated mice displayed hematoxylin and eosin staining consistent with there being fewer mitotic figures and more necrotic or apoptotic cells in the tumors of antibody treated mice as compared to untreated mice (FIGS. 3A and 3B). Treated tumor samples from antibody treated mice also showed signs of greatly reduced tumor cell proliferation as compared to tumor samples from treated control mice (FIGS. 4A and 4B). Moreover, tumor samples from antibody-treated mice showed signs of altered CD-31 (a neocapillary marker) staining as compared to tumor samples from untreated control mice (FIGS. 5A and 5B), which is consistent with a collapse of the tumor neocapillary architecture in the treated samples. In a parallel experiment, the humanized 3E10 antibody described above was tested in comparison to a full-length 3E10 antibody lacking Fc effector function. This "effector dead" antibody had a glutamine, rather than an asparagine, at the position corresponding to Kabat position 297 of the heavy chain, but otherwise had the idential amino acid sequence as the antibody used in HT-29 xenograft experiment described above. As illustrated in FIG. 2B, the "effector dead" antibody had a comparable impact on delaying tumor growth in the HT-29 xenograft mice as compared to the antibody retaining effector function.

Figure 6:
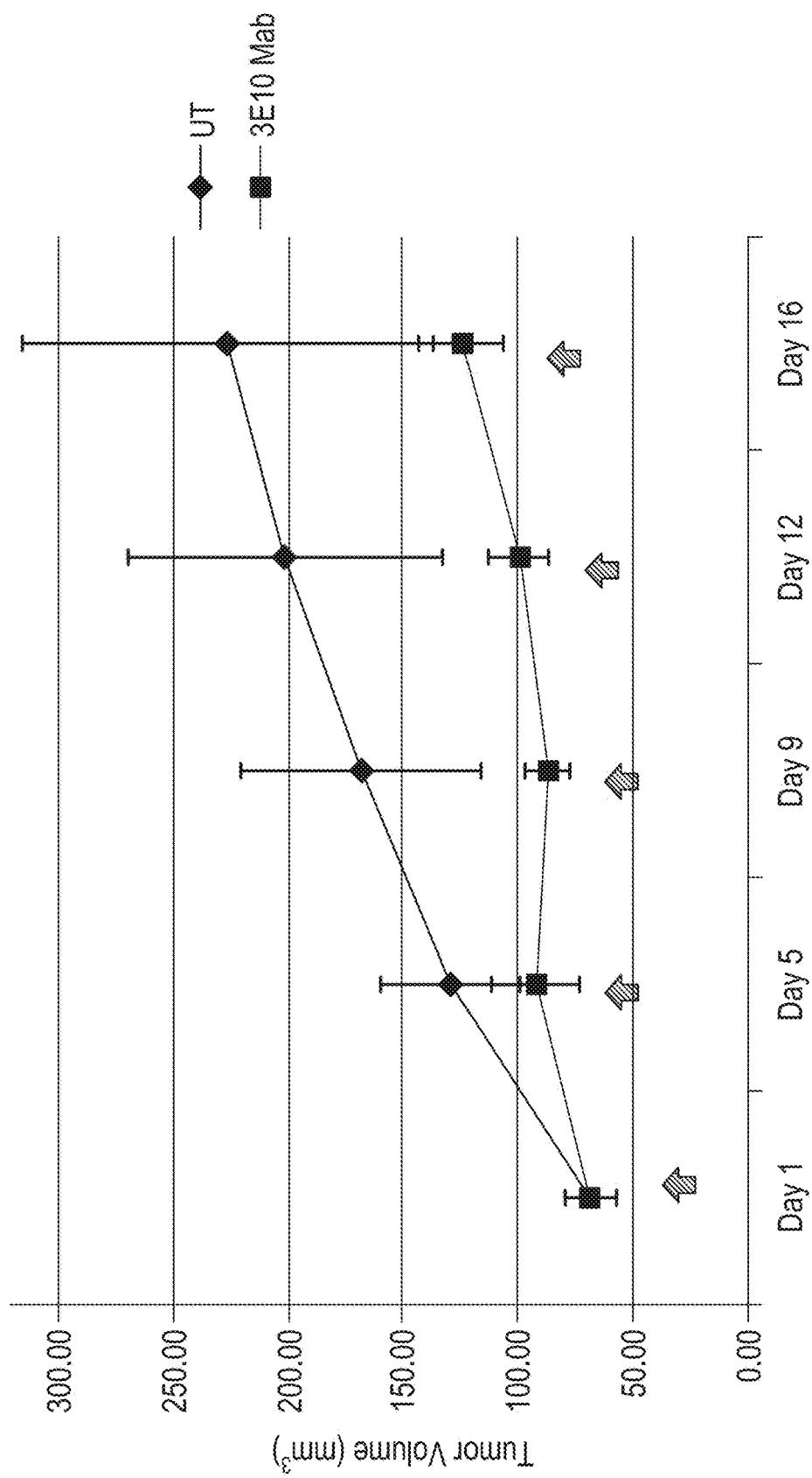
FIG. 6 is a line graph illustrating the effects of a humanized antibody (3E10 Mab) of the disclosure on tumor volume in a SKOV-3 xenograft mouse model as compared to an untreated (UT) control. Tumor volume was measured in 15 mice at days 1 and 5, and in ten mice at all timepoints after day five. Arrows indicate dates of antibody administration (each dose at 1 mg/kg).

In a separate study, the effects of the humanized 3E10 antibody having Fc effector function was tested in a SKOV-3 xenograft mouse model. SKOV-3 xenograft mice were generated by injecting SKOV-3 cells (with matrigel) subcutaneously into nu/nu mice and allowed to grow until tumors were a volume of 100 mm$^3$ before initiating treatment. Two groups of fifteen SKOV-3 (a platin-resistant ovarian cancer) xenograft mice were either untreated (treated with saline) or intravenously administered the humanized antibody at 1 mg/kg twice weekly for up to three weeks. Five mice from each group were sacrificed for tumor analysis following the second injection. As demonstrated in FIG. 6, antibody administration markedly delayed tumor growth (as measured using calipers) in the xenograft mice as compared to untreated control mice. In addition, histological analysis of tumor samples from treated and untreated control animals showed that treated samples were smaller (e.g., decrease in tumor volume), had more necrotic cells and fibrosis, and had fewer proliferating cells (as measured by Ki67 staining) as compared to tumor samples from untreated control mice. These results surprisingly demonstrate a strong effect of the humanized 3E10 antibody on tumor growth and proliferation in a tumor type known to be resistant to platin chemotherapeutic agents. See, e.g., Singh et al., 2009, Phytother Res., 23(8):1066-1074.

Figure 7:
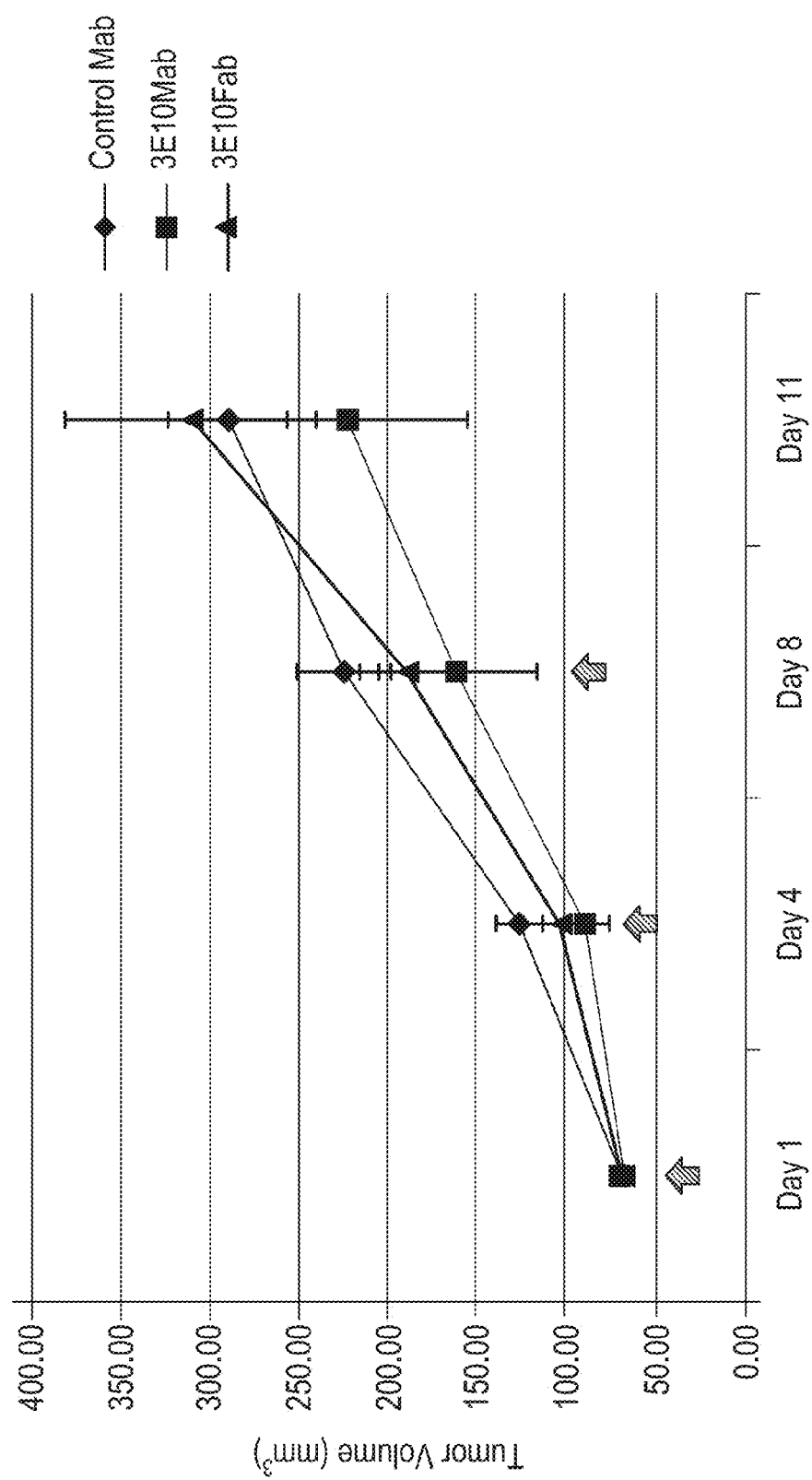
FIG. 7 is a line graph illustrating the effects of a humanized antibody (3E10 Mab) of the disclosure or humanized antigen-binding fragment (3E10 Fab) of the disclosure on tumor volume in a HCT-116 xenograft mouse model as compared to mice treated with a control monoclonal antibody (IgG1—human myeloma plasma 16-16-090707-1M-10 mg (Athens Research)). Tumor volume was measured in 10 mice per group at the indicated time points. Arrows indicate dates of antibody administration (each dose at 1 mg/kg).

In a further study, 3 groups of HCT-116 (colon cancer) xenograft mice were either treated with a monoclonal control antibody (IgG1-human myeloma plasma 16-16-090707-1 M-10 mg (Athens Research)), the full-length humanized antibody of the disclosure (with effector function) used for the HT-29 and SKOV-3 studies, or a Fab variant of the full-length humanized 3E10. The antibodies or Fab were intravenously administered to the mice at 1 mg/kg (on each of day 1, day 4 and day 8). As demonstrated in FIG. 7, mice treated with the full-length humanized antibody of the disclosure displayed a delay in tumor growth as compared to mice treated with the control antibody. In addition, mice treated with the full-length humanized antibody of the disclosure displayed more fibrosis and decreased proliferation (as measured by Ki67 staining) than that observed in mice treated with the control antibody.

Figure 8:
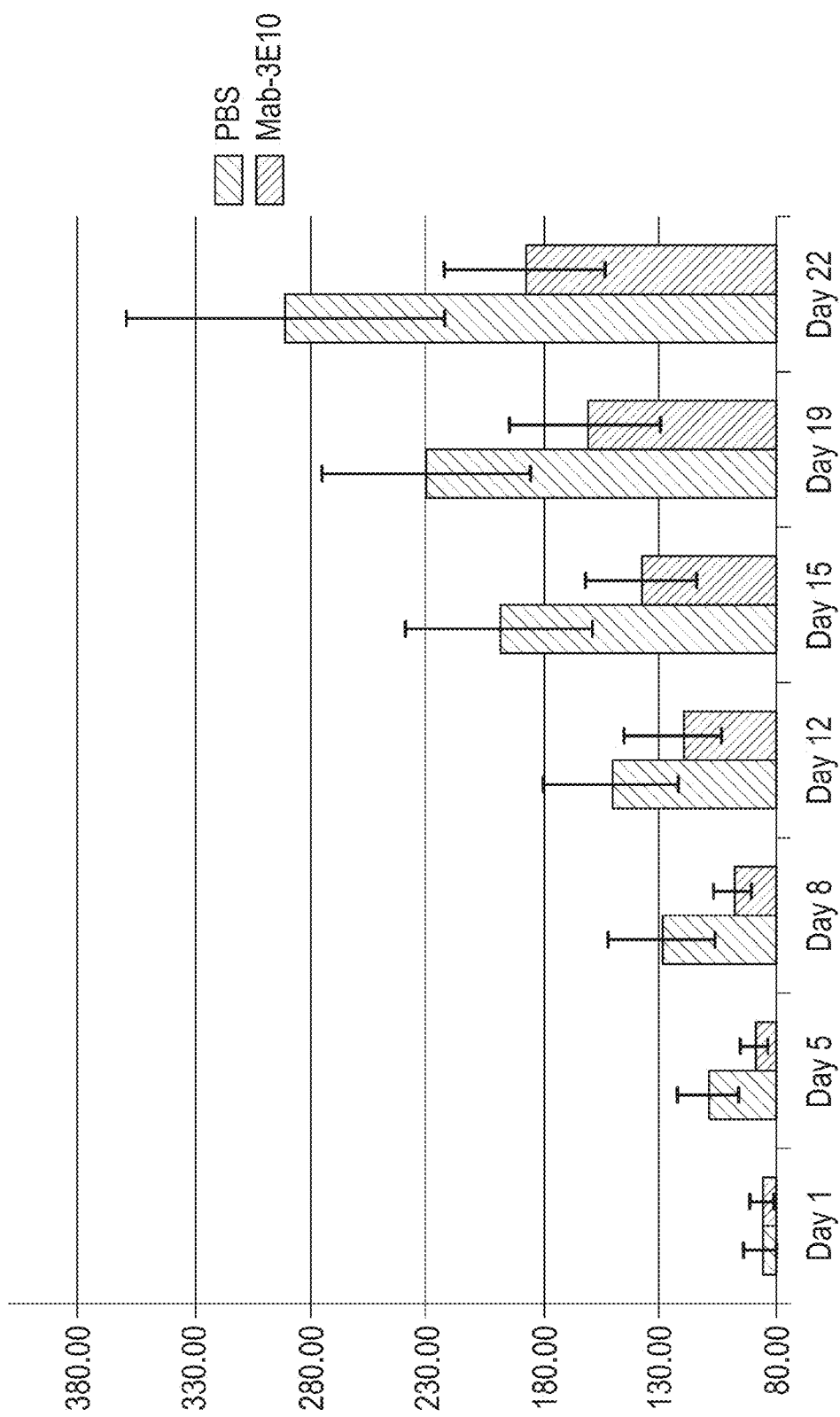
FIG. 8 is a bar graph illustrating the effects of a humanized antibody (3E10 Mab) of the disclosure on tumor volume in a U251 xenograft mouse model as compared to untreated control (PBS) xenograft mice. Tumor volume was measured in fourteen PBS treated mice, and fifteen 3E10 Mab treated mice. Mice were administered PBS or a humanized antibody of the disclosure intravenously twice weekly at a dose of 1 mg/kg.

In another study, two groups of U251 (glioma) xenograft mice were either treated with a full-length "effector dead" humanized antibody of the disclosure or with PBS. The antibodies of the disclosure were intravenously administered to the mice at 1 mg/kg twice a week. As demonstrated in FIG. 8, mice treated with the full-length humanized antibody displayed a delay in tumor growth as compared to mice treated with PBS.

Figure 9A:
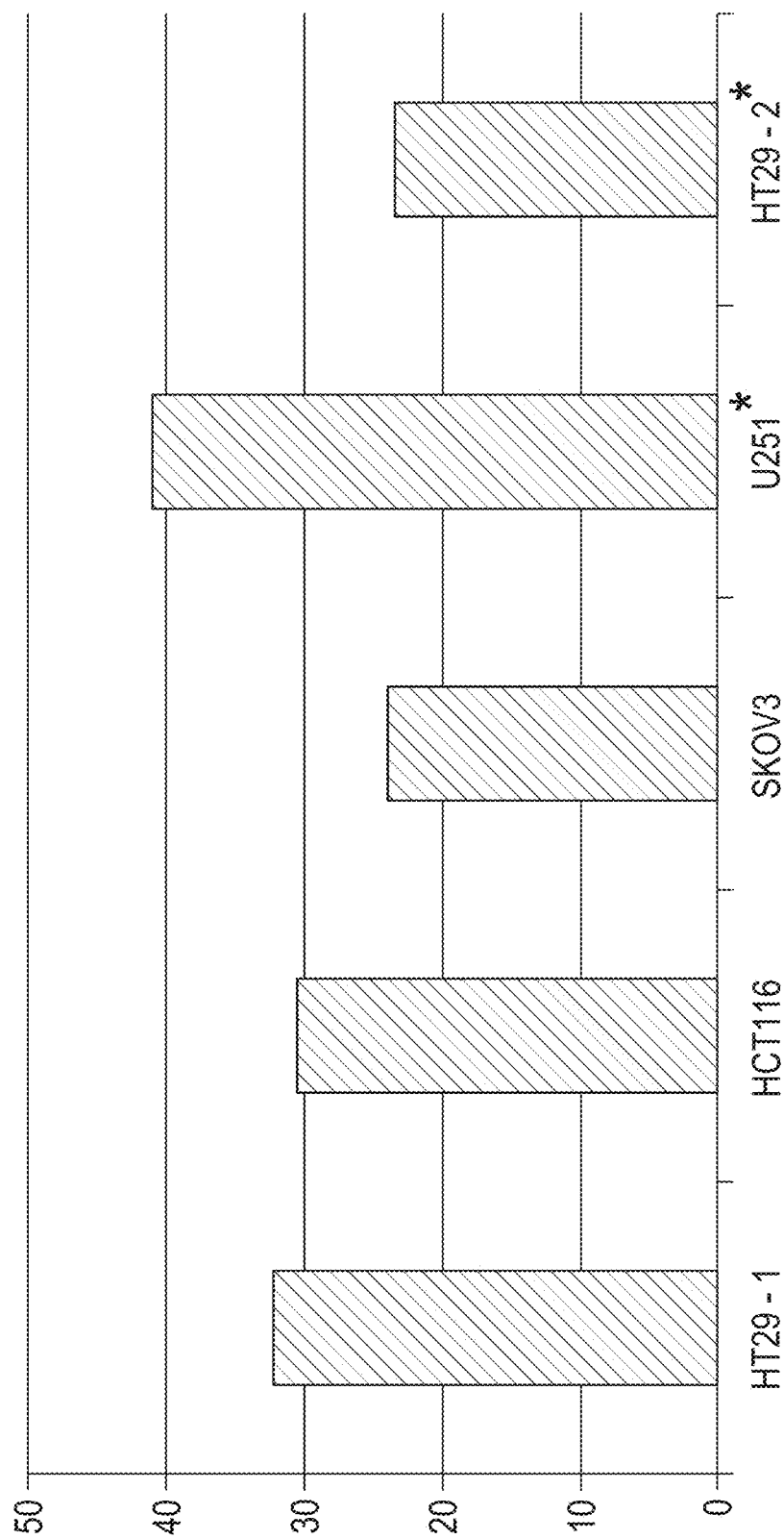
FIGS. 9A and 9B are bar graphs illustrating the results from a multi-study analysis in which the effects of a humanized antibody (3E10 Mab) of the disclosure or vehicle control on tumor volume were determined in various tumor xenograft mouse models. Tumor volumes were measured on day 1 and were compared to tumor volume measurements obtained on days 10, 11, or 12 post-injection. A humanized antibody of the disclosure (3E10 Mab) antibody lacking Fc effector function was used to treat U251 and HT29-2 xenograft mice (starred mouse groups in FIG. 9A). All other xenograft mouse models were treated with a 3E10 Mab antibody retaining Fc effector function. Treatment groups consisted of 10-15 mice per group, and mice were administered the humanized antibody intravenously at a dose of 1 mg/kg. Each mouse model was tested in a separate study.
Figure 9B:
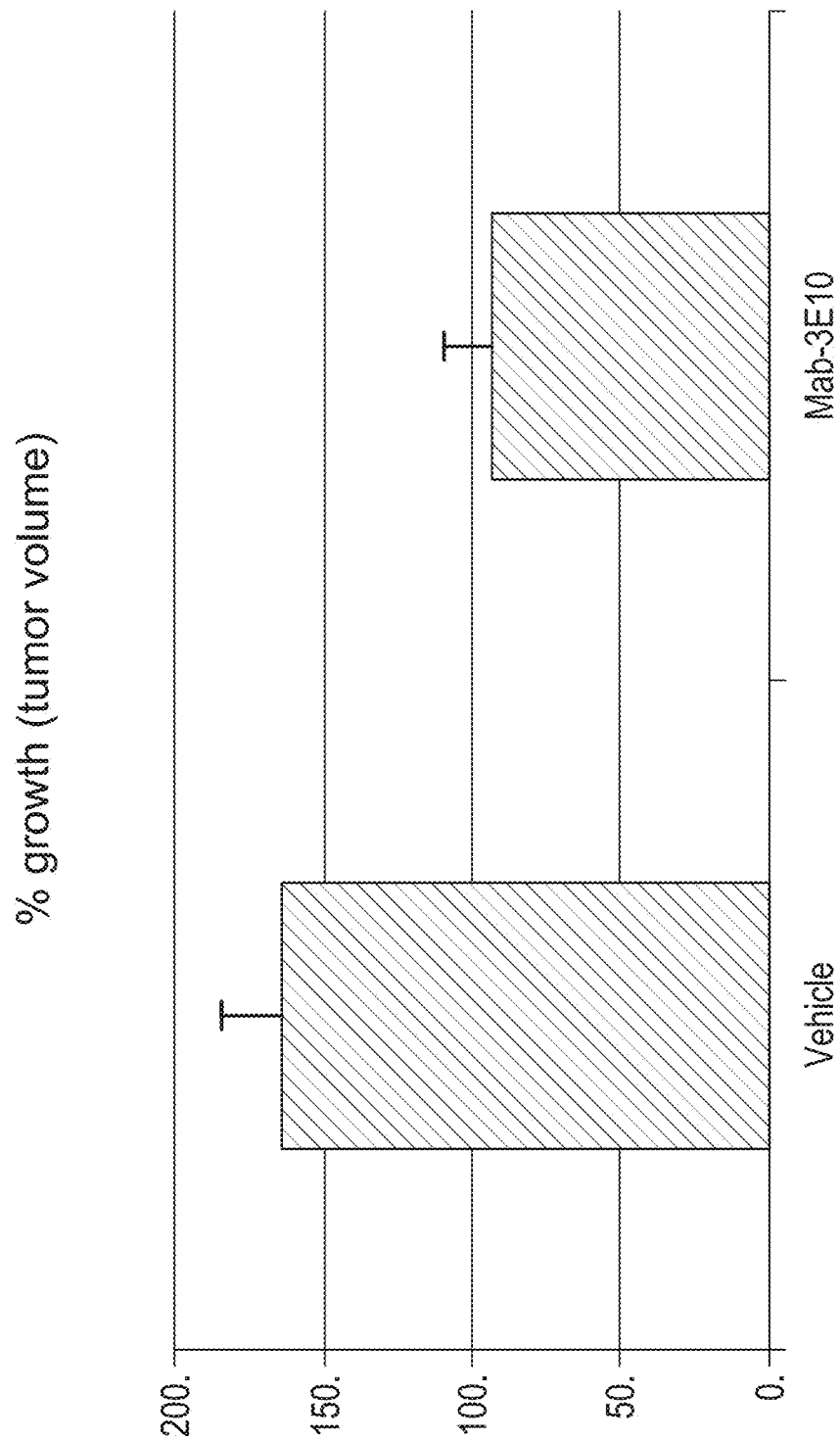

FIGS. 9A and 9B provides a graphical comparison of the effects of the humanized antibodies of the disclosure described above (either having effector function or "effector dead") or vehicle control on the various xenograft mouse models from the studies discussed above. Tumor volumes were measured on day 1 and compared to tumor volume measurements obtained on days 10, 11, or 12 post-injection. A 3E10 Mab antibody lacking Fc effector function was used to treat U251 and HT29-2 xenograft mice (starred mouse groups in FIG. 9A). All other xenograft mouse models were treated with a 3E10 Mab antibody retaining Fc effector function. As described above for each of the xenograft models tested, treatment groups consisted of 10-15 mice per group, and mice were administered the humanized antibody intravenously at a dose of 1 mg/kg. Each mouse model was tested in a separate study.

FIG. 9A illustrates the results from this multi-study analysis in terms of tumor growth inhibition as compared to untreated controls. FIG. 9B displays results of an ANOVA statistical analysis of the multi-study tumor growth data. FIG. 9B illustrates the results in terms of average percent growth of tumors in all 3E10 Mab antibody treated and vehicle control treated xenograft mice. More than a 43% reduction in tumor growth ($p<0.0039$) was observed in xenograft mice treated with the antibody. In addition, the omega squared value for the combined effect of the antibody or vehicle on tumor growth in all xenograft mice tested was 0.16. As such, only 16% of variability in tumor growth can be attributed to treatment effect differences across the various cancer cell lines.

Example 6: Effects of a Humanized Antibody of the Disclosure on Cancer Cells with Active or Inactivated Mismatch Repair Capablities Hereditary non-polyposis colon cancer (HNPCC), also known as Lynch Syndrome, is the most common form of hereditary colon cancer and is a syndrome associated with deficient DNA mismatch repair. In some embodiments, a subject with HNPCC has mutation in one or more of MLH1, MSH2 or MSH6.

As described in Example 5, a representative internalizing moiety of the disclosure was capable of inhibiting tumor growth in murine tumor xenograft models having cancer cells with impaired mismatch repair. Specifically, both SKOV-3 and HCT-116 cells have a mutation in the MLH1 gene. To further examine whether the internalizing moieties of the disclosure can inhibit cancer cell proliferation independent of mismatch repair functionality (thus confirming a mechanism of the internalizing moieties outside mismatch repair inhibition), the effects of the effector dead humanized antibody described in Example 1 are examined in a comparison study using several cell lines in which mismatch repair is active or is deficient. Specifically, the cell lines to be tested include three cell lines having active mismatch repair: 1) a normal human colon cell line (CCD-18Co (ATCC CRL-1459))); 2) a human colon cancer cell line (HT-29 (ATCC HTB-38)); and 3) a human ovarian cell lines (OVCAR-3 (ATCC HTB-161); and three cell lines having inactive mismatch repair: 1) a human colon cancer cell line having a mutation in the MLH1 gene (HCT 116 (ATCC CCL-247); 2) a human ovarian cancer cell line having a mutation in the MLH1 gene (SK-OV-3 (ATCC HTB-77); and 3) a human ovarian cancer cell line having a mutation in the MSH2 gene (HC-59 (AddexBio C0026001). The effects of the humanized antibody on the cells are assessed for at least the following parameters: in vitro cell killing, in vivo xenograft tumor reduction, and effects on downstream signaling (e.g., mRNA changes, protein changes, and phosphorylation changes (e.g. assessment of DNA damage response element changes)).

SEQUENCE INFORMATION

SEQ ID NO: 1 - heavy chain variable ($V_H$) domain CDR1 of exemplary 3E10 molecule, in accordance with CDRs as defined by the IMGT system
GFTFSNYG SEQ ID NO: 2 - heavy chain variable ($V_H$) domain CDR2 of exemplary 3E10 molecule, in accordance with CDRs as defined by the IMGT system
ISSGSSTI SEQ ID NO: 3 - heavy chain variable ($V_H$) domain CDR3 of exemplary 3E10 molecule, in accordance with CDRs as defined by the IMGT system
ARRGLLLDY SEQ ID NO: 4 - light chain variable ($V_L$) domain CDR1 of exemplary 3E10 molecule, in accordance with CDRs as defined by the IMGT system
KSVSTSSYSY SEQ ID NO: 5 - light chain variable ($V_L$) domain CDR2 of exemplary 3E10 molecule, in accordance with CDRs as defined by the IMGT system
YAS SEQ ID NO: 6 - light chain variable ($V_L$) domain CDR3 of exemplary 3E10 molecule, in accordance with CDRs as defined by the IMGT system
QHSREFPWT SEQ ID NO: 7 - amino acid sequence of murine 3E10 light chain variable domain ($V_L$) used as parent VL
DIVLTQSPASLAVSLGQRATISCRASKSVSTSSYSYMHWYQQKPGQPPKL

| SEQUENCE INFORMATION |
| --- |
| LIKYASYLESGVPARFSGSGSGTDFHLNIHPVEEEDAATYYCQHSREFPW TFGGGTKLELK |
| SEQ ID NO: 8 - amino acid sequence of humanized 3E10 light chain variable domain (hVL2) DIQMTQSPSSLSASVGDRVTISCRASKSVSTSSYSYMHWYQQKPEKAPKL LIKYASYLQSGVPSRFSGSGSGTDFTLTISSLQPEDVATYYCQHSREFPW TFGAGTKLELK |
| SEQ ID NO: 9 - amino acid sequence of murine 3E10 heavy chain variable domain ($V_H$) used as parent VH EVQLVESGGGLVKPGGSRKLSCAASGFTFSNYGMHWVRQAPEKGLEWVAY ISSGSSTIYYADTVKGRFTISRDNAKNTLFLQMTSLRSEDTAMYYCARRG LLLDYWGQGTTLTVSS |
| SEQ ID NO: 10 - amino acid sequence of humanized 3E10 heavy chain variable domain (hVH3) EVQLQESGGGVVQPGGSLRLSCAASGFTFSNYGMHWIRQAPGKGLEWVSY ISSGSSTIYYADSVKGRFTISRDNSKNTLYLQMNSLRSEDTAVYYCARRG LLLDYWGQGTLVTVSS |
| SEQ ID NO: 11 = representative 12-mer GCGCTGCTACATCCACGCAGCTGCGCGGAGCGCAGCTGCGTGGATGTAGC AGCGC |
| SEQ ID NO: 12 - Nucleotide sequence encoding murine 3E10 light chain (Genbank accession number L34051) GACATTGTGCTGACACAGTCTCCTGCTTCCTTAGCTGTATCTCTGGGGCA GAGGGCCACCATCTCCTGCAGGGCCAGCAAAAGTGTCAGTACATCTAGCT ATAGTTACATGCACTGGTACCAACAGAAACCAGGACAGCCACCCAAACTC CTCATCAAGTATGCATCCTACCTAGAATCTGGGGTTCCTGCCAGGTTCAG TGGCAGTGGGTCTGGGACAGACTTTCACCTCAACATCCATCCTGTGGAGG AGGAGGATGCTGCAACATATTACTGTCAGCACAGTAGGGAGTTTCCGTGG ACGTTCGGTGGAGGCACCAAGCTGGAGTTGAAA |
| SEQ ID NO: 13 - Nucleotide sequence encoding murine heavy chain sequence (Genbank accession number L16982) GAGGTGCAGGTGGTGGAGTCTGGGGGAGGCTTAGTGAAGCCTGGAGGGTC CCGGAAACTCTCCTGTGCAGCCTCTGGATTCACTTTCAGTAACTATGGAA TGCACTGGGTCCGTCAGGCTCCAGAGAAGGGGCTGGAGTGGGTTGCATAC ATTAGTAGTGGCAGTAGTACCATCTACTATGCAGACACAGTGAAGGGCCG ATTCACCATCTCCAGAGACAATGCCAAGAACACCCTGTTCCTGCAAATGA CCAGTCTAAGGTCTGAGGACACAGCCATGTATTACTGTGCAAGGCGGGGG TTACTACTTGACTACTGGGGCCAAGGCACCACTCTCACAGTCTCCTCA |
| SEQ ID NO: 14 = FoxA1 motif GTAAACAA |
| SEQ ID NO: 15 - human kappa light chain RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC |
| SEQ ID NO: 16 - Exemplary signal sequence MDMRVPAQLLGLLLLWLRGARC |
| SEQ ID NO: 17 - Exemplary signal sequence MEFGLSWLFLVAILKGVQC |
| SEQ ID NO: 18 - Exemplary blunt end DNA substrate 5'-GGG TGA ACC TGC AGG TGG GCA AAG ATG TCC-3' |
| SEQ ID NO: 19 - representative 12 mer bound by representative humanized internalizing moiety GCGCTGCAATGAATTATAAGCTGCGCGGAGCGCAGCTTATAATTCATTGC AGCGC |
| SEQ ID NO: 20 - representative 12 mer bound by representative humanized internalizing moiety GCGCTGCAATATAGTCTAAGCTGCGCGGAGCGCAGCTTAGACTATATTGC AGCGC |
| SEQ ID NO: 21 - representative 12 mer bound by representative humanized internalizing moiety GCGCTGCTATATAAGTCTAGCTGCGCGGAGCGCAGCTAGACTTATATAGC AGCGC |
| SEQ ID NO: 22 - representative 12 mer bound by representative humanized internalizing moiety GCGCTGCACATAAATTTACGCTGCGCGGAGCGCAGCGTAAATTTATGTGC AGCGC |
| SEQ ID NO: 23 - representative 12 mer bound by representative humanized internalizing moiety GCGCTGCTAGAAATATATAGCTGCGCGGAGCGCAGCTATATATTTCTAGC AGCGC |
| SEQ ID NO: 24 - representative FoxA1 probe bound by representative humanized internalizing moiety ACTTTAGGTAAACAACTAAAGTGGAACTTTAGTTGTTTACCTAAAGT |
| SEQ ID NO: 25 - representative FoxA1 probe bound by representative humanized internalizing moiety ATCTTAAGTAAACAATTAAGATGGAATCTTAATTGTTTACTTAAGAT |
| SEQ ID NO: 26 - representative FoxA1 probe bound by representative humanized internalizing moiety TCATATAGTAAACAATATATGAGGATCATATATTGTTTACTATATGA |
| SEQ ID NO: 27 - representative T-rich bound by representative humanized internalizing moiety CTGTCTCGTAGCACTCGCGATACGGAGTATCGTTTTTTTTTTTAGACAG |
| SEQ ID NO: 28 - "AGIH" AGIH |
| SEQ ID NO: 29 - "SAGIH" SAGIH |
| SEQ ID NO: 30 - linker sequence "GS3" GGGGSGGGGSGGGGS |
| SEQ ID NO: 31 - linker sequence "GSTS" GSTSGSGKSSEGKG |
| SEQ ID NO: 32 - heavy chain variable domain CDR1 of VH (as that VH is defined with reference to SEQ ID NO: 9), in accordance with CDRs as defined by Kabat NYGMH |

| SEQUENCE INFORMATION |
|---|
| SEQ ID NO: 33 - heavy chain variable domain CDR2 of VH (as that VH is defined with reference to SEQ ID NO: 9), in accordance with CDRs as defined by Kabat<br>YISSGSSTIYYADTVKG |
| SEQ ID NO: 34 - heavy chain variable domain CDR3 of VH (as that VH is defined with reference to SEQ ID NO: 9), in accordance with CDRs as defined by Kabat<br>RGLLLDY |
| SEQ ID NO: 35 - light chain variable domain CDR1 of VL (as that VL is defined with reference to SEQ ID NO: 7), in accordance with CDRs as defined by Kabat<br>RASKSVSTSSYSYMH |
| SEQ ID NO: 36 - light chain variable domain CDR2 of VL (as that VL is defined with reference to SEQ ID NO: 7), in accordance with CDRs as defined by Kabat<br>YASYLES |
| SEQ ID NO: 37 - light chain variable domain CDR3 of VL (as that VL is defined with reference to SEQ ID NO: 7), in accordance with CDRs as defined by Kabat<br>QHSREFPWT |
| SEQ ID NO: 38 - amino acid sequence of humanized 3E10 heavy chain (hVH1)<br>EVQLVQSGGGLIQPGGSLRLSCAASGFTFSNYGMHWVRQAPGKGLEWVSY<br>ISSGSSTIYYADSVKGRFTISRDNSKNTLYLQMNSLRAEDTAVYYCARRG<br>LLLDYWGQGTTVTVSS |
| SEQ ID NO: 39 - amino acid sequence of humanized 3E10 heavy chain (hVH2)<br>EVQLVESGGGLIQPGGSLRLSCAASGFTFSNYGMHWVRQAPGKGLEWVSY<br>ISSGSSTIYYADSVKGRFTISRDNSKNTLYLQMTSLRAEDTAVYYCARRG<br>LLLDYWGQGTTLTVSS |
| SEQ ID NO: 40 - amino acid sequence of humanized 3E10 light chain (hVL1)<br>DIQMTQSPSSLSASVGDRVTITCRASKSVSTSSYSYLAWYQQKPEKAPKL<br>LIKYASYLQSGVPSRFSGSGSGTDFTLTISSLQPEDFATYYCQHSREFPW<br>TFGAGTKLELK |
| SEQ ID NO: 41 - amino acid sequence of a humanized 3E10 light chain<br>DIVLTQSPASLAVSPGQRATITCRASKSVSTSSYSYMHWYQQKPGQPPKL<br>LIYYASYLESGVPARFSGSGSGTDFTLTINPVEANDTANYYCQHSREFPW<br>TFGQGTKVEIK |
| SEQ ID NO: 42 - amino acid sequence of a humanized 3E10 heavy chain<br>EVQLVESGGGLVQPGGSLRLSCSASGFTFSNYGMHWVRQAPGKGLEYVSY<br>ISSGSSTIYYADTVKGRFTISRDNSKNTLYLQMSSLRAEDTAVYYCVKRG |

| SEQUENCE INFORMATION |
|---|
| LLLDYWGQGTLVTVSS |
| SEQ ID NO: 43 - Humanized Fv3E10<br>DIVLTQSPASLAVSPGQRATITCRASKSVSTSSYSYMHWYQQKPGQPPKL<br>LIYYASYLESGVPARFSGSGSGTDFTLTINPVEANDTANYYCQHSREFPW<br>TFGQGTKVEIKGGGGSGGGGSGGGGSEVQLVESGGGLVQPGGSLRLSCSA<br>SGFTFSNYGMHWVRQAPGKGLEYVSYISSGSSTIYYADTVKGRFTISRDN<br>SKNTLYLQMSSLRAEDTAVYYCVKRGLLLDYWGQGTLVTVSS |
| SEQ ID NO: 44 = representative 12-mer<br>GCGCTGCCGAGAGCGGCCTGCTGCGCGGAGCGCAGCAGGCCGCTCTCGGC<br>AGCGC |
| SEQ ID NO: 45 - linker sequence<br>GGSGGGSGGGSGG |
| SEQ ID NO: 46 - representative FoxA1 probe<br>TTCCTGCGTAAACAAGCAGGAAGGATTCCTGCTTGTTTACGCAGGAA |
| SEQ ID NO: 47 - His Tag<br>HHHHHH |
| SEQ ID NO: 48 - Exemplary c-myc Tag<br>EQKLISEEDL |
| SEQ ID NO: 49 - heavy chain variable domain CDR2 of certain antibodies of the disclosure, in accordance with CDRs as defined by Kabat<br>YISSGSSTIYYADSVKG |
| SEQ ID NO: 50 - light chain variable domain CDR1 of certain antibodies of the disclosure, in accordance with CDRs as defined by Kabat<br>RASKSVSTSSYSYLA |
| SEQ ID NO: 51 - light chain variable domain CDR2 of certain antibodies of the disclosure, in accordance with CDRs as defined by Kabat<br>YASYLQS |
| SEQ ID NO: 52 - Fox consensus motif<br>TRTTKRY<br>(wherein R = A/G, Y = C/T, and K = T/G) |

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

I claim:

1. A method of treating a tumor in a subject in need thereof, comprising administering an antibody or antigen-binding fragment to the subject, wherein the antibody or antigen-binding fragment comprises a light chain variable (VL) domain and a heavy chain variable (VH) domain; wherein the VH domain comprises:
   a VH CDR1 having the amino acid sequence of SEQ ID NO: 1;
   a VH CDR2 having the amino acid sequence of SEQ ID NO: 2; and
   a VH CDR3 having the amino acid sequence of SEQ ID NO: 3,
which CDRs are according to the IMGT system; or
wherein the VH domain comprises:
   a VH CDR1 having the amino acid sequence of SEQ ID NO: 32;
   a VH CDR2 having the amino acid sequence of SEQ ID NO: 49; and
   a VH CDR3 having the amino acid sequence of SEQ ID NO: 34,
which CDRs are according to the Kabat system;
and the VL domain comprises:
   a VL CDR1 having the amino acid sequence of SEQ ID NO: 35 or 50;
   a VL CDR2 having the amino acid sequence of SEQ ID NO: 51; and
   a VL CDR3 having the amino acid sequence of SEQ ID NO: 37,
which CDRs are according to the Kabat system,
   wherein the antibody binds DNA with a $K_D$ of less than 100 nM and promotes transit across cellular membranes via an equilibrative nucleoside transporter 2 (ENT2) transporter.

2. The method of treating a tumor of claim 1, wherein the method includes reducing tumor growth, proliferation or survival.

3. The method of claim 2, wherein a reduction in tumor growth, proliferation or survival is determined by assessing mitotic markers in a tumor sample.

4. The method of claim 2, wherein a reduction in tumor growth, proliferation or survival is determined by assessing Ki-67 staining in a tumor sample.

5. The method of treating a tumor of claim 1, wherein the method includes promoting collapse of capillary blood vessels in a tumor.

6. The method of claim 5, wherein a collapse of capillary blood vessels in a tumor is determined by observing CD-31 staining patterns in a tumor sample.

7. The method of claim 1, wherein the tumor is in a subject, and the subject is a human.

8. The method of claim 1, wherein the tumor is a colorectal cancer, an ovarian cancer, a pancreatic cancer, a hereditary non-polyposis colon cancer (HNPCC), or an adenocarcinoma.

9. The method of claim 1, wherein the tumor is platin-resistant, or
   wherein the tumor is resistant to treatment with DNA repair inhibitors.

10. The method of claim 1, wherein the tumor is associated with microsatellite instability.

11. The method of claim 1, wherein the tumor has deficient DNA mismatch repair, or
   wherein the tumor has a mutation in any of the hMSH2, hMSH6 or hMLH1 genes, or
   wherein the tumor is BRCA2 deficient, or
   wherein the tumor is BRCA2 proficient.

12. The method of claim 1, wherein the method comprises administering the antibody or antigen-binding fragment more than once according to a dose and dosing schedule.

13. The method of claim 1, wherein the antibody or antigen-binding fragment thereof is administered to the subject as a monotherapy.

14. The method of claim 1, wherein the antibody or antigen-binding fragment thereof is administered to the subject in combination with an additional therapeutic treatment.

15. The method of claim 1, wherein the antibody or antigen-binding fragment is administered to the subject intravenously, intramuscularly, or subcutaneously.

16. The method of claim 1, wherein the antibody or antigen-binding fragment is a full length antibody or comprises a portion of an Fc domain, and which antibody or antigen-binding fragment is effective at a lower dose than a murine 3E10 full length antibody.

17. The method of claim 1, wherein the antibody or antigen-binding fragment is a Fab or Fab', and which antibody or antigen-binding fragment is effective at a lower dose than a murine 3E10 Fv or scFv.

18. The method of claim 1, wherein the antibody or antigen-binding fragment is a F(ab')2 fragment, and which antibody or antigen-binding fragment is effective at a lower dose than a murine a F(ab')2 fragment.

19. The method of claim 1, wherein the internalizing moiety is a full length antibody comprising a heavy chain constant domain and a light chain constant domain.

20. The method of claim 1, wherein the VH domain comprises:
the amino acid sequence of SEQ ID NO: 38,
the amino acid sequence of SEQ ID NO: 39, or
the amino acid sequence of SEQ ID NO: 10; and
wherein the VL domain comprises:
the amino acid sequence of SEQ ID NO: 40, or
the amino acid sequence of SEQ ID NO: 8.

21. A method of inhibiting proliferation of a cancerous cell or tumor cell, comprising contacting the tumor cell with an antibody or antigen-binding fragment, wherein the antibody or antigen-binding fragment comprises a light chain variable (VL) domain and a heavy chain variable (VH) domain; wherein the VH domain comprises:
a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3,
which CDRs are according to the IMGT system; or
wherein the VH domain comprises:
a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34,
which CDRs are according to the Kabat system;
and the VL domain comprises:
a VL CDR1 having the amino acid sequence of SEQ ID NO: 35 or 50;
a VL CDR2 having the amino acid sequence of SEQ ID NO: 51; and
a VL CDR3 having the amino acid sequence of SEQ ID NO: 37,
which CDRs are according to the Kabat system,
wherein the antibody binds DNA with a $K_D$ of less than 100 nM and promotes transit across cellular membranes via an equilibrative nucleoside transporter 2 (ENT2) transporter.

22. A method of decreasing Ki-67 or CD31 expression in a tumor, comprising contacting the tumor cell with an antibody or antigen-binding fragment, wherein the antibody or antigen-binding fragment comprises a light chain variable (VL) domain and a heavy chain variable (VH) domain; wherein the VH domain comprises:
a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3,
which CDRs are according to the IMGT system; or
wherein the VH domain comprises:
a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34,
which CDRs are according to the Kabat system;
and the VL domain comprises:
a VL CDR1 having the amino acid sequence of SEQ ID NO 35 or 50;
a VL CDR2 having the amino acid sequence of SEQ ID NO 51; and
a VL CDR3 having the amino acid sequence of SEQ ID NO: 37,
which CDRs are according to the Kabat system,
wherein the antibody binds DNA with a $K_D$ of less than 100 nM and promotes transit across cellular membranes via an equilibrative nucleoside transporter 2 (ENT2) transporter.

* * * * *